(12) United States Patent
Nasoff et al.

(10) Patent No.: US 11,484,604 B2
(45) Date of Patent: Nov. 1, 2022

(54) IMMUNOCONJUGATES TARGETING CD46 AND METHODS OF USE THEREOF

(71) Applicant: Fortis Therapeutics, Inc., La Jolla, CA (US)

(72) Inventors: Marc Nasoff, La Jolla, CA (US); Andrew Dorr, Solana Beach, CA (US)

(73) Assignee: FORTIS THERAPEUTICS, INC., La Jolla, CA (US)

(*) Notice: Subject to any disclaimer, the term of this patent is extended or adjusted under 35 U.S.C. 154(b) by 0 days.

(21) Appl. No.: 17/395,358

(22) Filed: Aug. 5, 2021

(65) Prior Publication Data

US 2022/0047712 A1 Feb. 17, 2022

Related U.S. Application Data

(60) Provisional application No. 63/062,740, filed on Aug. 7, 2020.

(51) Int. Cl.
| | | |
|---|---|---|
| *A61K 39/395* | (2006.01) | |
| *A61K 47/68* | (2017.01) | |
| *A61K 47/26* | (2006.01) | |
| *C07K 16/30* | (2006.01) | |

(52) U.S. Cl.
CPC .......... *A61K 47/6803* (2017.08); *A61K 47/26* (2013.01); *C07K 16/3069* (2013.01)

(58) Field of Classification Search
None
See application file for complete search history.

(56) References Cited

U.S. PATENT DOCUMENTS

| | | | |
|---|---|---|---|
| 4,414,148 A | 11/1983 | Jansen et al. |
| 4,439,196 A | 3/1984 | Higuchi |
| 4,447,224 A | 5/1984 | DeCant, Jr. et al. |
| 4,447,233 A | 5/1984 | Mayfield |
| 4,469,863 A | 9/1984 | Ts'o et al. |
| 4,474,814 A | 10/1984 | Fujita et al. |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,542,225 A | 9/1985 | Blattler et al. |
| 4,545,985 A | 10/1985 | Pastan et al. |
| 4,569,789 A | 2/1986 | Blattler et al. |
| 4,589,071 A | 5/1986 | Yamamuro et al. |
| 4,596,556 A | 6/1986 | Morrow et al. |
| 4,618,492 A | 10/1986 | Blattler et al. |
| 4,625,014 A | 11/1986 | Senter et al. |
| 4,659,839 A | 4/1987 | Nicolotti et al. |
| 4,671,958 A | 6/1987 | Rodwell et al. |
| 4,680,338 A | 7/1987 | Sundoro |
| 4,694,778 A | 9/1987 | Learn et al. |
| 4,699,784 A | 10/1987 | Shih et al. |
| 4,790,824 A | 12/1988 | Morrow et al. |
| 4,816,567 A | 3/1989 | Cabilly et al. |
| 4,866,132 A | 9/1989 | Obligin et al. |
| 4,894,443 A | 1/1990 | Greenfield et al. |
| 4,921,963 A | 5/1990 | Skov et al. |
| 4,941,880 A | 7/1990 | Burns |
| 4,956,778 A | 9/1990 | Naito |
| 4,957,735 A | 9/1990 | Huang |
| 4,975,369 A | 12/1990 | Beavers et al. |
| 5,034,506 A | 7/1991 | Summerton et al. |
| 5,064,413 A | 11/1991 | McKinnon et al. |
| 5,064,849 A | 11/1991 | Suzuki et al. |
| 5,075,431 A | 12/1991 | Shively et al. |
| 5,081,235 A | 1/1992 | Shively et al. |
| 5,091,513 A | 2/1992 | Huston et al. |
| 5,132,405 A | 7/1992 | Huston et al. |
| 5,169,939 A | 12/1992 | Gefter et al. |
| 5,202,238 A | 4/1993 | Fell, Jr. et al. |
| 5,204,244 A | 4/1993 | Fell et al. |
| 5,216,141 A | 6/1993 | Benner |
| 5,223,409 A | 6/1993 | Ladner et al. |
| 5,231,026 A | 7/1993 | Chang |
| 5,235,033 A | 8/1993 | Summerton et al. |
| 5,256,334 A | 10/1993 | Smid et al. |
| 5,264,586 A | 11/1993 | Nicolaou et al. |
| 5,292,867 A | 3/1994 | Chang |
| 5,312,335 A | 5/1994 | McKinnon et al. |
| 5,346,981 A | 9/1994 | Sarpeshkar et al. |
| 5,354,847 A | 10/1994 | Liu et al. |
| 5,374,548 A | 12/1994 | Caras |

(Continued)

FOREIGN PATENT DOCUMENTS

| | | |
|---|---|---|
| EP | 0188256 A2 | 7/1986 |
| EP | 0404097 A2 | 12/1990 |
| EP | 1184458 A1 | 3/2002 |
| JP | 2005511525 A | 4/2005 |
| WO | WO-9100996 A1 | 1/1991 |
| WO | WO-9203918 A1 | 3/1992 |

(Continued)

OTHER PUBLICATIONS

Agnelli et al. A SNP microarray and FISH-based procedure to detect allelic imbalances in multiple myeloma: an integrated genomics approach reveals a wide gene dosage effect. Genes. Chromosomes Cancer 48(7):603-614 (2009).

(Continued)

*Primary Examiner* — Yunsoo Kim

(74) *Attorney, Agent, or Firm* — Wilson Sonsini Goodrich & Rosati

(57) ABSTRACT

Disclosed herein are immunoconjugates comprising a CD46 binding domain and effector agent. Further provided herein are methods of treating cancer comprising administering to a subject having cancer a pharmaceutical composition comprising immunoconjugates comprising a CD46 binding domain and effector agent.

4 Claims, 9 Drawing Sheets

Specification includes a Sequence Listing.

(56) References Cited

U.S. PATENT DOCUMENTS

| | | | |
|---|---|---|---|
| 5,383,851 A | 1/1995 | McKinnon, Jr. et al. |
| 5,386,023 A | 1/1995 | Sanghvi et al. |
| 5,399,163 A | 3/1995 | Peterson et al. |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,428,156 A | 6/1995 | Mease et al. |
| 5,472,693 A | 12/1995 | Gourlie et al. |
| 5,482,856 A | 1/1996 | Fell, Jr. et al. |
| 5,491,088 A | 2/1996 | Hellstrom et al. |
| 5,500,362 A | 3/1996 | Robinson et al. |
| 5,502,167 A | 3/1996 | Waldmann et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,602,240 A | 2/1997 | De Mesmaeker et al. |
| 5,625,126 A | 4/1997 | Lonberg et al. |
| 5,633,425 A | 5/1997 | Lonberg et al. |
| 5,637,684 A | 6/1997 | Cook et al. |
| 5,644,048 A | 7/1997 | Yau |
| 5,661,016 A | 8/1997 | Lonberg et al. |
| 5,700,825 A | 12/1997 | Hofer et al. |
| 5,733,743 A | 3/1998 | Johnson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,831,012 A | 11/1998 | Nilsson et al. |
| 5,849,738 A | 12/1998 | Lee et al. |
| 5,872,107 A | 2/1999 | Schinazi et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,045 A | 8/1999 | Suzuki et al. |
| 5,939,598 A | 8/1999 | Kucherlapati et al. |
| 5,945,439 A | 8/1999 | Richter et al. |
| 5,969,108 A | 10/1999 | McCafferty et al. |
| 6,001,329 A | 12/1999 | Buchsbaum et al. |
| 6,004,533 A | 12/1999 | Collins et al. |
| 6,010,681 A | 1/2000 | Margerum et al. |
| 6,010,682 A | 1/2000 | Unger et al. |
| 6,015,897 A | 1/2000 | Theodore et al. |
| 6,017,522 A | 1/2000 | Butterfield et al. |
| 6,022,522 A | 2/2000 | Sweet et al. |
| 6,022,523 A | 2/2000 | DeGrado et al. |
| 6,022,966 A | 2/2000 | Gustavson et al. |
| 6,028,066 A | 2/2000 | Unger |
| 6,030,840 A | 2/2000 | Mullinax et al. |
| 6,040,498 A | 3/2000 | Stomp et al. |
| 6,045,775 A | 4/2000 | Ericcson et al. |
| 6,045,821 A | 4/2000 | Garrity et al. |
| 6,048,979 A | 4/2000 | Vasilevskis et al. |
| 6,051,207 A | 4/2000 | Klaveness et al. |
| 6,056,939 A | 5/2000 | Desreux et al. |
| 6,060,040 A | 5/2000 | Tournier et al. |
| 6,071,490 A | 6/2000 | Griffiths et al. |
| 6,071,494 A | 6/2000 | Unger |
| 6,075,010 A | 6/2000 | Theodore et al. |
| 6,075,181 A | 6/2000 | Kucherlapati et al. |
| 6,077,499 A | 6/2000 | Griffiths et al. |
| 6,088,613 A | 7/2000 | Unger |
| 6,090,408 A | 7/2000 | Li et al. |
| 6,090,800 A | 7/2000 | Unger et al. |
| 6,093,382 A | 7/2000 | Wedeking et al. |
| 6,096,290 A | 8/2000 | Collins et al. |
| 6,106,866 A | 8/2000 | Ranney |
| 6,114,598 A | 9/2000 | Kucherlapati et al. |
| 6,117,412 A | 9/2000 | Klaveness et al. |
| 6,120,751 A | 9/2000 | Unger |
| 6,120,768 A | 9/2000 | Griffiths et al. |
| 6,123,921 A | 9/2000 | Meade et al. |
| 6,123,923 A | 9/2000 | Unger et al. |
| 6,132,764 A | 10/2000 | Li et al. |
| 6,139,819 A | 10/2000 | Unger et al. |
| 6,143,274 A | 11/2000 | Tweedle et al. |
| 6,143,276 A | 11/2000 | Unger |
| 6,149,890 A | 11/2000 | Uggeri et al. |
| 6,150,584 A | 11/2000 | Kucherlapati et al. |
| 6,153,775 A | 11/2000 | Schroder et al. |
| 6,159,445 A | 12/2000 | Klaveness et al. |
| 6,162,963 A | 12/2000 | Kucherlapati et al. |
| 6,172,197 B1 | 1/2001 | McCafferty et al. |
| 6,177,562 B1 | 1/2001 | Uggeri et al. |
| 6,183,721 B1 | 2/2001 | Albert et al. |
| 6,187,285 B1 | 2/2001 | Meyer et al. |
| 6,190,923 B1 | 2/2001 | Johnson |
| 6,232,068 B1 | 5/2001 | Linsley et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,642,051 B1 | 11/2003 | Lynch et al. |
| 6,669,936 B2 | 12/2003 | Kingsman et al. |
| 6,670,188 B1 | 12/2003 | Vogels et al. |
| 6,815,184 B2 | 11/2004 | Stomp et al. |
| 7,378,504 B2 | 5/2008 | Graziano et al. |
| 7,528,126 B2 | 5/2009 | Howard et al. |
| 8,843,320 B2 | 9/2014 | Shaughnessy et al. |
| 9,567,402 B2 | 2/2017 | Liu |
| 10,533,056 B2 | 1/2020 | Liu et al. |
| 2003/0108966 A1 | 6/2003 | Mather |
| 2007/0031402 A1* | 2/2007 | Zhang .............. A61P 35/00 424/178.1 |
| 2007/0128202 A1 | 6/2007 | Mather |
| 2012/0015906 A1 | 1/2012 | Shaughnessy, Jr. et al. |
| 2014/0205593 A1 | 7/2014 | Huang et al. |
| 2014/0271685 A1 | 9/2014 | Liu |
| 2015/0368352 A1 | 12/2015 | Liu |
| 2016/0032008 A1 | 2/2016 | Zeng et al. |
| 2017/0362330 A1* | 12/2017 | Liu .............. A61P 35/04 |
| 2018/0280532 A1 | 10/2018 | Goldenberg |
| 2019/0276553 A1 | 9/2019 | Liu et al. |
| 2020/0199245 A1 | 6/2020 | Liu et al. |

FOREIGN PATENT DOCUMENTS

| | | |
|---|---|---|
| WO | WO-9311161 A1 | 6/1993 |
| WO | WO-9312227 A1 | 6/1993 |
| WO | WO-9411026 A2 | 5/1994 |
| WO | WO-9413804 A1 | 6/1994 |
| WO | WO-9425585 A1 | 11/1994 |
| WO | WO-9515335 A2 | 6/1995 |
| WO | WO-9617958 A1 | 6/1996 |
| WO | WO-9713852 A1 | 4/1997 |
| WO | WO-9824884 A1 | 6/1998 |
| WO | WO-9945962 A1 | 9/1999 |
| WO | WO-9955720 A1 | 11/1999 |
| WO | WO-0114424 A2 | 3/2001 |
| WO | WO-0243478 A2 | 6/2002 |
| WO | WO-03032814 A2 | 4/2003 |
| WO | WO-2007059782 A1 | 5/2007 |
| WO | WO-2009039192 A2 | 3/2009 |
| WO | WO-2012031273 A2 | 3/2012 |
| WO | WO-2015105995 A2 | 7/2015 |
| WO | WO-2016019300 A1 | 2/2016 |
| WO | WO-2016040683 A1 | 3/2016 |
| WO | WO-2016042461 A1 | 3/2016 |
| WO | WO-2016100985 A2 | 6/2016 |
| WO | WO-2018089807 A2 | 5/2018 |
| WO | WO-2018089829 A1 | 5/2018 |
| WO | WO-2022032020 A1 | 2/2022 |

OTHER PUBLICATIONS

Al-Hujaily et al., Development of novel immunotherapies for multiple myeloma. International Journal of Molecular Sciences 17(9):E1506 (2016).

Al-Lazikani et al. Standard conformations for the canonical structures of immunoglobulins. J. Mol Biology 273(4):927-948 (1997).

(56) References Cited

OTHER PUBLICATIONS

Almagro et al. Humanization of antibodies. Front Biosci 13:1619-1633 (2008).
Altschul et al. Basic Local Alignment Search Tool. J. Mol. Biol. 215: 403-410 (1990).
Altschul, et al. Gapped BLAST and PSI-BLAST: a new generation of protein database search programs. Nucleic Acids Res 25:3389-3402 (1997).
Angerer et al. Demonstration of tissue-specific gene expression by in situ hybridization. Methods Enzymol 152:649-660 (1987).
Axup et al. Synthesis of site-specific antibody-drug conjugates using unnatural amino acids. PNAS 109(40):16101-16106 (2012).
Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).
Barany et al. The Peptide: Analysis Synthesis, Biology, editors E. Gross and J. Meienhofer. Academic Press, New York (1980) Chapter 1(vol. 2):3-254.
Barbas et al. Recognition of DNA by Synthetic Antibodies. J Am. Chem. Soc., 116:2161-2162 (1994).
Barringer et al. Blunt-end and single-strand ligations by *Escherichia coli* ligase: influence on an in vitro amplification scheme. Gene 89(1):117-22 (1990).
Beaucage et al. Deoxynucleoside phosphoramidites—A new class of key intermediates for deoxypolynucleotide synthesis. Tetra. Lett. 22:1859-1862 (1981).
Beaucage et al. The Functionalization of Oligonucleotides Via Phosphoramidite Derivative. Tetrahedron Report No. 329. 49(10):1925-1963 (1993).
Beiboer, Sigrid H. et al. Guided Selection of a Pan Carcinoma Specific Antibody Reveals Similar Binding Characteristics yet Structural Divergence Between the Original Murine Antibody and its Human Equivalent. J. Mol. Biol. 296:833-849 (2000).
Biran et al. Patients with newly diagnosed multiple myeloma and chromosome 1 amplification have poor outcomes despite the use of novel triplet regimens. Am. J. Hematol. 89(6):616-620 (2014).
Bird et al. Single-chain antigen-binding proteins. Science 242:423-442 (1988).
Birkle et al. Role of tumor-associated gangliosides in cancer progression. Biochimie 85:455-463 (2003).
Bloeman et al. Adhesion molecules: a new target for immunoliposome-mediated drug delivery. FEBS Lett. 357:140 (1995).
Boeggeman et al. Site specific conjugation of fluoroprobes to the remodeled Fc N-glycans of monoclonal antibodies using mutant glycosyltransferases: application for cell surface antigen detection. Bioconjug. Chem. 20:1228-1236 (2009).
Bonifant et al., Toxicity and management in CAR T-cell therapy. Molecular Therapy—Oncolytics 3:16011 (2016).
Borchardt et al. Targeted actinium-225 in Vivo Generators for Therapy of Ovarian Cancer Cancer Res. 63:5084-50 (2003).
Borlinghaus et al. Radiosensitizer Conjugation to the Carcinoma 19-9 Monoclonal Antibody. Cancer Research 47(15):4071-4075 (Aug. 1, 1987).
Boswell et al. Differential Effects of Predosing on Tumor and Tissue Uptake of an 111In-Labeled Anti-TENB2 Antibody-Drug Conjugate. Soc. Nuclear Med. 53:1454-1461 (2012).
Boswell et al. Impact of Drug Conjugation on Pharmacokinetics and Tissue Distribution of Anti-STEAP1 Antibody-Drug Conjugates in Rats. Bioconjug Chem. 22(10):1994-2004 (2011).
Boulianne et al. Production of functional chimaeric mouse/human antibody. Nature 312:643 (1984).
Brill et al. Synthesis of Oligodeoxynucleoside Phosphorodithioatesvia Thioamidites. J Am Chem Soc 111:2321 (1989).
Briscoe et al. Delivery of superoxide dismutase to pulmonary epithelium via pH-sensitive liposomes. Am. J. Physiol. 1233:134 (1995).
Brown et al. Chemical synthesis and cloning of a tyrosine tRNA gene. Methods Enzymol. 68:109-51 (1979).
Brummell et al.: Probing the Combining Site of an Anti-Carbohydrate Antibody by Saturation-Mutagenesis: Role of the Heavy-Chain CDR3 Residues; Biochemistry 32: 1180-1187 (1993).
Buchner et al.: A method for increasing the yield of properly folded recombinant fusion proteins: single-chain immunotoxins from renaturation of bacterial inclusion bodies. Anal. Biochem. 205(2):263-270 (1992).
Burks et al.: In vitro scanning saturation mutagenesis of an antibody binding pocket; Proc. Natl. Acad. Sci. USA (94) pp. 412-417 (1997).
Caban et al. Size matters: a view of selenocysteine incorporation from the ribosome. Cell Mol. Life Sci. 63:73-81 (2006).
Cai et al. Anti-melanoma antibodies from melanoma patients immunized with genetically modified autologous tumor cells: selection of specific antibodies from single-chain Fv fusion phage libraries. PNAS USA 92:6537-6541 (1995).
Carlsson et al. Screening for genetic mutations. Nature 380:207 (1996).
Caron et al., Engineered humanized dimeric forms of IgG are more effective antibodies. J. Exp Med. 176:1191-1195 (1992).
Chaudhary et al. A proper amino terminus of diphtheria toxin is important for cytotoxicity. Bioch. Biophys. Res. Comm. 180:545-551 (1991).
Chaudhary et al. Activity of a recombinant fusion protein between transforming growth factor type alpha and Pseudomonas toxin. PNAS USA 84:4538-4542 (1987).
Chee et al. Accessing genetic information with high-density DNA arrays. Science 274:610-614 (1996).
Cheung et al. Epitope-specific antibody response to the surface antigen of duck hepatitis B virus in infected ducks. Virology 176(2):546-552 (1990).
Choileain et al. The dynamic processing of CD46 intracellular domains provides a molecular rheostat for T cell activation. PLoS One 6(1): e16287 (2011).
Chotha et al. Structural repertoire of the human VH segments. J.Mol.Biol. 227:799-817 (1992).
Chothia et al. Canonical structures for the hypervariable regions of immunoglobulins. J Mol Biol 196:901-917 (1987).
Chothia et al. The predicted structure of immunoglobulin D1.3 and its comparison with the crystal structure. Science 233:755-8 (1986).
Clackson et al. A hot spot of binding energy in a hormone-receptor interface. Science 267:383-386 (1995).
Clackson et al. Making antibody fragments using phage display libraries. Nature 352(6336):624-628 (1991).
Clynes et al. Inhibitory Fc receptors modulate in vivo cytotoxicity against tumour targets. Nat Med. 6(4):443-6. (Apr. 2000).
Colbere-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Commisso et al. Macropinocytosis of protein is an amino acid supply route in Ras-transformed cells. Nature 497:633-637 (2013).
Connor et al. Monoclonal antibody and liposomes. Pharm. Ther., 28:341-365 (1985).
Conrad et al. Compartment-specific accumulation of recombinant immunoglobulins in plant cells: an essential tool for antibody production and immunomodulation of physiological functions and pathogen activity. Plant Mal. Biol. 38:101-109 (1998).
Cramer et al. Transgenic plants for therapeutic proteins: linking upstream and downstream strategies. Curr. Top. Microbol. Immunol. 240:95-118 (1999).
Crimeen-Irwin et al. Ligand binding determines whether CD46 Is internalized by clathrin-coated pits or macropinocytosis. The Journal of Biological Chemistry 278(47): 46927-46937 (2003).
Crouse et al. Expression and amplification of engineered mouse dihydrofolate reductase minigenes. Mol Cell Biol 3(2):257-266 (1983).
De Jong et al., Drug delivery and nanoparticles: applications and hazards. International Journal of Nanomedicine 3:133-149 (2008).

(56) References Cited

OTHER PUBLICATIONS

De Kruif et al. Rapid selection of cell subpopulation-specific human monoclonal antibodies from a synthetic phage antibody library. PNAS USA 92:3938-3942 (1995).
De Mesmaeker et al. Comparison of Rigid and Flexible Backbones in Antisense Oligonucleotides Bioorg Med Chem Lett 4(3):395-398 (1994).
Dempcy et al. Synthesis of a thymidyl pentamer of deoxyribonucleic guanidine and binding studies with DNA homopolynucleotides. PNAS USA 92:6097-6101 (1995).
Ditzel et al. Determinants of polyreactivity in a large panel of recombinant human antibodies from HIV-1 infection. J Immunol. 157:739-749 (1996).
Edelman et al. The covalent structure of an entire yGimmunoglobulin molecule. PNAS 63(1):78-85 (1969).
Egholm et al. Peptide Nucleic Acids (PNA) Oligonucleotide Analogues with an Achiral Peptide Backbone. J Am Chem Soc 114:1895-1897 (1992).
Fan et al. Noninvasive diagnosis of fetal aneuploidy by shotgun sequencing DNA from maternal blood. PNAS 105:16266-16271 (2008).
Fortina, et al. Digital mRNA profiling. Nat Biotechnol. Mar. 2008;26(3):293-4.
Fuh et al. Structure-function studies of two synthetic anti-vascular endothelial growth factor Fabs and comparison with the Avastin Fab. J Biol. Chem. 281:6625-6631 (2006).
Gao et al. De novo identification of tumor-specific internalizing human antibody-receptor pairs by phage-display methods. J Immunol Meth 274:185-197 (2003).
Gao et al. Unusual conformation of a 3'-thioformacetal linkage in a DNA duplex. J. Biomolecular NMR.34:17-34 (1994).
Geuijen et al. A proteomic approach to tumour target identification using phage display, affinity purification and mass spectrometry. Eur. J. Cancer 41:178-187 (2005).
Geuijen et al. Affinity ranking of antibodies using flow cytometry: application in antibody phage display-based target discovery. Journal of Immunological Methods 302(1): 68-77 (2005).
Gibson et al. A novel method for real time quantitative RT-PCR. Genome Research 6:995-1001 (1996).
Goding. Monoclonal AntibodiesPrinciples and Practice, pp. 59-103 (Academic Press) (1986).
Goldspiel et al. Human gene therapy. Clin Pharm 12:488-505 (1993).
Guatelli et al. Isothermal, in vitro amplification of nucleic acids by a multienzyme reaction modeled after retroviral replication. PNAS USA 87(5):1874-1878 (1990).
Ha et al. High-content analysis of antibody phage-display library selection outputs identifies tumor selective macropinocytosis-dependent rapidly internalizing antibodies. Mol. Cell Proteomics. 13(12):3320-3331 (2014).
Hakomori et al. Tumor-associated carbohydrate antigens defining tumor malignancy: basis for development of anti-cancer vaccines. Adv. Exp. Med. Biol. 491:369-402 (2001).
Hall et . al. A single amino acid mutation in CDR3 of the 3-14-9 L chain abolished expression of the IDA 10-defined idiotope and antigen bindingJ Immunol. 149:1605-1612 (1992).
Hanamura et al., Frequent gain of chromosome band 1q21 in plasma-cell dyscrasias detected by fluorescence in situ hybridization: incidence increases from MGUS to relapsed myeloma and is related to prognosis and disease progression following tandem stem-cell transplantation. Blood 108:1724-1732 (2006).
Hanes et al. In vitro selection and evolution of functional proteins by using ribosome display. PNAS USA 94:4937-4942 (1997).
Hanisch. O-Glycosylation of the mucin type. Biol. Chem. 382:143-149 (2001).
Haraldsdottir et al., Integrating anti-EGFR therapies in metastatic colorectal cancer. Journal of Gastrointestinal Oncology 4(3):285-298 (2013).
Harding et al. Class switching in human immunoglobulin transgenic mice. Ann. NY Acad. Sci. 764:536-546 (1995).

He et al. Targeting Prostate Cancer Cells In Vivo Using a Rapidly Internalizing Novel Human Single-Chain Antibody Fragment. J Nucl Med 51(3):427-432 (2010).
Heeley, et al. Mutations flanking the polyglutamine repeat in the modulatory domain of rat glucocorticoid receptor lead to an increase in affinity for hormone. Endocr Res. Aug. 2002;28(3):217-29.
Heid et al. Real time quantitative PCR. Genome Res. 6(10):986-994 (1996).
Hoet et al. Generation of high-affinity human antibodies by combining donor-derived and synthetic complementarity-determining-region diversity. Nature Biotechnology 23(3):344-348 (Mar. 2005).
Hofer et al. Molecularly defined antibody conjugation through a selenocysteine interface. Biochem. 48:12047-12057 (2009).
Holliger et al. "Diabodies": small bivalent and bispecific antibody fragments. PNAS USA 90(14):6444-6448 (1993).
Honegger et al. Yet another numbering scheme for immunoglobulin variable domains: an automatic modeling and analysis tool. J Mol Biol 309(3):657-70 (2001).
Hood et al. Molecular farming of industrial proteins from transgenic maize. Adv. Exp. Med. Biol. 464:127-147 (1999).
Hoogenboom et al. Multi-subunit proteins on the surface of filamentous phage: methodologies for displaying antibody (Fab) heavy and light chains. Nucleic Acids Res. 19(15):4133-4137 (1991).
Horn et al. Oligonucleotides with Alternating Anionic and Cationic Phosphoramidate Linkages: Synthesis and Hybridization of Sterouniform Isomers. Tetrahedron Letters 37(6):743-746 (1996).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Jahn et al. Expression of monovalent fragments derived from a human IgM autoantibody in *E. coli*. The input of the somatically mutated CDR1/CDR2 and of the CDR3 into antigen binding specificity. Immunobiol. 193:400-419 (1995).
Jeger et al. Site-specific and stoichiometric modification of antibodies by bacterial transglutaminase. Ange Chem Int. Ed. Engl 49:9995-9997 (2010).
Jenkins et al. The Biosynthesis of Carbocyclic Nucleosides. Chemical society reviews 24:169-176 (1995).
Jones et al. Replacing the complementarity-determining regions in a human antibody with those from a mouse. Nature 321:522-525 (1986).
Jung et al. Hybridization of Alternating Cationic/Anionic Oligonucleotides to RNA Segments. Nucleosides & Nucleotides 13(6 &7):1597-1605 (1994).
Junutula et al. Rapid identification of reactive cysteine residues for site-specific labeling of antibody—Fabs. J. Immunol. Meth. 332:41-52 (2008).
Kabat et al. Sequences of proteins of immunological interest. NIH Publ. No. 91-3242 1:647-669 (1991).
Kiedrowshi et al. Parabolic Growth of a Self-Replicating Hexadeoxynucleotide Bearing a 3'-5'-Phosphoamidate Linkage Angew. Chem. Intl. Ed. English 30(4):423-426 (1991).
Kiick et al. Incorporation of azides into recombinant proteins for chemoselective modification by the Staudinger ligation. PNAS 99:1:19-24 (2002).
Kirkland et al. Analysis of the fine specificity and cross-reactivity of monoclonal anti-lipid A antibodies. J Immunol. 137(11):3614-3619 (1986).
Klimka, A. et al. Human anti-CD30 recombinant antibodies by guided phage antibody selection using cell panning. British Journal of Cancer 83(2):252-260 (2000).
Kobata et al. Altered glycosylation of proteins produced by malignant cells, and application for the diagnosis and immunotherapy of tumours. Immunol. Cell Biol. 83:429-439 (2005).
Kobayashi et al.: Tryptophan H33 plays an important role in pyrimidine (6-4) pyrimidone photoproduct binding by a high-affinity antibody; Protein Engineering 12(10) 879-884 (1999).
Kohler et al. Continuous cultures of fused cells secreting antibody of predefined specificity. Nature 256:495-497 (1975).

(56) References Cited

OTHER PUBLICATIONS

Kozbor et al. The production of monoclonal antibodies from human lymphocytes. Immunology Today 4:72-79 (1983).
Kreitman et al.: Purification and characterization of IL6-PE4E, a recombinant fusion of interleukin 6 with Pseudomonas exotoxin. Bioconjug Chem. 4(6):581-5 (1993).
Kryukov et al. Characterization of mammalian selenoproteomes. Science 300:1439-1443 (2003).
Kuroiwa et al. Cloned transchromosomic calves producing human immunoglobulin. Nat Biotechnol 20:889-894 (2002).
Kutmeier et al. Assembly of humanized antibody genes from synthetic oligonucleotides using a single-round PCR. BioTechniques 17:242 (1994).
Kwoh et al. Transcription-based amplification system and detection of amplified human immunodeficiency virus type 1 with a bead-based sandwich hybridization format. PNAS USA 86:1173-1177 (1989).
Landegren et al. A Ligase-Mediated Gene Detection Technique. Science 241:1077-1080 (1988).
Le Friec et al. The CD46-Jagged1 interaction is critical for human TH1 immunity. Nat Immunol 13(12):1213-1221 (2012).
Lefranc et al. IMGT, the International ImMunoGeneTics Database. Nucleic Acids Res. 27:209-212 (1999).
Lefranc et al. IMGT unique numbering for immunoglobulin and T cell receptor variable domains and Ig superfamily V-like domains. Dev Comp Immunol 27(1):55-77 (2003).
Lefranc. The IMGT unique numbering for immunoglobulins, T-cell receptors, and Ig-like domains. The Immunologist 7:132-136 (1999).
Lekkerkerker et al. Chapter 2A: Phage antibodies against human dendritic cell subpopulations obtained by flow cytometry-based selection on freshly isolated cells. J. Immunol. Methods 231:53-63 (1972).
Letsinger et al. Cationic Oligonucleotides. J Am Chem Soc 110:4470-4471 (1988).
Letsinger et al. Effects of pendant groups at phosphorus on binding properties of d-ApA analogues. Nucleic Acids Research 14(8):3487-3499 (1986).
Letsinger et al. Phosphoramidate Analogs of Oligonucleotides. J Org Chem 35(11):3800-3803 (1970).
Lewis et al. A Facile, Water-Soluble Method for Modification of Proteins with DOTA. Use of Elevated Temperature and Optimized pH To Achieve High Specific Activity and High Chelate Stability in Radiolabeled Immunoconjugates. Bioconjugate Chem. 5:565-576 (1994).
Liljebla et al. Analysis of agalacto-IgG in rheumatoid arthritis using surface plasmon resonance. Glycoconj J. 17(5):323-9 (2000).
Liu et al. Applying Phage Antibodies to Proteomics: Selecting Single Chain Fv Antibodies to Antigens Blotted on Nitrocellulose. Anal. Biochem. 286:119-128 (2000).
Liu et al. Genetic incorporation of unnatural amino acids into proteins in mammalian cells. Nat. Meth. 4:239-244 (2007).
Liu et al. Mapping Tumor Epitope Space by Direct Selection of Single-Chain Fv Antibody Libraries on Prostate Cancer Cells. Cancer Research 64(2):704-710 (2004).
Liu et al. Towards proteome-wide production of monoclonal antibody by phage display. J Mol Biol. 315(5):1063-1073 (2002).
Lonberg, et al. Antigen-specific human antibodies from mice comprising four distinct genetic modifications. Nature. Apr. 28, 1994;368(6474):856-9.
Lonberg et al. Human antibodies from transgenic mice. Int Rev Immunol. 13(1):65-93 (1995).
Lowman et al. Affinity maturation of human growth hormone by monovalent phage display. J Mal. Biol. 234:564-578 (1993).
Lowy et al., Isolation of transforming DNA: Cloning the hamster aprt gene. Cell 22:817-823 (1980).
Lundblad et al. Molecular 'pharming'. Biotechnol. Appl. Biochem. 30:99-108 (1999).
Ma et al. Immunotherapeutic potential of antibodies produced in plants. Trends Biotechnol. 13:522-527 (1995).
Ma et al. Plant antibodies for immunotherapy. Plant Physiol. 109:341-346 (1995).
Maccallum et al. Antibody-antigen interactions: contact analysis and binding site topography. J Mol Biol. 262(5):732-745 (1996).
Mag et al. Synthesis and selective cleavage of an oligodeoxynucleotide containing a bridged internucleotide 5'-phosphorothioate linkage. Nucleic Acids Research 19(7):1437-1441 (1991).
Mantaj et al., Covalent bonding of pyrrolobenzodiazepines (PBDs) to terminal guanine residues within duplex and hairpin DNA fragments. PLoS One. 11(4):e0152303 (2016).
Marks et al. By-passing immunization: building high affinity human antibodies by chain shuffling. Biotechnology (NY) 10(7):779-783 (1992).
Marks et al. By-passing immunization: Human antibodies from v-gene libraries displayed on phage. J. Mol. Biol. 222:581-597 (1991).
Marks et al. Molecular evolution of proteins on filamentous phage. Mimicking the strategy of the immune system. J. Biol. Chem. 267:16007-16010 (1992).
Martin. Chapter 31. Protein Sequence and Structure Analysis of Antibody Variable Domains. in Antibody Engineering, Kontermann and Dübel, eds., pp. 422-439, Springer-Verlag, Berlin (2001).
McCafferty et al. Phage Antibodies: Filamentous Phage Displaying Antibody Variable Domains. Nature 348:552-554 (1990).
McDevitt et al. Tumor Therapy With Targeted Atomic Nanogenerators. Science 294:1537-1540 (2001).
McDonagh et al. Engineered anti-CD70 antibody-drug conjugate with increased therapeutic index. Mol Cancer Ther 7:2913-2923 (2008).
McWhirter et al. Antibodies selected from combinatorial libraries block a tumor antigen that plays a key role in immunomodulation. PNAS USA 103(4):1041-1046 (2006).
Meier et al. Peptide Nucleic Acids (PNAs)—Unusual Properties of Nonionic Oligonucleotide Analogues. Angew. Chem. Int. Ed. Engl. 31(8):1008-1010 (1992).
Merrifield et al. Solid Phase Peptide Synthesis I. J Am Chem Soc 85:2149-2154 (1963).
Meyers et al. Optimal alignments in linear space. CABIOS 4:11-17 (1989).
Mian et al. Structure, function and properties of antibody binding sites. J. Mol. Biol. 217:133-151 (1991).
Moldenhauer, et al. Identity of HML-1 antigen on intestinal intraepithelial T cells and of B-ly7 antigen on hairy cell leukaemia. Scand J Immunol. 32(2):77-82 (Aug. 1990).
Morel et al. Monoclonal antibodies to bovine serum albumin: Affinity and specificity determinations. Mol Immunol. 25(1):7-15 (1988).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Munson et al. Ligand: a versatile computerized approach for characterization of ligand-binding systems. Anal Biochem. 107(1):220-239 (Sep. 1, 1980).
Narang et al. [6] Improved phosphotriester method for the synthesis of gene fragments. Meth. Enzymol. 68:90-99 (1979).
Needleman et al. A general method applicable to the search for similarities in the amino acid sequence of two proteins. Journal of molecular biology 48(3):443-453 (1970).
Nemec et al. Gain of 1q21 is an unfavorable genetic prognostic factor for multiple myeloma patients treated with high-dose chemotherapy. Biol Blood Marrow Transplant 16:548-554 (2010).
Neuberger et al. Recombinant antibodies possessing novel effector functions. Nature 312(5995):604-608 (1984).
Nielsen et al. Advances in targeted delivery of small interfering RNA using simple bioconjugates. Expert Opinion On Drug Delivery 11(5):791-822 (2014).

(56) References Cited

OTHER PUBLICATIONS

Nielsen et al. PNA hybridizes to complementary oligonucleotides obeying the Watson-Crick hydrogen bonding rules. Letter to Nature 365:566-568 (1993).
Nielsen et al., Therapeutic efficacy of anti-ErbB2 immunoliposomes targeted by a phage antibody selected for cellular endocytosis. Biochim Biophys Acta 1591:109-118 (2002).
Nord et al. Binding proteins selected from combinatorial libraries of an alpha-helical bacterial receptor domain. Nat. Biotechnol. 15:772-777 (1997).
O'Hare et al. Transformation of mouse fibroblasts to methotrexate resistance by a recombinant plasmid expressing a prokaryotic dihydrofolate reductase. PNAS USA 78:1527-1531 (1981).
Owais et al. Chloroquine encapsulated in malaria-infected erythrocyte-specific antibody-bearing liposomes effectively controls chloroquine-resistant Plasmodium berghei infections in mice. Antimicrob. Agents Chemother. 39:180-184 (1995).
Pastinen et al. Minisequencing: a specific tool for DNA analysis and diagnostics on oligonucleotide arrays. Genome Res. 7:606-614 (1997).
Pauwels et al. Biological activity of new 2-5A analogues. Chemica scripta 26:141-145 (1986).
PCT/US2015/049492 International Search Report and Written Opinion dated Nov. 17, 2015.
PCT/US2017/061124 International Search Report and Written Opinion dated May 11, 2018.
PCT/US2017/061124 Invitation to Pay Additional Fees dated Feb. 12, 2018.
Pini et al. Design and use of a phage display library. Human antibodies with subnanomolar affinity against a marker of angiogenesis eluted from a two-dimensional gel. J. Biol. Chem. 273: 21769-21776 (1998).
Pinkel et al. High resolution analysis of DNA copy number variation using comparative genomic hybridization to microarrays. Nat Genet 20:207-211 (1998).
Pirollo et al. Tumor-targeting nanoimmunoliposome complex for short interfering RNA delivery. Hum. Gene Ther. 17:117-124 (2006).
Pollack et al. Genome-wide analysis of DNA copy-number changes using cDNA microarrays. Nat. Genet. 23(1):41-6 (1999).
Polymenis et al. Critical binding site amino acids of anti-Z-DNA single chain Fv molecules. Role of heavy and light chain CDR3 and relationship to autoantibody activity. J Immunol. 152:5318-5329 (1994).
Poul et al. Selection of tumor-specific internalizing human antibodies from phage libraries. J. Mol. Biol. 301:1149-1161 (2000).
Qasba et al. Substrate-induced conformational changes in glycosyltransferases. Trends Biochem. Sci. 30:53-62 (2005).
Queen et al. A humanized antibody that binds to the interleukin 2 receptor. PNAS USA 86:10029-10032 (1989).
Rader et al. A phage display approach for rapid antibody humanization: Designed combinatorial V gene libraries. PNAS USA 95(15): 8910-8915 (Jul. 21, 1998).
Ramakrishnan et al. Structure-based design of beta 1,4-galactosyltransferase I (beta 4Gal-T1) with equally efficient N-acetylgalactosaminyltransferase activity: point mutation broadens beta 4Gal-T1 donor specificity. J. Biol. Chem. 277:20833-20839 (2002).
Ranade. Drug delivery systems. 1. site-specific drug delivery using liposomes as carriers. J. Clin. Pharmacol. 29:685 (1989).
Rawls. Optimistic About Antisense. C&E News Washington (pp. 35-39) (Jun. 2, 1997).
Reiter et al. Disulfide stabilization of antibody Fv: computer predictions and experimental evaluation. Protein Eng. 8:1323-1331 (1995).
Reyes-Reyes et al. A new paradigm for aptamer therapeutic AS1411 action: uptake by macropinocytosis and its stimulation by a nucleolin-dependent mechanism. Cancer Research 70(21):8617-8629 (2010).
Riechmann et al., "Reshaping human antibodies for therapy," Nature 332:323-327 (1988).
Ronnmark et al. Human immunoglobulin A (IgA)-specific ligands from combinatorial engineering of protein A. Eur. J Biochem., 269:2647-2655 (2002).
Sahagan et al. A genetically engineered murine/human chimeric antibody retains specificity for human tumor-associated antigen. J Immunol. 137:1066 (1986).
Santerre et al. Expression of prokaryotic genes for hygromycin B and G418 resistance as dominant-selection markers in mouse L cells. Gene 30(1-3):147-156 (1984).
Sawai et al. Synthesis and Properties of Oligoadenylic Acids Containing 2'-5' Phosphoramide Linkage. Chem. Lett. 13(5):805-808 (1984).
Schier et al. Efficient in vitro affinity maturation of phage antibodies using BIAcore guided selections. Human Antibodies and Hybridomas. 7:97-105 (1996).
Schier, et al. Identification of functional and structural amino-acid residues by parsimonious mutagenesis. Gene. 169(2):147-155 (Mar. 9, 1996).
Schier et al., Isolation of picomolar affinity anti-c-erbB-2 single-chain Fv by molecular evolution of the complementarity determining regions in the center of the antibody binding site. J Mol Biol. 263(4):551-567 (1996).
Schweizer et al., Controlled release of therapeutic antibody formats. European Journal of Pharmaceutics and Biopharmaceutics 88(2):291-309 (2014).
Sharon et al. Expression of a VHC kappa chimaeric protein in mouse myeloma cells. Nature 309:364 (1984).
Sharon et al. Recombinant poly-clonal antibodies for cancer therapy. J. Cell. Biochem. 96:305-313 (2005).
Shen et al. Conjugation site modulates the in vivo stability and therapeutic activity of antibody-drug conjugates. Nat Biotechnol. 22;30(2):184-9 (2012).
Sherbenou et al. Antibody-drug conjugate targeting CD46 eliminates multiple myeloma cells. J Clin Invest 126:4640-4653 (2016).
Sherbenou et al. CD46 Is Amplified in High-Risk Myeloma with Gain of Chromosome Iq and Selectively Targeted By a Novel Anti-CD46 Antibody-Drug Conjugate. Blood 128:384 (2016).
Shopes. A genetically engineered human IgG mutant with enhanced cytolytic activity. J. Immunol. 148: 2918-2922 (1992).
Siegall et al. Cytotoxic activities of a fusion protein comprised of TGF alpha and Pseudomonas exotoxin. Faseb J. 3:2647-2652 (1989).
Siegall et al. Functional Analysis of Domains II, Ib, and III of Pseudomonas Exotoxin. J Biol Chem 264(24):14256-14261 (Aug. 25, 1989).
Silacci et al. Design, construction, and characterization of a large synthetic human antibody phage display library. Proteomics 5:2340-2350 (2005).
Skerra et al. Assembly of a functional Immunoglobulin Fv fragment in *Escherichia coli*. Science 240(4855):1038-1041 (1988).
Song et al. Antibody mediated in vivo delivery of small interfering RNAs via cell-surface receptors. Nat. Biotechnol. 23:709-717 (2005).
Sprinzl et al. Enzymatic Incorporation of ATP and CTP Analogues into the 3' End of tRNA. Eur J Biochem 81:579-589 (1977).
Stahli et al. Distinction of epitopes by monoclonal antibodies. Methods in Enzymology 92:242-253 (1983).
Stevenson et al. A chimeric antibody with dual Fc regions (bisFabFc) prepared by manipulations at the IgG hinge. Anti-Cancer Drug Design 3:219-230 (1989).
Strejan et al. Suppression of chronic-relapsing experimental allergic encephalomyelitis in strain-13 guinea pigs by administration of liposome-associated myelin basic protein. J Neuroimmunol 7:27 (1984).
Strop et al. Location matters: site of conjugation modulates stability and pharmacokinetics of antibody drug conjugates. Chem Biol 20(2):161-167 (2013).
Su et al. Targeting CD46 for both adenocarcinoma and neuroendocrine prostate cancer. JCI Insight. 3(17):e121497 (2018).
Sunbul et al. Site specific protein labeling by enzymatic post-translational modification. Org. Biomol. Chem. 7:3361-3371 (2009).
Sutherland et al. Lysosomal trafficking and cysteine protease metabolism confer target-specific cytotoxicity by peptide-linked anti-CD30-auristatin conjugates. J Biol. Chem. 281:10540-10547 (2006).

(56) References Cited

OTHER PUBLICATIONS

Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Tan et al. A human-mouse chimeric immunoglobulin gene with a human variable region is expressed in mouse myeloma cells. J Immunol. 135:3564-3567 (1985).
Thorpe et al. Monoclonal Antibodies in Clinical Medicine, Academic Press, pp. 168-190 (1982).
Tolstoshev. Gene Therapy, Concepts, Current Trials and Future Directions. Ann. Rev. Pharmacol. Toxicol. 32:573-596 (1993).
Tomizuka et al. Double trans-chromosomic mice: maintenance of two individual human chromosome fragments containing Ig heavy and kappa loci and expression of fully human antibodies. PNAS USA 97:722-727 (2000).
Tramontano et al. Framework Residue 71 Is a Major Determinant of the Position and Conformation of the Second Hypervariable Region in the VH Domains of Immunoglobulins. J. Mol. Biol. 215(1):175-82 (1990).
Uchida et al. Diphtheria toxin and related proteins. I. Isolation and properties of mutant proteins serologically related to diphtheria toxin. J Biol. Chem., 248:3838-3844 (1973).
Uchida et al. Reconstitution of diphtheria toxin from two nontoxic cross-reacting mutant proteins. Science 175:901-903 (1972).
Ugorski et al. Sialyl Lewis(a): a tumor-associated carbohydrate antigen involved in adhesion and metastatic potential of cancer cells. Acta Biochim. Pol. 49(2):303-311 (2002).
Umezawa et al. Liposome targeting to mouse brain: mannose as a recognition marker. Biochem. Biophys. Res. Commun. 153:1038 (1988).
U.S. Appl. No. 15/508,059 Office Action dated May 30, 2019.
U.S. Appl. No. 15/508,059 Office Action dated Sep. 7, 2018.
U.S. Appl. No. 16/348,135 Office Action dated Apr. 13, 2021.
Van Der Neut Kolfschoten et al. Anti-inflammatory activity of human IgG4 antibodies by dynamic Fab arm exchange. Science 317:1554-1557 (2007).
Vitetta et al. Redesigning nature's poisons to create anti-tumor reagents. Science 238(4830):1098-1104 (1987).
Von Kiedrowski et al. Parabolic Growth of a Self-Replicating Hexadeoxy nucleotide Bearing a 3'-5'-Phosphaomidate Linkage. Angew. Chem. Int. Ed. Engl 30(4):423-426 (1991).
Waldmann. Monoclonal antibodies in diagnosis and therapy. Science 252:1657-1662 (1991).
Wan et al. Cloning differentially expressed mRNAs. Nat Biotechnol 14:1685-91 (1996).
Wang et al. Addition of the keto functional group to the genetic code of *Escherichia coli*. PNAS USA 100:56-61 (2003).
Wang et al., Clinical manufacturing of CAR T cells: foundation of a promising therapy. Molecular Therapy—Oncolytics 3:16015 (2016).
Ward et al. Binding activities of a repertoire of single immunoglobulin variable domains secreted from *Escherichia coli*. Nature 341(6242):544-546 (1989).
Waterhouse et al. Combinatorial infection and in vivo recombination: a strategy for making large phage antibody repertoires. Nucleic Acids Res. 21(9):2265-2266 (May 11, 1993).
Wells. Additivity of mutational effects in proteins. Biochemistry. 29(37): 8509-8517 (1990).
Whitelam et al. Antibody production in transgenic plants. Biochem. Soc. Trans. 22:940-944 (1994).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Williams et al. Structure/function analysis of interleukin-2-toxin (DAB486-IL-2). Fragment B sequences required for the delivery of fragment A to the cytosol of target cells. J Biol. Chem. 265:11885-11889 (1990).
Wolff, et al. Monoclonal antibody homodimers: enhanced antitumor activity in nude mice. Cancer Res. Jun. 1, 1993;53(11):2560-5.
Wu et al. Delivery systems for gene therapy. Biotherapy 3:87-95 (1991).
Wu et al. Investigations of N-linked macrocycles for 111In and 90Y labeling of proteins. Int J Rad Appl Instrum B 19(2):239-244 (1992).
Wu et al. The ligation amplification reaction (LAR)—amplification of specific DNA sequences using sequential rounds of template-dependent ligation. Genomics 4:560 (1989).
Yokoyama et al. Properties and applications of microbial transglutaminase. Appl. Microbial. Biotechnol. 64:447-454 (2004).
Young et al. An enhanced system for unnatural amino acid mutagenesis in *E. coli*. J Mol Biol 395(2):361-374 (2010).
Yu et al. The amplification of 1q21 is an adverse prognostic factor in patients with multiple myeloma in a Chinese population. Onco Targets Ther 9:295-302 (2016).
Zhan et al. Gene-expression signature of benign monoclonal gammopathy evident in multiple myeloma is linked to good prognosis. Blood 109(4):1692-1700 (2007).
Zhan et al. Global gene expression profiling of multiple myeloma, monoclonal gammopathy of undetermined significance, and normal bone marrow plasma cells. Blood 99(5):1745-1757 (2002).
PCT/US2017/061153 International Search Report and Written Opinion dated Mar. 27, 2018.
PCT/US2017/061153 Invitation to Pay Additional Fees dated Jan. 26, 2018.
Acchione et al. Impact of linker and conjugation chemistry on antigen binding, Fc receptor binding and thermal stability of model antibody-drug conjugates. mAbs 4:362-372 (2012).
Adem et al. Auristatin antibody drug conjugate physical instability and the role of drug payload. Bioconjug Chem. 25(4):656-64 (2014).
Badescu et al. Bridging disulfides for stable and defined antibody drug conjugates. Bioconjugate Chemistry 25:1124-1136 (2014).
Frka-Petesic et al. Aggregation of Antibody Drug Conjugates at Room Temperature: SAXS and Light Scattering Evidence for Colloidal Instability of a Specific Subpopulation. Langmuir 32(19):4848-61 (2016).
Galush et al. Chapter 13: Formulation Development of Antibody-Drug Conjugates. Antibody-Drug Conjugates 1045:217-233 (2013).
Junutula et al. Site-specific conjugation of a cytotoxic drug to an antibody improves the therapeutic index. Nat Biotechnol. 26(8):925-32 (2008).
Krall et al. Small targeted cytotoxics: current state and promises from DNA-encoded chemical libraries. Angewandte Chem. Int. Ed. 52:1384-1402.
PCT/US2021/044832 International Search Report and Written Opinion dated Nov. 22, 2021.
U.S. Appl. No. 16/691,417 Office Action dated Apr. 14, 2022.

\* cited by examiner

IMMUNOCONJUGATES TARGETING CD46 AND METHODS OF USE THEREOF

CROSS-REFERENCE

This application claims the benefit of U.S. Provisional Application No. 63/062,740, filed Aug. 7, 2020; which is incorporated herein by reference in its entirety.

The instant application contains a Sequence Listing which has been submitted electronically in ASCII format and is hereby incorporated by reference in its entirety. Said ASCII copy, created on Sep. 17, 2021, is named 39442-708_201_SL.txt and is 10,204 bytes in size.

BACKGROUND

CD46, also known as CD46 complement regulatory protein, cluster of differentiation 46 and membrane cofactor protein, is an inhibitory complement receptor. Overexpression of CD46 has been observed in several cancers, such as breast cancer, colorectal cancer, liver cancer, lung cancer, or prostate cancer. In some cases, overexpression of CD46 has been characterized as a negative prognostic factor. For example, overexpression of CD46 has been correlated with shorter progression-free time and shorter overall survival time in breast cancer patients and ovarian cancer patients. New therapies and treatment regimens targeting CD46 for the treatment of cancer are needed.

SUMMARY

The present disclosure provides immunoconjugates for the treatment conditions characterized by cell surface CD46 expression, such as metastatic castration resistant prostate cancer and multiple myeloma.

In some embodiments, immunoconjugate is administered to said human subject at a dose from about 1.0 to about 4.5 mg/kg, about 1.0 to about 4.0 mg/kg, about 1.0 to about 3.5 mg/kg, about 1.0 to about 3.0 mg/kg, about 1.0 to about 2.57 mg/kg, about 1.0 to about 2.5 mg/kg, about 1.0 to about 2.4 mg/kg, about 1.5 to about 4.5 mg/kg, about 1.5 to about 4.0 mg/kg, about 1.5 to about 3.5 mg/kg, about 1.5 to about 3.0 mg/kg, about 1.5 to about 2.57 mg/kg, about 1.5 to about 2.5 mg/kg, about 1.5 to about 2.4 mg/kg, about 1.5 to about 2.0 mg/kg, about 1.8 to about 4.5, mg/kg, about 1.8 to about 4.0, mg/kg, about 1.8 to about 3.5, mg/kg, about 1.8 to about 3.0, mg/kg, about 1.8 to about 2.5, or 7 mg/kg, about 1.8 to 2.0 about 2.5 mg/kg, about 1.8 to about 2.4 mg/kg, or about 1.8 to about 2.0 mg/kg. In some embodiments, the immunoconjugate is administered to said human subject at a dose from about 1.5 to about 2.5 mg/kg. In some embodiments, the immunoconjugate is administered to said human subject at a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0 mg/kg. In some embodiments, the immunoconjugate is administered to said human subject at a dose of about 1.8, about 2.4, or about 3.2 mg/kg. In some embodiments, the immunoconjugate is administered to said human subject at a dose of about 1.8 mg/kg. In some embodiments, the immunoconjugate is administered to said human subject at a dose of about 2.4 mg/kg. In some embodiments, the immunoconjugate is administered to said human subject at a dose of about 3.2 mg/kg.

In some embodiments, the immunoconjugate is administered to said human subject via intravenous infusion. In some embodiments, immunoconjugate is administered to said human subject every 7 days, every 14 days, every 18 days, every 21 days, or every 30 days. In some embodiments, immunoconjugate is administered to said human subject every 21 days.

In some embodiments, the recombinant antibody is conjugated to an effector agent wherein said effector agent comprises a drug (or a prodrug thereof), a peptide, a protein, a detectable label, a liposome containing a drug (or prodrug thereof), a radionuclide, a viral particle, or a chelate. In some embodiments, the effector comprises a drug. In some embodiments, the drug is an anti-cancer drug. In some embodiments, the drug is a chemotherapeutic agent. In some embodiments, the drug is a microtubule inhibitor, a DNA-damaging agent, or a polymerase inhibitor. In some embodiments, the drug is a microtubule inhibitor. In some embodiments, the microtubule inhibitor is an auristatin (or a derivative thereof), dolastatin-10 (or a derivative thereof), or maytansine (or a derivative thereof). In some embodiments, the microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the microtubule inhibitor is monomethylauristatin E (MMAE).

In some embodiments, the ratio of said effector agent to said recombinant antibody is from about 3 to about 5. In some embodiments, the ratio of said effector agent to said recombinant antibody is about 4.

In some embodiments, effector agent is conjugated to said recombinant antibody via a linker. In some embodiments, the linker is a peptide linker, a small molecule linker, or a linker that comprises a peptide and a small molecule. In some embodiments, the linker comprises maleimidocaproyl-valine-citrulline-para-amino benzyloxycarbonyl (mc-vc-PAB).

In some embodiments, the cancer is prostate cancer. In some embodiments, the prostate cancer is castration resistant prostate cancer. In some embodiments, the cancer is multiple myeloma. In some embodiments, the multiple myeloma is relapsed or refractory multiple myeloma.

In some embodiments, the immunoconjugate binds CD46 expressed on the surface of a cell and is internalized into the cell. In some embodiments, the immunoconjugate is internalized into said cell via macropinocytosis.

In another aspect, the disclosure provides a method of treating cancer in a human subject in need thereof, said method comprising administering to said subject an immunoconjugate that comprises: (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; and (b) monomethylauristatin E (MMAE) that is conjugated to said recombinant antibody via a maleimidocaproyl-valine-citrulline-para-amino benzyloxycarbonyl (mc-vc-PAB) linker; wherein said immunoconjugate is administered at a dose from about 1.0 to about 4.0 mg/kg.

In another aspect, the disclosure provides pharmaceutical composition that comprises (a) an immunoconjugate at a concentration of about 10.0±5.0 mg/mL, and (b) a histidine buffer; and wherein said immunoconjugate that comprises: (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; and (b) an effector agent that is conjugated to said recombinant antibody.

In some embodiments, the pharmaceutical composition comprises from about 10 to about 30 mM histidine buffer. In some embodiments, the pharmaceutical composition comprises from about 10 to about 20 mM histidine buffer. In some embodiments, the pharmaceutical composition further comprises cryoprotectant. In some embodiments, the cryoprotectant is a saccharide. In some embodiments, the sucrose or trehalose. In some embodiments, the pharmaceutical composition further comprises a stabilizing agent. In some embodiments, the stabilizing agent prevents denaturation of said recombinant antibody, prevents aggregation of said immunoconjugates, or both. In some embodiments, the stabilizing agent is a polysorbate. In some embodiments, the stabilizing agent is polysorbate 80. In some embodiments, the pharmaceutical composition has a pH from about 5.0 to about 7.0.

In some embodiments, the stabilizing agent is a polymer. In some embodiments, the polymer is a synthetic or semi-synthetic polymer. The polymer may be a linear polymer such as povidone or polyvinyl alcohol. The polymer may be a copolymer such as PVA-PEG graft copolymer. The polymer may be Ionic, such as carboxymethylcellulose sodium, sodium alginate, chitosan, or polyethylene glycol. A semi-synthetic polymer may be a non-ionic polymer such as HPMC, HPC, or HEC. In some embodiments, the stabilizing agent is a surfactant. The surfactant may be an ionic surfactant such as docusate sodium, sodium lauryl sulfate, or polyethylene imine or a non-ionic surfactant such as Tweens, poloxamers, D-α-tocopheryl, polyethylene glycol succinate, block co-polymers of polyethylene oxide-polyethylene oxide-Polyethylene oxide. In some embodiments, the stabilizing agent is food proteins, amino acids, or co-polymers. In some embodiments, the stabilizing agent is Captisol, Monosteol, Microcrystallin cellulose and carboxymethylcellulose, sorbitol, or a cellulose gel.

In some embodiments, the pharmaceutical composition comprises a buffering agent. The buffering agent may be selected from acetate, citrate, tartrate, histidine, glutamate, phosphate, Tris, glycine, bicarbonate, succinate, sulfate, or nitrate. In some embodiments, the pharmaceutical composition comprises a tonicity modifier. The tonicity modifier may be selected from mannitol, sorbitol, lactose, dextrose, trehalose, sodium chloride, potassium chloride, glycerol, and glycerin. In some embodiments, the pharmaceutical composition comprises a bulking agent. The bulking agent may be a sugar or polyol selected from sucrose, trehalose glucose, lactose, sorbitol, mannitol, and glycerol. The bulking agent may be an amino acid selected from arginine, aspartic acid, glutamic acid, lysine, proline, glycine, histidine, methionine, and alanine. The bulking agent may be a polymer or protein selected from gelatin, PVP, PLGA, PEG, dextran, cyclodextrin and derivatives, starch derivatives, HSA and BSA. In some embodiments, the pharmaceutical composition comprises an antioxidant. The antioxidant may be selected from histamine, methionine, ascorbic acid, glutathione, vitamin E, or poly(ethylenimine). In some embodiments, the pharmaceutical composition comprises an antimicrobial preservative. The pharmaceutical preservative may be selected from benzyl alcohol, metacresol, phenol, and 2-phenoxyethanol. In some embodiments, the pharmaceutical composition may comprise a chelating and/or complexing agent. The chelating agent may be edetate disodium, diethylenetriamine pentaacetic acid, citric acid, hexaphosphate, thioglycolic acid, or zinc.

In some embodiments, the recombinant antibody is conjugated to an effector agent wherein said effector agent comprises a drug (or a prodrug thereof), a peptide, a protein, a detectable label, a liposome containing a drug (or prodrug thereof), a radionuclide, a viral particle, or a chelate. In some embodiments, the effector comprises a drug. In some embodiments, the drug is an anti-cancer drug. In some embodiments, the drug is a chemotherapeutic agent. In some embodiments, the drug is a microtubule inhibitor, a DNA-damaging agent, or a polymerase inhibitor. In some embodiments, the drug is a microtubule inhibitor. In some embodiments, the microtubule inhibitor is an auristatin (or a derivative thereof), dolastatin-10 (or a derivative thereof), or maytansine (or a derivative thereof). In some embodiments, the microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the microtubule inhibitor is monomethylauristatin E (MMAE). In some embodiments, a ratio of said effector agent to said recombinant antibody in said population of immunoconjugates is from about 3 to about 5. In some embodiments, the ratio of said effector agent to said recombinant antibody in said population of immunoconjugates is about 4.

In some embodiments, the said effector agent is conjugated to said recombinant antibody via a linker. In some embodiments, the linker is a peptide linker, a small molecule linker, or a linker that comprises a peptide and a small molecule. In some embodiments, the linker comprises maleimidocaproyl-valine-citrulline-para-aminobenzyloxycarbonyl (mc-vc-PAB).

In another aspect, the disclosure provides, a pharmaceutical composition that comprises an immunoconjugate at a concentration of about 10.0±1.0 mg/mL, about 20 mM histidine buffer, about 8.0% sucrose, about 0.01% polysorbate 80; and wherein said immunoconjugate comprises: (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; (b) monomethylauristatin E (MMAE) that is conjugated to said recombinant antibody via a maleimidocaproyl-valine-citrulline-para-amino benzyloxycarbonyl (mc-vc-PAB) linker.

In another aspect, the disclosure provides a method of treating relapsed or refractory multiple myeloma (RRMM) in a human subject in need thereof, said method comprising administering to said subject a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, each with from 0 to 3 amino acid modifications, and said LC CDR1, LC CDR2, and LC CDR3 comprise an amino acid sequence of SEQ ID NO: 4, SEQ ID NO: 5, and SEQ ID NO: 6, respectively, each with from 0 to 3 amino acid modifications.

In another aspect, the disclosure provides a method of treating relapsed or refractory multiple myeloma (RRMM) in a human subject in need thereof, said method comprising administering to said subject a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively.

In another aspect, the disclosure provides a method of treating metastatic castration resistant prostate cancer in a human subject in need thereof, said method comprising administering to said subject a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, each with from 0 to 3 amino acid modifications, and said LC CDR1, LC CDR2, and LC CDR3 comprise an amino acid sequence of SEQ ID NO: 4, SEQ ID NO: 5, and SEQ ID NO: 6, respectively, each with from 0 to 3 amino acid modifications.

In another aspect, the disclosure provides a method of treating metastatic castration resistant prostate cancer in a human subject in need thereof, said method comprising administering to said subject a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively.

In some embodiments, the recombinant antibody for a method of treating relapsed or refractory multiple myeloma or castration resistant prostate cancer is conjugated to an effector agent wherein said effector agent comprises a drug (or a prodrug thereof), a peptide, a protein, a detectable label, a liposome containing a drug (or prodrug thereof), a radionuclide, a viral particle, or a chelate. In some embodiments, the effector comprises a drug. In some embodiments, the drug is an anti-cancer drug. In some embodiments, the drug is a chemotherapeutic agent. In some embodiments, the drug is a microtubule inhibitor, a DNA-damaging agent, or a polymerase inhibitor. In some embodiments, the drug is a microtubule inhibitor. In some embodiments, the microtubule inhibitor is an auristatin (or a derivative thereof), dolastatin-10 (or a derivative thereof), or maytansine (or a derivative thereof). In some embodiments, the microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the microtubule inhibitor is monomethylauristatin E (MMAE). In some embodiments, a ratio of said effector agent to said recombinant antibody is from about 3 to about 5. In some embodiments, the ratio of said effector agent to said recombinant antibody is about 4.

In some embodiments, the effector agent for a method of treating relapsed or refractory multiple myeloma or castration resistant prostate cancer is conjugated to said recombinant antibody via a linker. In some embodiments, the linker is a peptide linker, a small molecule linker, or a linker that comprises a peptide and a small molecule. In some embodiments, the linker comprises maleimidocaproyl-valine-citrulline-para-amino benzyloxycarbonyl (mc-vc-PAB).

In some embodiments, the recombinant antibody for a method of treating relapsed or refractory multiple myeloma or castration resistant prostate cancer is administered at a dose from about 1.0 to about 4.5 mg/kg, about 1.0 to about 4.0 mg/kg, about 1.0 to about 3.5 mg/kg, about 1.0 to about 3.0 mg/kg, about 1.0 to about 2.7 mg/kg, about 1.0 to about 2.5 mg/kg, about 1.0 to about 2.4 mg/kg, about 1.5 to about 4.5 mg/kg, about 1.5 to about 4.0 mg/kg, about 1.5 to about 3.5 mg/kg, about 1.5 to about 3.0 mg/kg, about 1.5 to 2. about 2.7 mg/kg, about 1.5 mg/kg, 1 to about 2.5 mg/kg, about 1.5 to about 2.4 mg/kg, about 1.5 to about 2.0 mg/kg, about 1.8 to about 4.5, mg/kg, about 1.8 to about 4.0, mg/kg, about 1.8 to about 3.5, mg/kg, about 1.8 to about 3.0, mg/kg, about 1.8 to about 2.5, or 7 mg/kg, about 1.8 to 2.0. about 2.5 mg/kg, about 1.8 to about 2.4 mg/kg, or about 1.8 to about 2.0 mg/kg. In some embodiments, the recombinant antibody is administered at a dose from about 1.5 to about 2.5 mg/kg. In some embodiments, the recombinant antibody is administered at a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0 mg/kg. In some embodiments, the recombinant antibody is administered at a dose of about 1.8, about 2.4, or about 3.2 mg/kg. In some embodiments, the recombinant antibody is administered at a dose of about 1.8 mg/kg. In some embodiments, the recombinant antibody is administered at a dose of about 2.4 mg/kg. In some embodiments, the recombinant antibody is administered at a dose of about 3.2 mg/kg.

In some embodiments, the recombinant antibody for a method of treating relapsed or refractory multiple myeloma or castration resistant prostate cancer is administered to said human subject via intravenous infusion. In some embodiments, the recombinant antibody is administered to said human subject every 7 days, every 14 days, every 18 days, every 21 days, every 28 days, or every month. In some embodiments, the recombinant antibody is administered to said human subject every 21 days.

In another aspect, the disclosure provides a method of treating relapsed or refractory multiple myeloma (RRMM) in a human subject in need thereof, said method comprising administering to said subject an immunoconjugate, wherein said immunoconjugate comprises (i) a recombinant antibody that specifically binds CD46 that comprises heavy chain (HC) variable region that comprises three complementarity determining regions (CDRs): HC CDR1, HC CDR2 and HC CDR3 and the light chain comprises a light chain (LC) variable region comprising three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and LC CDR1, LC CDR2, and LC CDR3 comprise an amino acid sequence of SEQ ID NO: 4, SEQ ID NO: 5, and SEQ ID NO: 6, respectively; conjugated to (ii) monomethylauristatin E (MMAE) via a linker, wherein said linker comprises maleimidocaproyl-valine-citrulline-para-amino benzyloxycarbonyl (mc-vc-PAB).

In another aspect, the disclosure provides an immunoconjugate comprising: a recombinant antibody comprising: a first heavy chain comprising SEQ ID NO: 9, a first light chain comprising SEQ ID NO: 10, a second heavy chain comprising SEQ ID NO: 9, and a second light chain comprising SEQ ID NO: 10; and one, two, three or four pairs of adducts; wherein each adduct of said one, two, three or four pairs of adducts comprises a monomethylauristatin E (MMAE) that is conjugated to said recombinant antibody via a maleimidocaproyl-valine-citrulline-para-amino benzyloxycarbonyl (mc-vc-PAB) linker; wherein each of said one, two, three, or four pairs of adducts is conjugated to a pair of cysteine residues of said recombinant antibody, wherein said pairs of cysteine residues are selected from: C219 of the first heavy chain and C214 of the first light chain; C219 of the second heavy chain and C214 of the second light chain; C225 of the first heavy chain and C225 of the second heavy chain; and C228 of the first heavy chain and C228 of the second heavy chain. In some embodiments, immunoconjugate comprises two pairs of said adducts.

In another aspect, the disclosure provides pharmaceutical composition comprising the immunoconjugate comprising: a recombinant antibody comprising: a first heavy chain comprising SEQ ID NO: 9, a first light chain comprising SEQ ID NO: 10, a second heavy chain comprising SEQ ID NO: 9, and a second light chain comprising SEQ ID NO: 10; and one, two, three or four pairs of adducts; wherein each adduct of said one, two, three or four pairs of adducts comprises a monomethylauristatin E (MMAE) that is conjugated to said recombinant antibody via a maleimidocaproyl-valine-citrulline-para-amino benzyloxycarbonyl (mc-vc-PAB) linker; wherein each of said one, two, three, or four pairs of adducts is conjugated to a pair of cysteine residues of said recombinant antibody, wherein said pairs of cysteine residues are selected from: C219 of the first heavy chain and C214 of the first light chain; C219 of the second heavy chain and C214 of the second light chain; C225 of the first heavy chain and C225 of the second heavy chain; and C228 of the first heavy chain and C228 of the second heavy chain; at a concentration of about 10.0±1.0 mg/mL, about 20 mM histidine buffer at pH 6.0, about 8.0% sucrose, and about 0.01% polysorbate 80.

In another aspect, the disclosure provides pharmaceutical composition that comprises an immunoconjugate at a concentration of about 10.0±1.0 mg/mL, about 20 mM histidine buffer, about 8.0% c sucrose, about 0.01% polysorbate 80; and wherein said immunoconjugate comprises: (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; and (b) monomethylauristatin E (MMAE) that is conjugated to said recombinant antibody via a maleimidocaproyl-valine-citrulline-para-amino benzyloxycarbonyl (mc-vc-PAB) linker.

In another aspect, the disclosure provides pharmaceutical composition comprising an immunoconjugate, a pharmaceutically acceptable buffer, and a pharmaceutically acceptable stabilizing agent; wherein said immunoconjugate comprises (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; (b) an effector agent that is conjugated to said recombinant antibody. In some embodiments, the pharmaceutical composition has a pH from about 5.0 to about 7.0. In some embodiments, the pharmaceutical composition comprising a pharmaceutically acceptable buffer; wherein the buffer comprises citrate, phosphate, acetate, tromethamine, histidine, succinate, malate, or α-ketoglutaric acid. In some embodiments, the pharmaceutical composition comprising a pharmaceutically acceptable buffer; wherein the buffer comprises from about 10 mM to about 30 mM histidine and the pH is from about 5 to about 7. In some embodiments, the pharmaceutical composition comprising a pharmaceutically acceptable buffer; wherein the buffer comprises citrate, phosphate, acetate, tromethamine, histidine, succinate, malate, or α-ketoglutaric acid; wherein the buffer comprises about 20 mM histidine and the pH is about 6.0. In some embodiments, the pharmaceutical composition comprising a pharmaceutically acceptable stabilizing agent; wherein the stabilizing agent prevents denaturation of said recombinant antibody, prevents aggregation of said immunoconjugates, or both. In some embodiments, the pharmaceutical composition comprising a pharmaceutically acceptable stabilizing agent; wherein the stabilizing agent comprises a non-ionic surfactant. In some embodiments, the pharmaceutical composition comprising a pharmaceutically acceptable stabilizing agent; wherein the stabilizing agent comprises a polysorbate. In some embodiments, the pharmaceutical composition comprising a pharmaceutically acceptable stabilizing agent; wherein the stabilizing agent comprises about 0.01% polysorbate-80. In some embodiments, the pharmaceutical composition comprising an immunoconjugate, a pharmaceutically acceptable buffer, and a pharmaceutically acceptable stabilizing agent further comprising a pharmaceutically acceptable cryoprotectant. In some embodiments, the pharmaceutical composition comprising an immunoconjugate, a pharmaceutically acceptable buffer, and a pharmaceutically acceptable stabilizing agent further comprising a pharmaceutically acceptable cryoprotectant; wherein the cryoprotectant comprises a saccharide. In some embodiments, the pharmaceutical composition comprising an immunoconjugate, a pharmaceutically acceptable buffer, and a pharmaceutically acceptable stabilizing agent further comprising a pharmaceutically acceptable cryoprotectant; wherein the cryoprotectant comprises a saccharide comprising about 6% to about 10% sucrose or trehalose. In some embodiments, the pharmaceutical composition comprising an immunoconjugate, a pharmaceutically acceptable buffer, and a pharmaceutically acceptable stabilizing agent further comprising a pharmaceutically acceptable cryoprotectant; wherein the cryoprotectant is about 8.0% sucrose.

In some embodiments, the pharmaceutical composition comprising an immunoconjugate, a pharmaceutically acceptable buffer, and a pharmaceutically acceptable stabilizing agent; wherein said immunoconjugate comprises (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; (b) an effector agent that is conjugated to said recombinant antibody; wherein said recombinant antibody is conjugated to an effector agent wherein said effector agent comprises a drug (or a prodrug thereof), a peptide, a protein, a detectable label, a liposome containing a drug (or prodrug thereof), a radionuclide, a viral particle, or a chelate. In some embodiments, the pharmaceutical composition comprising an effector agent; wherein said effector agent comprises a drug. In some embodiments, the pharmaceutical composition comprising an effector agent; wherein said effector agent comprises an anti-cancer drug. In some embodiments, the pharmaceutical composition comprising a drug; wherein said drug is a chemotherapeutic agent. In some embodiments, the pharmaceutical composition comprising a drug; wherein said drug is a microtubule inhibitor, a DNA-damaging agent, or a polymerase inhibitor. In some embodiments, the pharmaceutical composition comprising a drug that is a microtubule inhibitor; wherein said microtubule inhibitor is an auristatin (or a derivative thereof), dolastatin-10 (or a derivative thereof), or maytansine (or a derivative thereof). In some embodiments, the pharmaceutical composition comprising a drug that is a microtubule inhibitor; wherein said microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the pharmaceutical composition comprising an immunoconjugate comprising a recombinant antibody and an effector agent as described above; wherein a ratio of said effector agent to said recombinant antibody in a population of immunoconjugates is from about 3 to about 5. In some embodiments, the pharmaceutical composition comprising an immunoconjugate comprising a recombinant antibody and an effector agent as described above; wherein a ratio of said effector agent to said recombinant antibody in a population of immunoconjugates is about 4. In some embodiments, the pharmaceutical composition comprising an immunoconjugate comprising a recombinant antibody and an effector agent as described above; wherein said effector agent is conjugated to said recombinant antibody via a linker. In some embodiments, the pharmaceutical composition comprising an effector agent conjugated to a recombinant antibody via a linker as described above; wherein said linker is a peptide linker, a small molecule linker, or a linker that comprises a peptide and a small molecule. In some embodiments, the pharmaceutical composition comprising an effector agent conjugated to a recombinant antibody via a linker as described above; wherein said linker comprises maleimidocaproyl-valine-citrulline-para-amino benzyloxycarbonyl (mc-vc-PAB).

In another aspect, the disclosure provides a method of treating a cancer comprising a cell expressing CD46 in a human subject in need thereof, said method comprising administering to said subject an immunoconjugate comprising a recombinant antibody comprising: a first heavy chain comprising SEQ ID NO: 9, a first light chain comprising SEQ ID NO: 10, a second heavy chain comprising SEQ ID NO: 9, and a second light chain comprising SEQ ID NO: 10; and one, two, three, or four pairs of adducts; wherein each adduct of said one, two, three, or four pairs of adducts comprises a monomethylauristatin E (MMAE) that is conjugated to said recombinant antibody via a maleimido-caproyl-valine-citrulline-para-amino benzyloxycarbonyl (mc-vc-PAB) linker; wherein each of said one, two, three, or four pairs of adducts is conjugated to a pair of cysteine residues of said recombinant antibody; wherein said pairs of cysteine residues are selected from: C219 of the first heavy chain and C214 of the first light chain; C219 of the second heavy chain and C214 of the second light chain; C225 of the first heavy chain and C225 of the second heavy chain; and C228 of the first heavy chain and C228 of the second heavy chain. In some embodiments, the method of treating a cancer; wherein said cancer is relapsed or refractory multiple myeloma (RRMM). In some embodiments, the method of treating a cancer; wherein said cancer is metastatic castration resistant prostate cancer (mCRPC). In some embodiments, the method of treating a cancer comprising administering an immunoconjugate to the subject; wherein said immunoconjugate comprises two pairs of said adducts. In some embodiments, the method of treating a cancer as described above, further comprising detecting said CD46 in said cell. In some embodiments, the method of treating a cancer as described above, further comprising detecting said CD46 in said cell; wherein said detecting comprises immunofluorescence microscopy or immunohistochemistry. In some embodiments, the method of treating a cancer as described above, further comprising detecting said CD46 in said cell; wherein said detecting comprises flow cytometry. In some embodiments, the method of treating a cancer as described above, further comprising detecting said CD46 in said cell; wherein said detecting comprises detecting an amplification of chromosome location 1q21. In some embodiments, the method of treating a cancer as described above, wherein the immunoconjugate is administered to the human subject via intravenous infusion. In some embodiments, the method of treating a cancer as described above, wherein the immunoconjugate is administered to the human subject every 7 days, every 14 days, every 18 days, every 21 days, or every 30 days. In some embodiments, the method of treating a cancer as described above, wherein the immunoconjugate is administered to the human subject every 21 days over at least three cycles. In some embodiments, the method of treating a cancer as described above, wherein the immunoconjugate is administered at a dose from about 1.2 to about 3.0 mg/kg. In some embodiments, the method of treating a cancer as described above, wherein the recombinant antibody is administered at a dose of about 1.8, about 2.4, about 2.7, or about 3.0 mg/kg. In some embodiments, the method of treating a cancer as described above, wherein the weight, in kg, of the human subject in need is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg; or 100 kg if the adjusted body weight of said human subject is greater than or equal to 100 kg. In some embodiments, the method of treating a cancer as described above, wherein the weight, in kg, of the human subject in need is an actual body weight. In some embodiments, the method of treating a cancer as described above, wherein the weight, in kg, of the human subject in need is an adjusted body weight.

In another aspect, the disclosure provides a method of treating metastatic castration resistant prostate cancer in a human subject in need thereof, said method comprising administering to said subject an immunoconjugate comprising: (i) a recombinant antibody that specifically binds CD46 that comprises heavy chain (HC) variable region that comprises three complementarity determining regions (CDRs): HC CDR1, HC CDR2 and HC CDR3 and the light chain comprises a light chain (LC) variable region comprising three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and LC CDR1, LC CDR2, and LC CDR3 comprise an amino acid sequence of SEQ ID NO: 4, SEQ ID NO: 5, and SEQ ID NO: 6, respectively; conjugated to (ii) monomethylauristatin E (MMAE) via a linker; wherein said linker comprises maleimidocaproyl-valine-citrulline-para-amino benzyloxycarbonyl (mc-vc-PAB); wherein said immunoconjugate is administered at a dose of from about 1.2 to about 3.0 mg/kg.

In another aspect, the disclosure provides a method of treating relaxed or refractory multiple myeloma in a human subject in need thereof, said method comprising administering to said subject an immunoconjugate comprising: (i) a recombinant antibody that specifically binds CD46 that comprises heavy chain (HC) variable region that comprises three complementarity determining regions (CDRs): HC CDR1, HC CDR2 and HC CDR3 and the light chain comprises a light chain (LC) variable region comprising three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and LC CDR1, LC CDR2, and LC CDR3 comprise an amino acid sequence of SEQ ID NO: 4, SEQ ID NO: 5, and SEQ ID NO: 6, respectively; conjugated to (ii) monomethylauristatin E (MMAE) via a linker; wherein said linker comprises maleimidocaproyl-valine-citrulline-para-amino benzyloxycarbonyl (mc-vc-PAB); wherein said immunoconjugate is administered at a dose of from about 1.8 to about 3.0 mg/kg. In some embodiments, the method of treating metastatic castration resistant prostate cancer or the method of treating relaxed or refractory multiple myeloma in a human subject; wherein a calculated weight, in kg, of said human subject is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg; or 100 kg if the adjusted body weight of said human subject is greater than or equal to 100 kg. In some embodiments, the method of treating metastatic castration resistant prostate cancer or the method of treating relaxed or refractory multiple myeloma in a human subject; wherein a calculated weight, in kg, of said human subject is an adjusted body weight. In some embodiments, the method of treating metastatic castration resistant prostate cancer or the method of treating relaxed or refractory multiple myeloma in a human subject; wherein the weight, in kg, of said human subject is an actual body weight.

In some embodiments, the method of treating metastatic castration resistant prostate cancer or the method of treating relaxed or refractory multiple myeloma in a human subject further comprising detecting said CD46 in said cell. In some embodiments, the method of treating metastatic castration resistant prostate cancer or the method of treating relaxed or refractory multiple myeloma in a human subject further comprising detecting said CD46 in said cell; wherein said detecting comprises immunofluorescence microscopy or immunohistochemistry. In some embodiments, the method of treating metastatic castration resistant prostate cancer or the method of treating relaxed or refractory multiple myeloma in a human subject further comprising detecting said CD46 in said cell; wherein said detecting comprises flow cytometry. In some embodiments, the method of treating metastatic castration resistant prostate cancer or the method of treating relaxed or refractory multiple myeloma in a human subject further comprising detecting said CD46 in said cell; wherein said detecting comprises detecting an amplification of chromosome location 1q21. In some embodiments, the method of treating metastatic castration resistant prostate cancer or the method of treating relaxed or refractory multiple myeloma in a human subject as described above; wherein the immunoconjugate is administered to said human subject via intravenous infusion. In some embodiments, the method of treating metastatic castration resistant prostate cancer or the method of treating relaxed or refractory multiple myeloma in a human subject as described above; wherein the immunoconjugate is administered to said human subject every 7 days, every 14 days, every 18 days, every 21 days, or every 30 days. In some embodiments, the method of treating metastatic castration resistant prostate cancer or the method of treating relaxed or refractory multiple myeloma in a human subject as described above; wherein the immunoconjugate is administered to said human subject every 21 days over at least three cycles.

In another aspect, the disclosure provides a method of treating cancer in a human subject in need thereof, said method comprising administering to said human subject an immunoconjugate that comprises: a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; an effector agent that is conjugated to said recombinant antibody; and wherein said immunoconjugate is administered at a dose from about 1.0 to about 5.0 mg/kg or administered at a dose from about 1.0 to about 4.0 mg/kg. In some embodiments, the method of treating cancer; wherein said cancer is prostate cancer. In some embodiments, the method of treating prostate cancer; wherein said prostate cancer is metastatic castration resistant prostate cancer. In some embodiments, the method of treating cancer; wherein said cancer is multiple myeloma. In some embodiments, the method of treating multiple myeloma; wherein multiple myeloma is relapsed or refractory multiple myeloma. In some embodiments, the method of treating cancer as described above further comprising detecting CD46 expression in a cell of said cancer. In some embodiments, the method of treating cancer as described above further comprising detecting CD46 expression in a cell of said cancer, wherein said detecting comprises immunofluorescence microscopy or immunohistochemistry. In some embodiments, the method of treating cancer as described above further comprising detecting CD46 expression in a cell of said cancer, wherein said detecting comprises flow cytometry. In some embodiments, the method of treating cancer as described above further comprising detecting CD46 expression in a cell of said cancer, wherein said detecting comprises detecting an amplification of chromosome location 1q21. In some embodiments, the method of treating cancer as described above; wherein said cancer has higher CD46 expression than a non-cancerous tissue of the same tissue type from the subject or from a healthy individual. In some embodiments, the method of treating cancer as described above; wherein said cancer comprises a copy number increase of chromosome band 1q21. In some embodiments, the method of treating cancer as described above; wherein the immunoconjugate is administered at a dose from about 1.0 to about 4.5 mg/kg, about 1.0 to about 4.0 mg/kg, about 1.0 to about 3.5 mg/kg, about 1.0 to about 3.0 mg/kg, about 1.0 to about 2.7 mg/kg, about 1.0 to about 2.5 mg/kg, about 1.0 to about 2.4 mg/kg, about 1.5 to about 4.5 mg/kg, about 1.5 to about 4.0 mg/kg, about 1.5 to about 3.5 mg/kg, about 1.5 to about 3.0 mg/kg, about 1.5 to about 2.7 mg/kg, about 1.5 to about 2.5 mg/kg, about 1.5 to about 2.4 mg/kg, about 1.5 to about 2.0 mg/kg, about 1.8 to about 4.5 mg/kg, about 1.8 to about 4.0 mg/kg, about 1.8 to about 3.5 mg/kg, about 1.8 to about 3.0 mg/kg, about 1.8 to about 2.7 mg/kg, about 1.8 to about 2.5 mg/kg, about 1.8 to about 2.4 mg/kg, or about 1.8 to about 2.0 mg/kg. In some embodiments, the method of treating cancer as described above; wherein the immunoconjugate is administered at a dose of from about 1.2 to about 3.0 mg/kg. In some embodiments, the method of treating cancer as described above; wherein the immunoconjugate is administered at a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0 mg/kg. In some embodiments, the method of treating cancer as described above; wherein the immunoconjugate is administered at a dose of about 1.8, about 2.4, about 2.7, or about 3.0 mg/kg. In some embodiments, the method of treating cancer as described above; wherein the immunoconjugate is administered at a dose of about 1.8 mg/kg. In some embodiments, the method of treating cancer as described above; wherein the immunoconjugate is administered at a dose of about 2.4 mg/kg. In some embodiments, the method of treating cancer as described above; wherein the immunoconjugate is administered at a dose of about 2.7 mg/kg. In some embodiments, the method of treating cancer as described above; wherein the immunoconjugate is administered at a dose of about 3.0 mg/kg. In some embodiments, the method of treating cancer in a human subject as described above; wherein the weight, in kg, of said human subject is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg; or 100 kg if the adjusted body weight of said human subject is greater than or equal to 100 kg. In some embodiments, the method of treating cancer in a human subject as described above; wherein the weight, in kg, of said human subject is an actual body weight. In some embodiments, the method of treating cancer in a human subject as described above; wherein the weight, in kg, of said human subject is an adjusted body weight. In some embodiments, the method of treating cancer in a human subject, said method comprising administering to said human subject an immunoconjugate comprising recombinant antibody as described above; wherein the recombinant antibody is administered to said human subject via intravenous infusion. In some embodiments, the method of treating cancer in a human subject, said method comprising administering to said human subject an immunoconjugate comprising recombinant antibody as described above; wherein the recombinant antibody is administered to said human subject every 7 days, every 14 days, every 18 days, every 21 days, or every 30 days. In some embodiments, the method of treating cancer in a human subject, said method comprising administering to said human subject an immunoconjugate comprising recombinant antibody as described above; wherein the recombinant antibody is administered to said human subject every 21 days over at least three cycles. In some embodiments, the method of treating cancer in a human subject, said method comprising administering to said human subject an immunoconjugate comprising the effector agent as described above; wherein said effector agent comprises a drug (or a prodrug thereof), a peptide, a protein, a detectable label, a liposome containing a drug (or prodrug thereof), a radionuclide, a viral particle, or a chelate. In some embodiments, the method of treating cancer in a human subject, said method comprising administering to said human subject an immunoconjugate comprising the effector agent as described above; wherein said effector agent comprises a drug. In some embodiments, the method of treating cancer in a human subject as described above; wherein the effector agent comprises an anti-cancer drug. In some embodiments, the method of treating cancer in a human subject as described above; wherein the effector agent comprises a drug; wherein said drug is a chemotherapeutic agent. In some embodiments, the method of treating cancer in a human subject as described above; wherein the effector agent comprises a drug; wherein said drug is a microtubule inhibitor, a DNA-damaging agent, or a polymerase inhibitor. In some embodiments, the method of treating cancer in a human subject as described above; wherein the effector agent comprises a drug; wherein said drug is a microtubule inhibitor. In some embodiments, the method of treating cancer in a human subject as described above; wherein the microtubule inhibitor is an auristatin (or a derivative thereof), dolastatin-10 (or a derivative thereof), or maytansine (or a derivative thereof). In some embodiments, the method of treating cancer in a human subject as described above; wherein the microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the method of treating cancer in a human subject as described above; wherein the microtubule inhibitor is monomethylauristatin E (MMAE). In some embodiments, the method of treating cancer in a human subject, said method comprising administering to said human subject an immunoconjugate comprising the effector agent and the recombinant antibody as described above; wherein a ratio of said effector agent to said recombinant antibody is from about 3 to about 5. In some embodiments, the method of treating cancer in a human subject as described above; wherein a ratio of said effector agent to said recombinant antibody is about 4. In some embodiments, the method of treating cancer in a human subject as described above; wherein said effector agent is conjugated to said recombinant antibody via a linker. In some embodiments, the method of treating cancer in a human subject as described above; wherein said linker is a peptide linker, a small molecule linker, or a linker that comprises a peptide and a small molecule. In some embodiments, the method of treating cancer in a human subject as described above; wherein said linker comprises maleimidocaproyl-valine-citrulline-para-amino benzyloxycarbonyl (mc-vc-PAB). In some embodiments, the method of treating cancer in a human subject as described above; wherein said immunoconjugate binds CD46 expressed on the surface of a cell and is internalized into said cell. In some embodiments, the method of treating cancer in a human subject as described above; wherein said immunoconjugate is internalized into said cell via macropinocytosis.

In another aspect, the disclosure provides an immunoconjugate comprising: a recombinant antibody comprising: a first heavy chain comprising SEQ ID NO: 9, a first light chain comprising SEQ ID NO: 10, a second heavy chain comprising SEQ ID NO: 9, and a second light chain comprising SEQ ID NO: 10; and one, two, three or four pairs of adducts; wherein each adduct of said one, two, three or four pairs of adducts comprises a monomethylauristatin E (MMAE) that is conjugated to said recombinant antibody via a maleimidocaproyl-valine-citrulline-para-amino benzyloxycarbonyl (mc-vc-PAB) linker; wherein each of said one, two, three, or four pairs of adducts is conjugated to a pair of cysteine residues of said recombinant antibody, wherein said pairs of cysteine residues are selected from: C219 of the first heavy chain and C214 of the first light chain, C219 of the second heavy chain and C214 of the second light chain, C225 of the first heavy chain and C225 of the second heavy chain, and C228 of the first heavy chain and C228 of the second heavy chain; for use in the treatment of a cancer in a human subject comprising a cell expressing CD46. In some embodiments, the immunoconjugate for use in the treatment of a cancer in a human subject as described above, wherein said cancer is relapsed or refractory multiple myeloma (RRMM). In some embodiments, the immunoconjugate for use in the treatment of a cancer in a human subject as described above, wherein said cancer is metastatic castration resistant prostate cancer (mCRPC). In some embodiments, the immunoconjugate for use in the treatment of a cancer in a human subject as described above, wherein said immunoconjugate comprises two pairs of said adducts. In some embodiments, the immunoconjugate for use in the treatment of a cancer in a human subject comprising a cell expressing CD46 as described above, wherein said cell comprises CD46 as determined by immunofluorescence microscopy or immunohistochemistry. In some embodiments, the immunoconjugate for use in the treatment of a cancer in a human subject comprising a cell expressing CD46 as described above, wherein said cell comprises CD46 as determined by flow cytometry. In some embodiments, the immunoconjugate for use in the treatment of a cancer in a human subject comprising a cell expressing CD46 as described above, wherein said cell comprises an amplification of chromosome location 1q21. In some embodiments, the immunoconjugate for use in the treatment of a cancer in a human subject as described above, wherein said immunoconjugate is formulated for intravenous infusion. In some embodiments, the immunoconjugate for use in the treatment of a cancer in a human subject as described above, wherein said immunoconjugate is administered to said human subject every 7 days, every 14 days, every 18 days, every 21 days, every 28 days, or every month. In some embodiments, the immunoconjugate for use in the treatment of a cancer in a human subject as described above, wherein said immunoconjugate is administered to said human subject every 21 days. In some embodiments, the immunoconjugate for use in the treatment of a cancer in a human subject as described above, wherein said immunoconjugate is administered at a dose from about 1.2 to about 3.0 mg/kg. In some embodiments, the immunoconjugate comprising a recombinant antibody for use in the treatment of a cancer in a human subject as described above, wherein said recombinant antibody is administered at a dose of about 1.8, about 2.4, about 2.7, or about 3.0 mg/kg. In some embodiments, the immunoconjugate for use in the treatment of a cancer in a human subject as described above; wherein the weight, in kg, of said human subject is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg, or 100 kg if the adjusted body weight of said human subject is greater than or equal to 100 kg. In some embodiments, the immunoconjugate for use in the treatment of a cancer in a human subject as described above; wherein the weight, in kg, of said human subject is an actual body weight. In some embodiments, the immunoconjugate for use in the treatment of a cancer in a human subject as described above; wherein the weight, in kg, of said human subject is an adjusted body weight.

In another aspect, the disclosure provides an immunoconjugate for the treatment of metastatic castration resistant prostate cancer in a human subject in need thereof comprising, (i) a recombinant antibody that specifically binds CD46 that comprises heavy chain (HC) variable region that comprises three complementarity determining regions (CDRs): HC CDR1, HC CDR2 and HC CDR3 and the light chain comprises a light chain (LC) variable region comprising three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and LC CDR1, LC CDR2, and LC CDR3 comprise an amino acid sequence of SEQ ID NO: 4, SEQ ID NO: 5, and SEQ ID NO: 6, respectively; conjugated to (ii) monomethylauristatin E (MMAE) via a linker, wherein said linker comprises maleimidocaproyl-valine-citrulline-para-amino benzyloxycarbonyl (mc-vc-PAB), wherein said immunoconjugate is administered at a dose of from about 1.2 to about 3.0 mg/kg.

In another aspect, the disclosure provides an immunoconjugate for the treatment of refractory multiple myeloma in a human subject in need thereof comprising, (i) a recombinant antibody that specifically binds CD46 that comprises heavy chain (HC) variable region that comprises three complementarity determining regions (CDRs): HC CDR1, HC CDR2 and HC CDR3 and the light chain comprises a light chain (LC) variable region comprising three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and LC CDR1, LC CDR2, and LC CDR3 comprise an amino acid sequence of SEQ ID NO: 4, SEQ ID NO: 5, and SEQ ID NO: 6, respectively; conjugated to (ii) monomethylauristatin E (MMAE) via a linker, wherein said linker comprises maleimidocaproyl-valine-citrulline-para-amino benzyloxycarbonyl (mc-vc-PAB), wherein said immunoconjugate is administered at a dose of from about 1.8 to about 3.0 mg/kg.

In some embodiments, the immunoconjugate for the treatment of metastatic castration resistant prostate cancer or for the treatment of refractory multiple myeloma in a human subject wherein the calculated weight, in kg, of said human subject is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg; or 100 kg if the adjusted body weight of said human subject is greater than or equal to 100 kg. In some embodiments, the immunoconjugate for the treatment of metastatic castration resistant prostate cancer or for the treatment of refractory multiple myeloma in a human subject wherein the weight, in kg, of said human subject is an actual body weight. In some embodiments, the immunoconjugate for the treatment of metastatic castration resistant prostate cancer or for the treatment of refractory multiple myeloma in a human subject wherein the weight, in kg, of said human subject is an adjusted body weight. In some embodiments, the immunoconjugate for the treatment of metastatic castration resistant prostate cancer or for the treatment of refractory multiple myeloma in a human subject comprising a cell; wherein said cell comprises CD46 as determined by immunofluorescence microscopy or immunohistochemistry. In some embodiments, the immunoconjugate for the treatment of metastatic castration resistant prostate cancer or for the treatment of refractory multiple myeloma in a human subject comprising a cell; wherein said cell comprises CD46 as determined by flow cytometry. In some embodiments, the immunoconjugate for the treatment of metastatic castration resistant prostate cancer or for the treatment of refractory multiple myeloma in a human subject comprising a cell; wherein said cell comprises an amplification of chromosome location 1q21. In some embodiments, the immunoconjugate for the treatment of metastatic castration resistant prostate cancer or for the treatment of refractory multiple myeloma in a human subject; wherein said immunoconjugate is formulated for intravenous infusion. In some embodiments, the immunoconjugate for the treatment of metastatic castration resistant prostate cancer or for the treatment of refractory multiple myeloma in a human subject; wherein said immunoconjugate is administered to said human subject every 7 days, every 14 days, every 18 days, every 21 days, every 28 days, or every month. In some embodiments, the immunoconjugate for the treatment of metastatic castration resistant prostate cancer or for the treatment of refractory multiple myeloma in a human subject; wherein said immunoconjugate is administered to said human subject every 21 days over at least three cycles.

In another aspect, the disclosure provides an immunoconjugate for treating cancer in a human subject in need thereof comprising: (a) a recombinant antibody that specifically binds CD46 that comprises a heavy chain (HC) variable region that comprises three complementarity determining regions (CDRs): HC CDR1, HC CDR2 and HC CDR3 and a light chain (LC) variable region that comprises three CDRs: LC CDR1, LC CDR2, and LC CDR3, wherein said HC CDR1, HC CDR2, HC CDR3 comprise an amino acid sequence of SEQ ID NO: 1, SEQ ID NO: 2, and SEQ ID NO: 3, respectively, and said LC CDR1, LC CDR2, and LC CDR3 comprise an amino acid sequence of SEQ ID NO: 4, SEQ ID NO: 5, and SEQ ID NO: 6, respectively; (b) an effector agent that is conjugated to said recombinant antibody; and wherein said immunoconjugate is administered at a dose from about 1.0 to about 5.0 mg/kg. In some embodiments, the immunoconjugate for treating cancer in a human subject; wherein said cancer is prostate cancer. In some embodiments, the immunoconjugate for treating cancer in a human subject; wherein said prostate cancer is metastatic castration resistant prostate cancer. In some embodiments, the immunoconjugate for treating cancer in a human subject; wherein said prostate cancer is multiple myeloma. In some embodiments, the immunoconjugate for treating multiple myeloma in a human subject; wherein said multiple myeloma is relapsed or refractory multiple myeloma. In some embodiments, the immunoconjugate for treating cancer in a human subject; wherein said cancer comprises a cell that expresses CD46 as determined by immunofluorescence microscopy or immunohistochemistry. In some embodiments, the immunoconjugate for treating cancer in a human subject; wherein said cancer comprises a cell that expresses CD46 as determined by flow cytometry. In some embodiments, the immunoconjugate for treating cancer in a human subject; wherein said cancer comprises an amplification of chromosome location 1q21. In some embodiments, the immunoconjugate for treating cancer in a human subject, wherein said cancer has higher CD46 expression than a non-cancerous tissue of the same tissue type from the subject or from a healthy individual. In some embodiments, the immunoconjugate for treating cancer in a human subject; wherein said immunoconjugate is administered at a dose from about 1.0 to about 4.5 mg/kg, about 1.0 to about 4.0 mg/kg, about 1.0 to about 3.5 mg/kg, about 1.0 to about 3.0 mg/kg, about 1.0 to about 2.7 mg/kg, about 1.0 to about 2.5 mg/kg, about 1.0 to about 2.4 mg/kg, about 1.5 to about 4.5 mg/kg, about 1.5 to about 4.0 mg/kg, about 1.5 to about 3.5 mg/kg, about 1.5 to about 3.0 mg/kg, about 1.5 to about 2.7 mg/kg, about 1.5 to about 2.5 mg/kg, about 1.5 to about 2.4 mg/kg, about 1.5 to about 2.0 mg/kg, about 1.8 to about 4.5 mg/kg, about 1.8 to about 4.0 mg/kg, about 1.8 to about 3.5 mg/kg, about 1.8 to about 3.0 mg/kg, about 1.8 to about 2.7 mg/kg, about 1.8 to about 2.5 mg/kg, about 1.8 to about 2.4 mg/kg, or about 1.8 to about 2.0 mg/kg. In some embodiments, the immunoconjugate for treating cancer in a human subject; wherein said immunoconjugate is administered at a dose from about 1.2 to about 3.0 mg/kg. In some embodiments, the immunoconjugate for treating cancer in a human subject; wherein said immunoconjugate is administered at a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0 mg/kg. In some embodiments, the immunoconjugate for treating cancer in a human subject; wherein said immunoconjugate is administered at a dose of about 1.8, about 2.4, about 2.7, or about 3.0 mg/kg. In some embodiments, the immunoconjugate for treating cancer in a human subject; wherein said immunoconjugate is administered at a dose of about 1.8, about 2.4, about 2.7, or about 3.0 mg/kg. In some embodiments, the immunoconjugate for treating cancer in a human subject; wherein said immunoconjugate is administered at a dose of about 1.8 mg/kg. In some embodiments, the immunoconjugate for treating cancer in a human subject; wherein said immunoconjugate is administered at a dose of about 2.4 mg/kg. In some embodiments, the immunoconjugate for treating cancer in a human subject; wherein said immunoconjugate is administered at a dose of about 2.7 mg/kg. In some embodiments, the immunoconjugate for treating cancer in a human subject; wherein said immunoconjugate is administered at a dose of about 3.0 mg/kg. In some embodiments, the immunoconjugate for treating cancer in a human subject; wherein the weight, in kg, of said human subject is: an actual body weight of said human subject if the actual body weight of said human subject is less than an adjusted body weight of said subject; an adjusted body weight of said human subject if the actual body weight of said human subject is greater than or equal to an adjusted body weight of said subject, and the adjusted body weight of said human subject is less than 100 kg; or 100 kg if the adjusted body weight of said human subject is greater than or equal to 100 kg. In some embodiments, the immunoconjugate for treating cancer in a human subject; wherein the weight, in kg, of said human subject is an actual body weight. In some embodiments, the immunoconjugate for treating cancer in a human subject; wherein the weight, in kg, of said human subject is an adjusted body weight. In some embodiments, the immunoconjugate comprising the recombinant antibody for treating cancer in a human subject; wherein said recombinant antibody is formulated for intravenous infusion. In some embodiments, the immunoconjugate comprising the recombinant antibody for treating cancer in a human subject; wherein said recombinant antibody is administered to said human subject every 7 days, every 14 days, every 18 days, every 21 days, or every 30 days. In some embodiments, the immunoconjugate comprising the recombinant antibody for treating cancer in a human subject; wherein said recombinant antibody is administered to said human subject every 21 days. In some embodiments, the immunoconjugate comprising the effector agent for treating cancer in a human subject; wherein said effector agent comprises a drug (or a prodrug thereof), a peptide, a protein, a detectable label, a liposome containing a drug (or prodrug thereof), a radionuclide, a viral particle, or a chelate. In some embodiments, the immunoconjugate comprising the effector agent for treating cancer in a human subject; wherein said effector agent comprises a drug. In some embodiments, the immunoconjugate comprising the effector agent for treating cancer in a human subject; wherein said effector agent comprises an anti-cancer drug. In some embodiments, the immunoconjugate comprising the effector agent; wherein said effector agent comprises a chemotherapeutic agent. In some embodiments, the immunoconjugate comprising the effector agent; wherein said effector agent comprises a drug; wherein said drug is a microtubule inhibitor, a DNA-damaging agent, or a polymerase inhibitor. In some embodiments, the immunoconjugate comprising a microtubule inhibitor, wherein said microtubule inhibitor is an auristatin (or a derivative thereof), dolastatin-10 (or a derivative thereof), or maytansine (or a derivative thereof). In some embodiments, the immunoconjugate comprising a microtubule inhibitor, wherein said microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the immunoconjugate comprising the effector agent; wherein said effector agent comprises a drug; wherein said drug is a microtubule inhibitor, wherein said microtubule inhibitor is monomethylauristatin E (MMAE). In some embodiments, the immunoconjugate comprising the effector agent and the recombinant antibody; wherein a ratio of said effector agent to said recombinant antibody is from about 3 to about 5. In some embodiments, the immunoconjugate comprising the effector agent and the recombinant antibody; wherein a ratio of said effector agent to said recombinant antibody is from about 4. In some embodiments, the immunoconjugate comprising the effector agent and the recombinant antibody; wherein said effector agent is conjugated to said recombinant antibody via a linker. In some embodiments, the immunoconjugate comprising the effector agent conjugated to the recombinant antibody via a linker; wherein said linker is a peptide linker, a small molecule linker, or a linker that comprises a peptide and a small molecule. In some embodiments, the immunoconjugate comprising the effector agent conjugated to the recombinant antibody via a linker, wherein said linker comprises maleimidocaproyl-valine-citrulline-para-amino benzyloxycarbonyl (mc-vc-PAB). In some embodiments, the immunoconjugate comprising the effector agent and the recombinant antibody; wherein said immunoconjugate binds CD46 expressed on the surface of a cell and is internalized into said cell. In some embodiments, the immunoconjugate comprising the effector agent and the recombinant antibody; wherein said immunoconjugate is internalized into said cell via macropinocytosis.

In another aspect, the disclosure provides a pharmaceutical formulation for the treatment of metastatic castration resistant prostate cancer in a human subject in need thereof comprising an immunoconjugate a concentration of about 10.0 t 1.0 mg/mL, about 20 mM histidine buffer, about 8.0% sucrose, about 0.01% polysorbate 80; and wherein said immunoconjugate comprises: a recombinant antibody comprising: a first heavy chain comprising SEQ ID NO: 9, a first light chain comprising SEQ ID NO: 10, a second heavy chain comprising SEQ ID NO: 9, and a second light chain comprising SEQ ID NO: 10; and one, two, three or four pairs of adducts; wherein each adduct of said one, two, three or four pairs of adducts comprises a monomethylauristatin E (MMAE) that is conjugated to said recombinant antibody via a maleimidocaproyl-valine-citrulline-para-amino benzyloxycarbonyl (mc-vc-PAB) linker; wherein each of said one, two, three, or four pairs of adducts is conjugated to a pair of cysteine residues of said recombinant antibody, wherein said pairs of cysteine residues are selected from: C219 of the first heavy chain and C214 of the first light chain; C219 of the second heavy chain and C214 of the second light chain; C225 of the first heavy chain and C225 of the second heavy chain; and C228 of the first heavy chain and C228 of the second heavy chain.

In another aspect, the disclosure provides a pharmaceutical formulation for the treatment of refractory multiple myeloma in a human subject in need thereof comprising an immunoconjugate a concentration of about 10.0±1.0 mg/mL, about 20 mM histidine buffer, about 8.0% sucrose, about 0.01% polysorbate 80; and wherein said immunoconjugate comprises: a recombinant antibody comprising: a first heavy chain comprising SEQ ID NO: 9, a first light chain comprising SEQ ID NO: 10, a second heavy chain comprising SEQ ID NO. 9, and a second light chain comprising SEQ ID NO: 10; and one, two, three or four pairs of adducts; wherein each adduct of said one, two, three or four pairs of adducts comprises a monomethylauristatin E (MMAE) that is conjugated to said recombinant antibody via a maleimidocaproyl-valine-citrulline-para-amino benzyloxycarbonyl (mc-vc-PAB) linker; wherein each of said one, two, three, or four pairs of adducts is conjugated to a pair of cysteine residues of said recombinant antibody, wherein said pairs of cysteine residues are selected from: C219 of the first heavy chain and C214 of the first light chain; C219 of the second heavy chain and C214 of the second light chain; C225 of the

DETAILED DESCRIPTION

Figure 1:
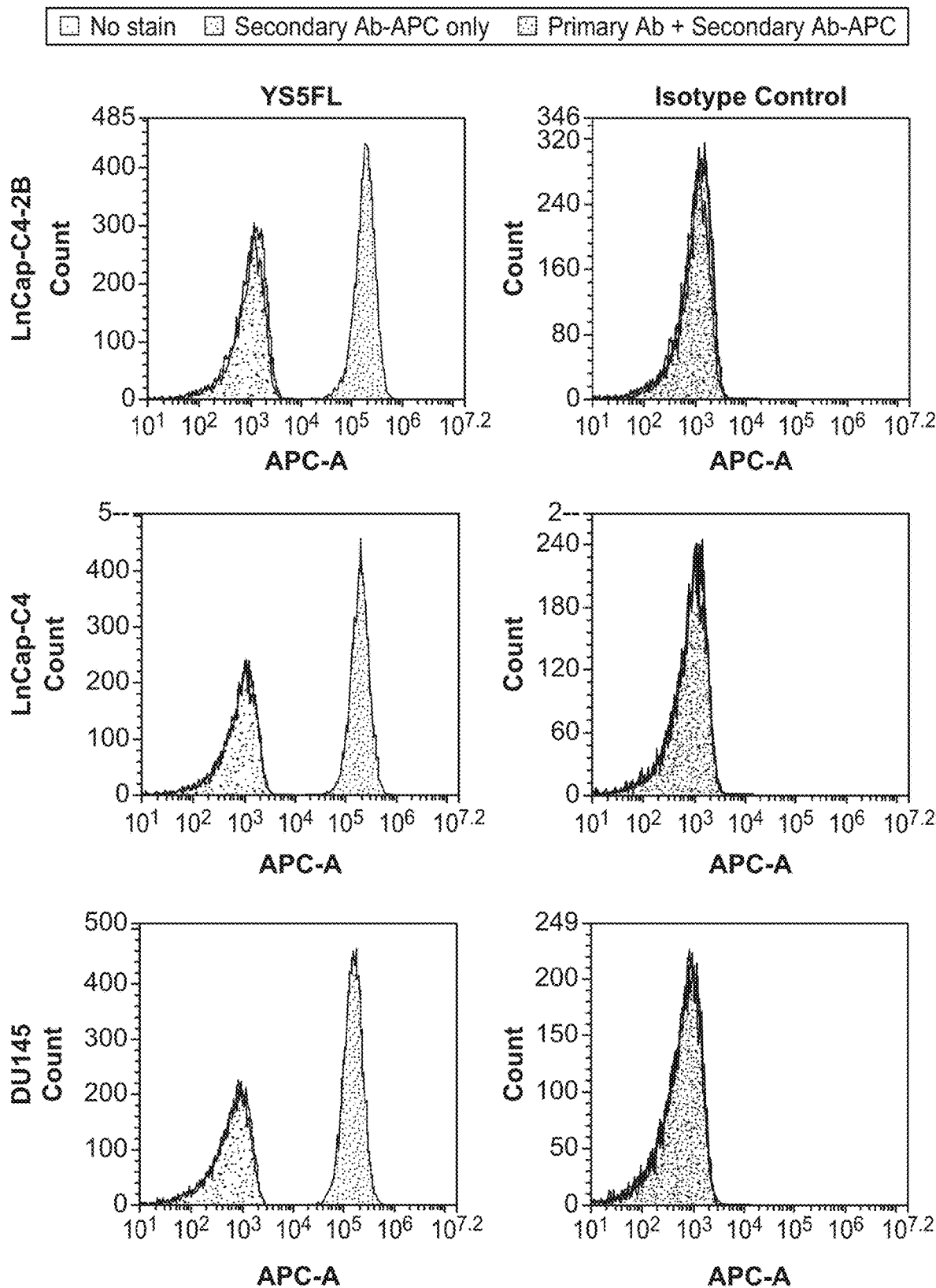
FIG. 1 depicts flow cytometry traces showing YS5FL binding to prostate cells.
Figure 1:
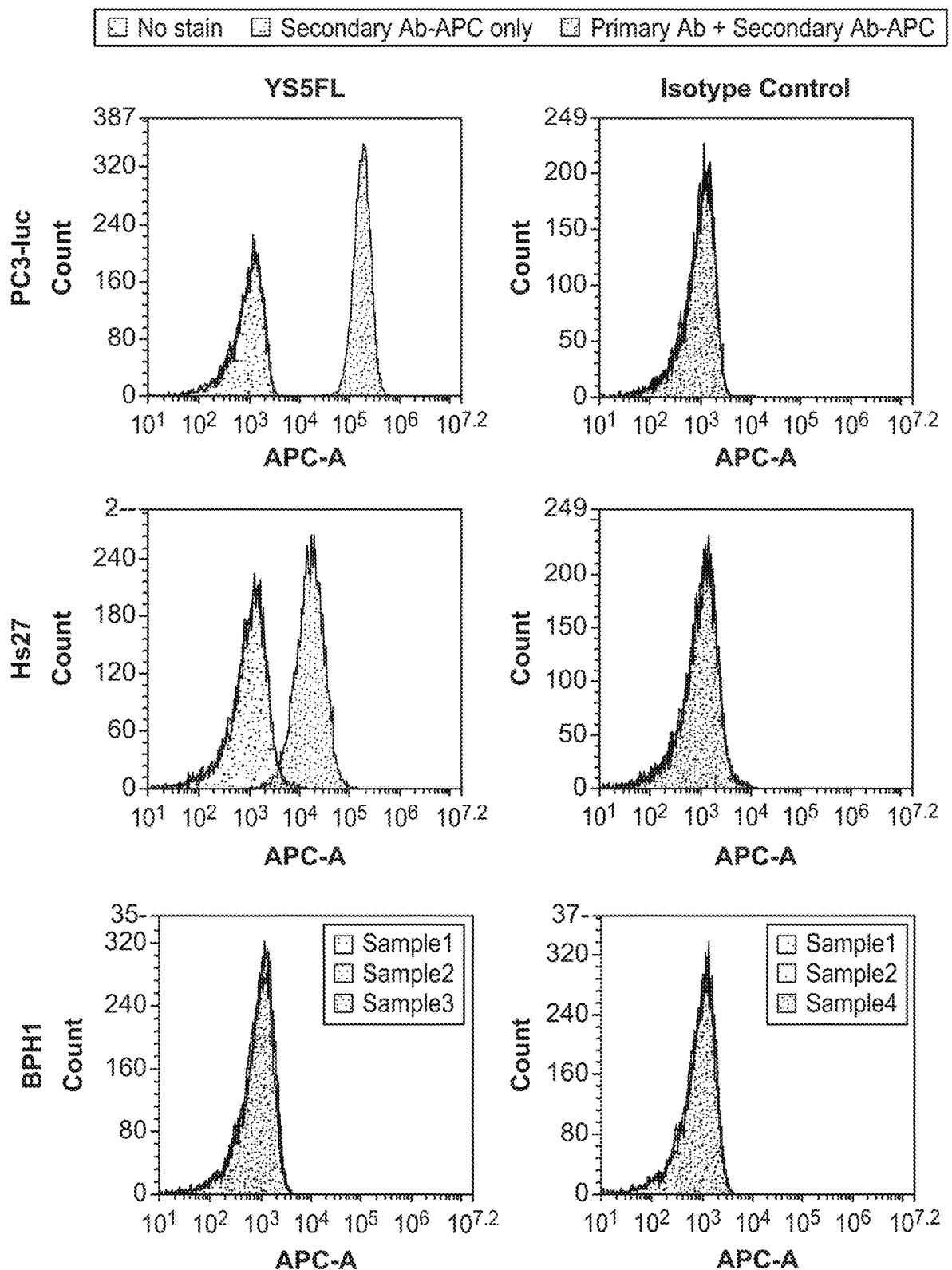

CD46, also known as CD46 complement regulatory protein, cluster of differentiation 46 and membrane cofactor protein, is an inhibitory complement receptor. Overexpression of CD46 has been observed in several cancers, such as breast cancer, colorectal cancer, liver cancer, lung cancer, or prostate cancer. In some cases, overexpression of CD46 has been characterized as a negative prognostic factor. For example, overexpression of CD46 has been correlated with shorter progression-free time and shorter overall survival time in breast cancer patients and ovarian cancer patients. Provided herein are antibodies and immunoconjugates targeting CD46 for the treatment of cancer. Further provided herein are specific dosing and administration regimes for administering the CD46 targeting antibodies and immunoconjugates to human subjects in need thereof. Further provided herein are formulations of CD46 targeting antibodies and immunoconjugates for administration to a subject in need thereof, that provide e.g., sufficient stability, cryoprotection etc.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. The section headings used herein are for organizational purposes only and are not to be construed as limiting the subject matter described. In this application, the use of the singular includes the plural unless specifically stated otherwise. It is noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The terms "antibody" and "immunoglobulin" are used interchangeably herein and are used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The terms "monoclonal antibody" and "mAb" are used interchangeably herein and refer to an antibody obtained from a substantially homogeneous population of antibodies, i.e., the individual antibodies of the population are identical except for possible naturally occurring mutations that may be present in minor amounts.

The terms "native antibodies" and "native immunoglobulins" are heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "hypervariable region," as used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest Fifth Edition, U.S. Department of Health and Human Services, NIH Publication No. 91-3242 (referred to herein as "Kabat et al") and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Chothia and Lesk, (1987) J. Mol. Biol., 196:901-917). "Framework" or "FR" residues are those variable domain residues other than the hypervariable region residues, as herein deemed.

In some instances, the CDRs of an antibody is determined according to (i) the Kabat numbering system Kabat et al. (1991) Sequences of Proteins of Immunological Interest Fifth Edition, U.S. Department of Health and Human Services, NIH Publication No. 91-3242; or (ii) the Chothia numbering scheme, which will be referred to herein as the "Chothia CDRs" (see, e.g., Chothia and Lesk, 1987, J. Mol. Biol., 196:901-917; AI-Lazikani et al., 1997, J. Mol. Biol., 273:927-948; Chothia et al., 1992, J. Mol. Biol., 227:799-817; Tramontano A et al., 1990, J. Mol. Biol. 215(1): 175-82; and U.S. Pat. No. 7,709,226); or (iii) the ImMunoGeneTics (IMGT) numbering system, for example, as described in Lefranc, M.-P., 1999, The Immunologist, 7: 132-136 and Lefranc, M.-P. et al, 1999, Nucleic Acids Res., 27:209-212 ("IMGT CDRs"); or (iv) MacCallum et al, 1996, J. Mol. Biol., 262:732-745. See also, e.g., Martin, A., "Protein Sequence and Structure Analysis of Antibody Variable Domains," in Antibody Engineering, Kontermann and Diibel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35 A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

As used herein, the term "antigen-binding site" refers to the part of the antigen binding molecule that specifically binds to an antigenic determinant. More particularly, the term "antigen-binding site" refers the part of an antibody that comprises the area which specifically binds to and is complementary to part or all of an antigen. Where an antigen is large, an antigen binding molecule may only bind to a particular part of the antigen, which part is termed an epitope. An antigen-binding site may be provided by, for example, one or more variable domains (also called variable regions). Preferably, an antigen-binding site comprises an antibody light chain variable region (VL) and an antibody heavy chain variable region (VH).

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 M, 100 nM, ≤10 nM, ≤1 nM, ≤0.1 nM, ≤0.01 nM, or ≤0.001 nM (e.g. 10-7 M or less, e.g. from 10-7M to 10-13 M, e.g. from 10-9 M to 10-13 M).

Depending on the amino acid sequence of the constant domain of their heavy chains, immunoglobulins can be assigned to different classes. There are five major classes of human immunoglobulins: IgA, IgD, IgE, IgG, IgM, and IgY, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity. The light chains of antibodies (immunoglobulins) from any vertebrate species can be assigned to one of two clearly distinct types, called kappa (κ) and lambda (λ), based on the amino acid sequences of their constant domains.

The term "chimeric antibody," as used herein refers to an antibody in which a portion of the heavy and/or light chain is derived from a particular source (e.g., protein) or species, while the remainder of the heavy and/or light chain is derived from a different source (e.g., protein) or species.

The term "recombinant human antibody," as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. In some cases, the recombinant human antibodies have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The term "valent" as used herein denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. The bispecific antibodies according to the invention are at least "bivalent" and may be "trivalent" or "multivalent" (e.g. "tetravalent" or "hexavalent"). In a particular aspect, the antibodies of the present invention have two or more binding sites and are bispecific. That is, the antibodies may be bispecific even in cases where there are more than two binding sites (i.e. that the antibody is trivalent or multivalent). In particular, the invention relates to bispecific bivalent antibodies, having one binding site for each antigen they specifically bind to.

The term "monospecific" antibody as used herein denotes an antibody that has one or more binding sites each of which bind to the same epitope of the same antigen.

The terms "individual(s)", "subject(s)" and "patient(s)" are used interchangeably herein and refer to any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The terms "cancer" and "tumor" are used interchangeably herein, encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

As used herein, "ideal body weight" ("IBW") is 50 kg+2.3 kg×(Actual height—60 in) for males and 45.5 kg+2.3 kg×(Actual height—60 in) for females.

As used herein, "adjusted body weight" ("AJBW") is IBW+0.4×(Actual weight—IBW).

Anti-CD46 Recombinant Antibodies

In some embodiments, disclosed herein is a recombinant antibody (or antigen binding fragment thereof) that specifically binds CD46. In some embodiments, antibody or antigen binding fragment or variant thereof is a monoclonal antibody. In some embodiments, antibody or antigen binding fragment or variant thereof is a human antibody, a murine antibody, a humanized antibody, or a chimeric antibody. In some embodiments, the antibody comprises or consists of a function fragment of a full length antibody (e.g., an antigen binding fragment of a full length antibody) such as a monovalent Fab, a bivalent Fab'2, a single-chain variable fragment (scFv), or functional fragment or variant thereof. In some embodiments, the recombinant antibody (or antigen binding fragment thereof) comprises an immunoglobulin variable heavy chain domain (VH). In some embodiments, the recombinant antibody (or antigen binding fragment thereof) comprises an immunoglobulin variable light chain domain (VL). In some embodiments, the recombinant antibody (or antigen binding fragment thereof) comprises a VH and a VL.

In some embodiments, the recombinant antibody (or antigen binding fragment thereof) comprises an Fc region. In some embodiments, the recombinant antibody (or antigen binding fragment thereof) is a full length antibody. In some embodiments, the recombinant antibody (or antigen binding fragment thereof) comprises a first light chain that comprises a light chain variable region and a light chain constant region; a first heavy chain that comprises a heavy chain variable region and a heavy chain constant region; a second light chain that comprises a light chain variable region and a light chain constant region; and a second heavy chain that comprises a heavy chain variable region and a heavy chain constant region. In some embodiments, the first and second light chains have at least 95%, 96%, 97%, 98%, 99%, or 100% sequence identity. In some embodiments, the first and second light chains bind the same epitope. In some embodiments, the first and second heavy chains have at least 95%, 96%, 97%, 98%, 99%, or 100% sequence identity. In some embodiments, the first and second heavy chains bind the same epitope.

In some embodiments, the recombinant antibody (or antigen binding fragment thereof) is derived from non-human (e.g. rabbit or mouse) antibodies. In some instances, the humanized form of the non-human antibody contains a minimal non-human sequence to maintain original antigenic specificity. In some cases, the humanized antibodies are human immunoglobulins (acceptor antibody), wherein the CDRs of the acceptor antibody are replaced by residues of the CDRs of a non-human immunoglobulin (donor antibody), such as rat, rabbit, or mouse donor having the desired specificity, affinity, avidity, binding kinetics, and/or capacity. In some instances, one or more framework region (FR) residues of the human immunoglobulin are replaced by corresponding non-human residues of the donor antibody.

Complementarity Determining Regions (CDRs)

In some embodiments, the CD46 binding recombinant antibody comprises an immunoglobulin variable heavy chain domain (VH) that comprises at least one, two, or three complementarity determining regions (CDRs) disclosed in Table 1 or a sequence substantially identical thereto (e.g., a sequence that has at least 90%, 95%, 96%, 97%, 98%, or 99% sequence identity).

In some embodiments, the CD46 binding recombinant antibody comprises an immunoglobulin variable light chain domain (VL) that comprises at least one, two, or three complementarity determining regions (CDRs) disclosed in Table 2 or a sequence substantially identical thereto (e.g., a sequence that has at least 90%, 95%, 96%, 97%, 98%, or 99% sequence identity).

In some embodiments, the CD46 binding recombinant antibody comprises a VH that comprises at least one, two, or three complementarity determining regions (CDRs) disclosed in Table 1 or a sequence substantially identical thereto (e.g., a sequence that has at least 90%, 95%, 96%, 97%, 98%, or 99% sequence identity); and a VL that comprises at least one, two, or three complementarity determining regions (CDRs) disclosed in Table 2 or a sequence substantially identical thereto (e.g., a sequence that has at least 90%, 95%, 96%, 97%, 98%, or 99% sequence identity).

In some embodiments, the CD46 binding recombinant antibody comprises a VH that comprises a CDR1 of SEQ ID NO: 1, a CDR2 of SEQ ID NO: 2, and a CDR3 of SEQ ID NO: 3.

In some embodiments, the CD46 binding recombinant antibody comprises a VL that comprises a CDR1 of SEQ ID NO: 4, a CDR2 of SEQ ID NO: 5, and a CDR3 of SEQ ID NO: 6.

In some embodiments, the CD46 binding recombinant antibody comprises a VH that comprises a CDR1 of SEQ ID NO: 1, a CDR2 of SEQ ID NO: 2, and a CDR3 of SEQ ID NO: 3; and a VL that comprises a CDR1 of SEQ ID NO: 4, a CDR2 of SEQ ID NO: 5, and a CDR3 of

TABLE 1

VH CDR amino acid sequences of anti-CD46 antibodies as defined by Kabat et al.

| Antibody | SEQ ID NO | CDR1 | SEQ ID NO | CDR2 | SEQ ID NO | CDR3 |
|---|---|---|---|---|---|---|
| YS5FL | 1 | GLTVNNYA | 2 | ISYDGNNK | 3 | AKGGGYFDL |

TABLE 2

VL CDR amino acid sequences of anti-CD46 antibodies as defined by Kabat et al.

| Antibody | SEQ ID NO | CDR1 | SEQ ID NO | CDR2 | SEQ ID NO | CDR3 |
|---|---|---|---|---|---|---|
| YS5FL | 4 | SSNIGAGYD | 5 | GNN | 6 | SSYTSGTWL |

In some embodiments, a CDR described herein comprises one, two, or three amino acid modifications. In some embodiments, said modification is a substitution, addition, or deletion. In some embodiments, a CDR described herein comprises one, two, or three conservative amino acid substitutions. In some embodiments, the one, two, or three amino acid modifications does not substantially modify binding to human CD46. In some embodiments, the one, two, or three amino acid modifications modifies binding to human CD46. In some embodiments, a VH-CDR3 and/or VL-CDR3 comprises an amino acid substitution that modifies binding to human CD46, immunogenicity, or some other feature. In some embodiments, the amino acid substitution is an alanine (A).

Variable Heavy and Variable Light Regions

In some embodiments, the CD46 binding recombinant antibody comprises a VH that comprises an amino acid sequence disclosed in Table 3 or a sequence substantially identical thereto (e.g., a sequence that has at least 90%, 95%, 96%, 97%, 98%, or 99% sequence identity).

In some embodiments, the CD46 binding recombinant antibody comprises a VL that comprises an amino acid sequence disclosed in Table 4 or a sequence substantially identical thereto (e.g., a sequence that has at least 90%, 95%, 96%, 97%, 98%, or 99% sequence identity).

In some embodiments, the CD46 binding recombinant antibody comprises a VH that comprises an amino acid sequence disclosed in Table 3 or a sequence substantially identical thereto (e.g., a sequence that has at least 90%, 95%, 96%, 97%, 98%, or 99% sequence identity); and a VL that comprises an amino acid sequence disclosed in Table 4 or a sequence substantially identical thereto (e.g., a sequence that has at least 90%, 95%, 96%, 97%, 98%, or 99% sequence identity).

In some embodiments, the CD46 binding recombinant antibody comprises a VH that comprises an amino acid sequence of SEQ ID NO: 7, or a sequence substantially identical thereto (e.g., a sequence that has at least 90%, 95%, 96%, 97%, 98%, or 99% sequence identity).

In some embodiments, the CD46 binding recombinant antibody comprises a VL that comprises an amino acid sequence of SEQ ID NO: 8, or a sequence substantially identical thereto (e.g., a sequence that has at least 90%, 95%, 96%, 97%, 98%, or 99% sequence identity).

In some embodiments, the CD46 binding recombinant antibody comprises a VH that comprises an amino acid sequence of SEQ ID NO: 7, or a sequence substantially identical thereto (e.g., a sequence that has at least 90%, 95%, 96%, 97%, 98%, or 99% sequence identity); and a VL that comprises an amino acid sequence of SEQ ID NO: 8, or a sequence substantially identical thereto (e.g., a sequence that has at least 90%, 95%, 96%, 97%, 98%, or 99% sequence identity).

TABLE 3

Amino acid sequence of the anti-CD46 variable heavy chain binding domains.

| Name | SEQ ID NO | Amino Acid Sequence |
|---|---|---|
| YS5FL | 7 | QVQLVQSGGGVVQPGRSLRLACAASGLTVNNYAM HWVRQAPGKGLEWVAVISYDGNNKYYADSVKGRF TISRDNSKNTLYLQMNSLRAEDTAVYYCAKGGGY FDLWGRGTLVTVSS |

TABLE 4

Amino acid sequence of the anti-CD46 variable light chain binding domains.

| Name | SEQ ID NO | Amino Acid Sequence |
|---|---|---|
| YS5FL | 8 | QSVLTQPPSVSGAPGQRVTISCTGSSSNIGAGYDVHW YQQLPGTAPKLLIYGNNNRPSGVPDRFSGSKSGTSAS LAITGLQAEDEADYYCSSYTSGTWLFGGGTKLTVL |

Heavy Chain and Light Chains

In some embodiments, the CD46 binding recombinant antibody comprises a heavy chain that comprises an amino acid sequence disclosed in Table 5 or a sequence substantially identical thereto (e.g., a sequence that has at least 90%, 95%, 96%, 97%, 98%, or 99% sequence identity).

In some embodiments, the CD46 binding recombinant antibody comprises a light chain that comprises an amino acid sequence disclosed in Table 6 or a sequence substantially identical thereto (e.g., a sequence that has at least 90%, 95%, 96%, 97%, 98%, or 99% sequence identity).

In some embodiments, the CD46 binding recombinant antibody comprises a heavy chain that comprises an amino acid sequence disclosed in Table 5 or a sequence substantially identical thereto (e.g., a sequence that has at least 90%, 95%, 96%, 97%, 98%, or 99% sequence identity); and a light chain that comprises an amino acid sequence disclosed in Table 6 or a sequence substantially identical thereto (e.g., a sequence that has at least 90%, 95%, 96%, 97%, 98%, or 99% sequence identity).

In some embodiments, CD46 binding recombinant antibody comprises a heavy chain that comprises an amino acid sequence of SEQ ID NO: 9, or a sequence substantially identical thereto (e.g., a sequence that has at least 90%, 95%, 96%, 97%, 98%, or 99% sequence identity).

In some embodiments, the CD46 binding recombinant antibody comprises a light chain that comprises an amino acid sequence of SEQ ID NO: 10, or a sequence substantially identical thereto (e.g., a sequence that has at least 90%, 95%, 96%, 97%, 98%, or 99% sequence identity).

In some embodiments, the CD46 binding recombinant antibody comprises a heavy chain that comprises an amino acid sequence of SEQ ID NO: 9, or a sequence substantially identical thereto (e.g., a sequence that has at least 90%, 95%, 96%, 97%, 98%, or 99% sequence identity); and a light chain that comprises an amino acid sequence of SEQ ID NO: 10, or a sequence substantially identical thereto (e.g., a sequence that has at least 90%, 95%, 96%, 97%, 98%, or 99% sequence identity).

TABLE 5

Amino acid sequence of the anti-CD46 heavy chain.

| Name | SEQ ID NO | Amino Acid Sequence |
|---|---|---|
| YS5FL | 9 | QVQLVQSGGGVVQPGRSLRLACAASGLTVNNYAMHWVRQAPGK GLEWVAVISYDGNNKYYADSVKGRFTISRDNSKNTLYLQMNSL RAEDTAVYYCAKGGGYFDLWGRGTLVTVSSASTKGPSVFPLAP SSKSTSGGTAALGCLVKDYFPEPVTVSWNSGALTSGVHTFPAV LQSSGLYSLSSVVTVPSSSLGTQTYICNVNHKPSNTKVDKKVE PKSCDKTHTCPPCPAPELLGGPSVFLFPPKPKDTLMISRTPEV TCVVVDVSHEDPEVKFNWYVDGVEVHNAKTKPREEQYNSTYRV VSVLTVLHQDWLNGKEYKCKVSNKALPAPIEKTISKAKGQPRE PQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK |

TABLE 6

Amino acid sequence of the anti-CD46 light chain.

| Name | SEQ ID NO | Amino Acid Sequence |
|---|---|---|
| YS5FL | 10 | QSVLTQPPSVSGAPGQRVTISCTGSSSNIGAGYDVHWYQ QLPGTAPKLLIYGNNNRPSGVPDRFSGSKSGTSASLAIT GLQAEDEADYYCSSYTSGTWLFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS |

In some embodiments, the anti-CD46 antibody disclosed herein comprises an immunoglobulin constant region (e.g., an Fc region). Exemplary Fc regions can be chosen from the heavy chain constant regions of IgG1, IgG2, IgG3, or IgG4; more particularly, the heavy chain constant region of human IgG1 or IgG4. In some embodiments, the immunoglobulin constant region (e.g., the Fc region) is altered, e.g., mutated, to increase or decrease one or more of: Fc receptor binding, antibody glycosylation, the number of cysteine residues, effector cell function, or complement function.

Effector Agents

In some embodiments, disclosed herein are immunoconjugates that comprise an anti-CD46 antibodies attached to an effector agent (or prodrug thereof). In some embodiments, the effector agent is a drug (or prodrug thereof), small molecule, protein, peptide, antibody, ligand, receptor, cytotoxic agent, cytostatic agent, liposome, nanoparticle, radionuclide, cytokine, chemokine, a toxin, a detectable label, a viral particle, or a chelate.

In some embodiments, the effector agent is a drug (or prodrug thereof). In some embodiments, the effector agent is an anti-cancer agent (or prodrug thereof). In some embodiments, the effector agent is a chemotherapeutic agent (or prodrug thereof). In some embodiments, the effector agent is a microtubule inhibitor (or prodrug thereof), a DNA-damaging agent (or prodrug thereof), or a polymerase inhibitor (or prodrug thereof).

In some embodiments, the effector agent is a microtubule inhibitor (or prodrug thereof). In some embodiments, the microtubule inhibitor is an auristatin (or a derivative thereof), dolastatin-10 (or a derivative thereof), or maytansine (or a derivative thereof). In some embodiments, the microtubule inhibitor is monomethylauristatin F (MMAF), auristatin E (AE), monomethylauristatin E (MMAE), valine-citrulline MMAE (vcMMAE), or valine-citrulline MMAF (vcMMAF). In some embodiments, the microtubule inhibitor is monomethylauristatin E (MMAE).

In some embodiments, the effector agent comprises or consists of a compound of Formula A:

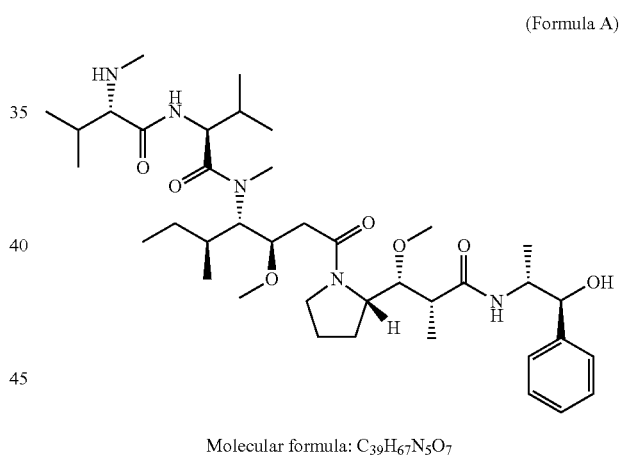

(Formula A)

Molecular formula: $C_{39}H_{67}N_5O_7$

In certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments of the present invention, gamma-emitters, positron-emitters, x-ray emitters, and fluorescence-emitters are suitable for localization, diagnosis and/or staging, and/or therapy, while beta and alpha-emitters and electron and neutron-capturing agents, such as boron and uranium, also can be used for therapy.

Immunoconjugates

In one aspect, provided herein are immunoconjugates comprising an anti-CD46 antibody and an effector agent. In some embodiments, the methods described herein utilize these immunoconjugates.

In some embodiments, the immunoconjugate comprises an anti-CD46 antibody (or antigen binding fragment thereof) described herein. In some embodiments, the immunoconjugate comprises a YS5FL antibody (or antigen binding fragment thereof).

In some embodiments, the effector agent is conjugated to the anti-CD46 antibody. In some embodiments, the effector agent is attached to the anti-CD46 antibody via a liker. In some embodiments, the linker is a peptide linker, a small molecule linker, or a linker that comprises a peptide and a small molecule. Exemplary peptide linkers include, but are not limited to, peptide linkers comprising glycine, serine, or glycine and serine.

In some embodiments, the linker is cleavable. In some embodiments, the linker is cleaved only upon internalization into a cell. In some embodiments, the cleavable linker is only cleavable upon internalization into a cancer cell. In some embodiments, the cleavable portion of a linker is a peptide (e.g., a dipeptide, e.g., ValCit). In some embodiments, the cleavable linker is cleavable by cathepsin. In some embodiments, the linker comprises maleimide. In some embodiments, the linker comprises caproic acid. In some embodiments, the linker comprises maleimide and caproic acid. In some embodiments, the linker comprises maleimide, caproic acid, and a cleavable dipeptide.

In some embodiments, the linker comprises or consists of is a maleimidocaproyl-valine-citrulline-para-amino benzyloxycarbonyl (mc-vc-PAB).

In some embodiments, the linker comprises or consists of a compound of Formula B:

ments, an anti-CD46 antibody is partially reduced prior to conjugation to an effector moiety such that 1-4 interchain disulfide bonds are reduced while intrachain disulfide bonds are not reduced. Partial reduction exposes pairs of cysteine residues, rendering them accessible to conjugation to adducts such as mc-vc-PAB-MMAE. In some embodiments, the following interchain cysteine pairs of YS5FL are exposed: C219 of the first heavy chain and C214 of the first light chain; C219 of the second heavy chain and C214 of the second light chain; C225 of the first heavy chain and C225 of the second heavy chain; and C228 of the first heavy chain and C228 of the second heavy chain. In some embodiments, an effector such as mc-vc-PAB-MMAE is conjugated to 0, 1, 2, 3, or 4 pairs of cysteine residues on YS5FL.

In some embodiments, the ratio of effector agents to anti-CD46 antibodies is c. In some embodiments, the ratio of effector agents to anti-CD46 antibodies is 2:1, 4:1, 6:1, or 8:1. In some embodiments, the ratio of effector agents to anti-CD46 antibodies is about 4:1. In some embodiments, the average ratio of effector agents to anti-CD46 antibodies is about 3.7:1. In some embodiments, if the immunoconjugate comprises 2 or more effector agents, each effector agent is the same. In some embodiments, if the immunoconjugate comprises 2 or more effector agents, at least two effector agents are different. In some embodiments, the ratio of effector agents to anti-CD46 antibodies is about 4:1 and each effector agent is the same.

Exemplary Immunoconjugate

An exemplary immunoconjugate provided herein comprises an anti-CD46 YS5FL antibody linked to a monomethyl auristatin E (MMAE) effector agent via a maleimido-

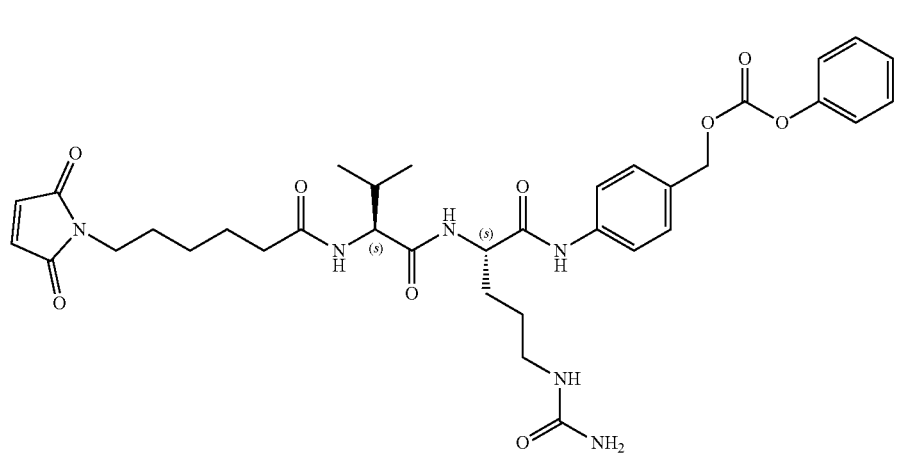

(Formula B)

In some embodiments, an effector agent is attached to a light chain of the anti-CD46 antibody. In some embodiments, an effector agent is attached to a light chain constant region of the anti-CD46 antibody. In some embodiments, an effector agent is attached to a heavy chain of the anti-CD46 antibody. In some embodiments, an effector agent is attached to a heavy chain constant region of the anti-CD46 antibody.

In some embodiments, an effector moiety is attached to a cysteine residue of the anti-CD46 antibody. In some embodicaproyl-valine-citrulline-para-amino benzyloxycarbonyl (mc-vc-PAB). In some embodiments, the ratio of MMAE to YSFL antibody is about 4:1.

In some embodiments, the immunoconjugate comprises the antibody conjugate below in Formula C, wherein the comprises heavy chain of SEQ ID NO: 9; and a light chain of SEQ ID NO: 10. This immunoconjugate is also referred to herein as FOR46 and comprises YS5FL antibody attached to MMAE through a mc-vc-PAB linker.

Formula C

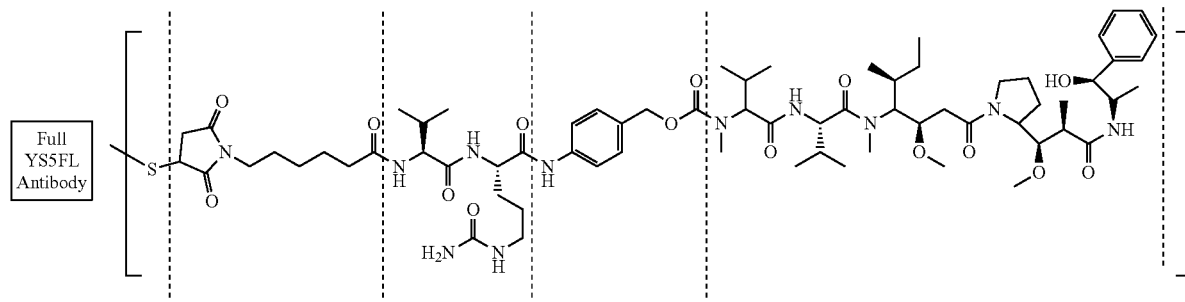

In some embodiments, an anti-CD46 immunoconjugate described herein is manufactured by a process comprising reduction or partial reduction of disulfide bonds of an immunoglobulin. In some embodiments, an anti-CD46 immunoconjugate described herein is manufactured by a process comprising reduction or partial reduction of interchain disulfide bonds of an immunoglobulin. In some embodiments, the reducing agent is dithiothreitol (DTT) or tris(2-carboxyethyl)phosphine (TCEP). In some embodiments, an effector-linker complex comprising a maleimide reactive group is conjugated to pairs of reduced cysteines of an immunoglobulin. In some embodiments, the effector-linker complex is mc-vc-PAB-MMAE.

In some embodiments, an effector-linker complex is conjugated at C219, C225, or C228 of a YS5FL heavy (SEQ ID NO: 9) or C214 of a YS5FL light chain (SEQ ID NO: 10), or any combination thereof. In some embodiments, the effector-linker complexes are conjugated to C219 of a YS5FL heavy chain and C214 of a YS5FL light chain. In some embodiments, an anti-CD46 immunoconjugate comprises two YS5FL heavy chains and two YS5FL light chains and effector-linker complexes are conjugated to C219 of a YS5FL first heavy chain, C214 of a first YS5FL light chain, C219 of a YS5FL second heavy chain, and C214 of a second YS5FL light chain. In some embodiments, an anti-CD46 immunoconjugate comprises two YS5FL heavy chains and an effector-linker complex is conjugated to C225 of a first YS5FL heavy chain and C225 of a second YS5FL heavy chain. In some embodiments, an anti-CD46 immunoconjugate comprises two YS5FL heavy chains and an effector-linker complex is conjugated to C228 of a first YS5FL heavy chain and C228 of a second YS5FL heavy chain. In some embodiments, an immunoconjugate comprises two, four, six, or eight effectors and the effectors are conjugated to any one, two, three, or four, respectively, of the following pairs of cysteines: C219 of HC1 and C214 of LC1; C219 of HC2 and C214 of LC2; C225 of HC1 and C225 of HC2; and C228 of HC1 and C228 of HC2.

Immunoconjugate Binding to Target Cells and Activity on Target Cells

In some embodiments, an anti-CD46 antibody or immunoconjugate described herein binds to CD46 expressed on the surface of a target cell (e.g., a cancer cell) and is internalized by the cell. In some embodiments, the antibody or immunoconjugate is internalized into the target cell via macropinocytosis. In some embodiments, the antibody or immunoconjugate is targeted to a lysosome of the cell upon internalization. In some embodiments, the antibody or immunoconjugate induces internalization into the cell without crosslinking.

In some embodiments, an anti-CD46 antibody or immunoconjugate described herein mediates killing of a target cell (e.g., cancer cell) upon internalization. In some embodiments, the anti-CD46 antibody or immunoconjugate induces apoptosis of the target cell (e.g., cancer cell) upon internalization. In some embodiments, the anti-CD46 antibody or immunoconjugate inhibits cell division of the target cell (e.g., cancer cell) upon internalization. In some embodiments, the anti-CD46 antibody or immunoconjugate selectively inhibits cell division of cancer cells upon internalization and does not inhibit cell division of non-cancer cells upon internalization.

Production of Antibodies or Antigen Binding Fragments Thereof

In some embodiments, antibodies (and antigen binding fragment thereof) are produced using any method known in the art to be useful for the synthesis of antibodies, in particular, by chemical synthesis or by recombinant expression techniques.

In some embodiments, an antibody (or antigen binding fragment thereof) is expressed recombinantly. In some embodiment, the nucleic acid encoding the antibody (or antigen binding fragment thereof) is assembled from chemically synthesized oligonucleotides. In some embodiments, a nucleic acid molecule encoding an antibody is generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some embodiments, an antibody (or antigen binding fragment thereof) is made by immunizing an animal, such as a mouse, to generate polyclonal or monoclonal antibodies.

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In some embodiments, the expression of the antibody is regulated by a constitutive, an inducible or a tissue, specific promoter.

A variety of host-expression vector systems can be utilized to express an antibody (or antigen binding fragment thereof) described herein. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression may be preferred. In some embodiments, cell lines that stably express an antibody are made. Following the introduction of the foreign DNA, engineered cells are then allowed to grow for 1-2 days in an enriched media, and then are switched to a selective media. A selectable marker in the recombinant plasmid may be used to confer resistance to the selection.

In some embodiments, any method known in the art for purification of an antibody can be used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

Vectors can include any suitable vector derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichia pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4, vector or MCS vector.

Examples of mammalian vectors include transient expression vectors or stable expression vectors. Mammalian transient expression vectors may include pRK5, p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

A host cell can be any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell, or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes, or Tenericutes. In some cases, gram-negative bacteria include Aquificae, Deinococcus-Thermus, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria, or Thermotogae. A bacterial cell can be *Escherichia coli, Clostridium botulinum*, or Coli bacilli.

Exemplary prokaryotic host cells include, but are not limited to, BL21, Mach 1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces* cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-*Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid, or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Therapeutic Methods

In one aspect, provided herein are methods of treating cancer by administering an anti-CD46 antibody or immunoconjugate described herein.

In some embodiments, the cancer is multiple myeloma. In some embodiments, the cancer is relapsing multiple myeloma. In some embodiments, the cancer is remitting multiple myeloma. In some embodiments, the cancer is relapsing or remitting multiple myeloma.

In some embodiments, the cancer is prostate cancer. In some embodiments, the cancer is castration resistant prostate cancer. In some embodiments, the cancer is metastatic prostate cancer.

In one aspect, provided herein are anti-CD46 antibodies or immunoconjugates described herein for use as a medicament are provided. In one aspect, provided herein are anti-CD46 antibodies or immunoconjugates described herein for use in treating a disease, in particular for use in the treatment of cancer, are provided. In one aspect, provided herein are anti-CD46 antibodies or immunoconjugates described herein for use in a method of treating cancer are provided. In one aspect, provided herein are anti-CD46 antibodies or immunoconjugates described herein for use in the treatment of a disease in an individual in need thereof. In one aspect, provided herein are anti-CD46 antibodies or immunoconjugates described herein for use in a method of treating an individual having cancer comprising administering to the individual a therapeutically effective amount of anti-CD46 antibodies or immunoconjugates described herein. In one aspect, provided herein are anti-CD46 antibodies or immunoconjugates described herein before in the manufacture or preparation of a medicament for the treatment of a disease in an individual in need thereof. In one aspect, provided herein are the medicament is for use in a method of treating a cancer comprising administering to an individual having cancer a therapeutically effective amount of the medicament.

Dosing and Administration

For use in therapeutic methods, anti-CD46 antibodies or immunoconjugates described herein can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In some embodiments, an antibody or immunoconjugate described herein is administered to a human subject via intravenous infusion. In some embodiments, the antibody or immunoconjugate is administered to a human subject every 7 days, every 14 days, every 18 days, every 21 days, or every 30 days. In some embodiments, the antibody or immunoconjugate is administered to a human subject every 21 days.

In some embodiments, the antibody or immunoconjugate is administered to a human subject at a dose from about 1.0 to about 5.0 mg/kg. In some embodiments, the antibody or immunoconjugate to at a dose from about 1.0 to about 4.5 mg/kg, about 1.0 to about 4.0 mg/kg, about 1.0 to about 3.5 mg/kg, about 1.0 to about 3.0 mg/kg, about 1.0 to about 2.7 mg/kg, about 1.0 to about 2.5 mg/kg, about 1.0 to about 2.4 mg/kg, about 1.5 to about 4.5 mg/kg, about 1.5 to about 4.0 mg/kg, about 1.5 to about 3.5 mg/kg, about 1.5 to about 3.0 mg/kg, about 1.5 to about 2.7 mg/kg, about 1.5 to about 2.5 mg/kg, about 1.5 to about 2.4 mg/kg, about 1.5 to about 2.0 mg/kg, about 1.8 to about 4.5 mg/kg, about 1.8 to about 4.0 mg/kg, about 1.8 to about 3.5 mg/kg, about 1.8 to about 3.0 mg/kg, about 1.8 to about 2.7 mg/kg, about 1.8 to about 2.5 mg/kg, about 1.8 to about 2.4 mg/kg, or about 1.8 to about 2.0 mg/kg. In some embodiments, the antibody or immunoconjugate is administered to a human subject at a dose from about 1.5 to about 2.5 mg/kg. In some embodiments, the antibody or immunoconjugate is administered to a human subject at a dose from about 1.2 to about 3.0 mg/kg.

In some embodiments, the antibody or immunoconjugate is administered to a human subject at a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0 mg/kg. In some embodiments, the antibody or immunoconjugate is administered to a human subject at a dose of about 1.8, about 2.4, about 2.7, about 3.0, or about 3.2 mg/kg. In some embodiments, the antibody or immunoconjugate is administered to a human subject at a dose of about 1.8 mg/kg. In some embodiments, the antibody or immunoconjugate is administered to a human subject at a dose of about 2.4 mg/kg. In some embodiments, the antibody or immunoconjugate is administered to a human subject at a dose of about 2.7 mg/kg. In some embodiments, the antibody or immunoconjugate is administered to a human subject at a dose of about 3.0 mg/kg. In some embodiments, the antibody or immunoconjugate is administered to a human subject at a dose of about 3.2 mg/kg. In some embodiments, the antibody or immunoconjugate is administered to a human subject at a dose of about 1.5 mg/kg. In some embodiments, the antibody or immunoconjugate is administered to a human subject at a dose of about 2.5 mg/kg. In some embodiments, the antibody or immunoconjugate is administered to a human subject at a dose of about 3.0 mg/kg. In some embodiments, weight is measured in kg. In some embodiments, the weight of the human subject is an actual body weight. In some embodiments, weight is measured in kg. In some embodiments, the weight of the human subject is an adjusted body weight (AJBW).

Determining CD46 Expression

In one aspect, provided herein are methods of treating a cancer in a subject by (1) determining that the cancer comprises CD46, and (2) administering an anti-CD46 antibody or immunoconjugate described herein. In some embodiments, a cancer that expresses CD46 is sensitive to treatment by the anti-CD46 antibody or immunoconjugate. In some embodiments, the anti-CD46 antibody or immunoconjugate is a more effective anti-cancer agent when the cancer expresses CD46 or expresses higher levels of CD46 than non-cancerous control. In some embodiments, the non-cancerous control is a matched non-cancer control tissue from the subject or an individual without cancer. For example, if the cancer is a prostate cancer, the non-cancer control tissue may be a healthy prostate.

In some embodiments, an anti-CD46 antibody is used to determine CD46 expression by the cancer. CD46 expression by a cancer (e.g. a cancer cell, a cancerous lesion, a metastatic cell) may be detected by various methods such as immunofluorescence microscopy, immunohistochemistry, or flow cytometry.

In another embodiment, the copy number of the CD46 gene is determined in the cancer. The CD46 gene is localized on the q arm of chromosome 1 at band 32 (1q32). In some embodiments, a 1q amplification indicates that CD46 is more highly expressed. In some embodiments, the 1q amplification comprises an amplification of 1q32. In some embodiments, the 1q amplification comprises an amplification of 1q21, and amplification of 1q32 is inferred from the amplification of 1q21. In some embodiments, the gene amplification comprises an increase in the copy number of the CD46 gene. In some embodiments, the copy number of the CD46 gene is 3 or more. In some embodiments, the copy number of the CD46 gene is 4, 5, 6, 7, or 8.

Pharmaceutical Compositions and Formulations

In a further aspect, the invention provides pharmaceutical compositions comprising an anti-CD46 antibody or immunoconjugate described herein, e.g., for use in any of the above therapeutic methods. In one embodiment, the pharmaceutical composition comprises an anti-CD46 antibody or immunoconjugate provided herein and at least one pharmaceutically acceptable excipient. The preparation of a pharmaceutical composition that contains an anti-CD46 antibody or immunoconjugate described herein will be known to those of skill in the art in light of the present disclosure, as exemplified by Remington's Pharmaceutical Sciences, 18th Ed. Mack Printing Company, 1990, incorporated by reference herein.

In some embodiments, the pharmaceutical composition comprises a buffer. In some embodiments, the buffer comprises histidine. In some embodiments, the pharmaceutical composition comprises from about 10 to about 40 mM, about 10 to about 30 mM, or about 10 to about 20 mM histidine buffer. In some embodiments, the pharmaceutical composition comprises about 10 mM, about 15 mM, about 20 mM, about 25 mM, about 30 mM, about 35 mM, or about 40 mM histidine buffer. In some embodiments, the pharmaceutical composition comprises about 20 mM histidine buffer.

In some embodiments, the pharmaceutical composition comprises a cryoprotectant. In some embodiments, the cryoprotectant comprises a saccharide. In some embodiments, the cryoprotectant comprises sucrose or trehalose. In some embodiments, the cryoprotectant comprises sucrose. In some embodiments, the pharmaceutical composition comprises from about 4% to about 12%, about 4% to about 11%, about 4% to about 10%, about 4% to about 9%, about 4% to about 8%, about 5% to about 12%, about 5% to about 11%, about 5% to about 10%, about 5% to about 9%, about 5% to about 8%, about 6% to about 12%, about 6% to about 11%, about 6% to about 10%, about 6% to about 9%, about 6% to about 8%, about 7% to about 12%, about 7% to about 11%, about 7% to about 10%, about 7% to about 9%, or about 7% to about 8% sucrose. In some embodiments, the pharmaceutical composition comprises about 8% sucrose.

In some embodiments, the pharmaceutical composition comprises a stabilizing agent. In some embodiments, the stabilizing agent prevents denaturation of said recombinant antibody, prevents aggregation of said immunoconjugates, or both. In some embodiments, the stabilizing agent is a polysorbate. In some embodiments, the stabilizing agent is polysorbate 20. In some embodiments, the stabilizing agent is polysorbate 80. In some embodiments, the pharmaceutical composition comprises a polysorbate (e.g., polysorbate 80) from about 0.001% to 0.1%, 0.001% to 0.05%, 0.001% to 0.04%, 0.001% to 0.03%, 0.001% to 0.02%, or 0.001% to 0.01%. In some embodiments, the pharmaceutical composition comprises a polysorbate (e.g., polysorbate 80) at about 0.01%, 0.02%, 0.03%, 0.04%, 0.05%, 0.06%, 0.07%, 0.08%, 0.09%, or 0.1%. In some embodiments, the pharmaceutical composition comprises a polysorbate (e.g., polysorbate 80) at about 0.01%.

In some embodiments, the pharmaceutical composition has a pH of from about 5.0 to about 7.0. In some embodiments, the pharmaceutical composition has a pH of about 5.0, 5.5, 6.0, 6.5, 7.0, or 7.5. In some embodiments, the pharmaceutical composition has a pH of about 6.0.

In some embodiments, pharmaceutical composition comprises an anti-CD46 antibody or immunoconjugate described herein at a concentration from about 5.0 mg/ml to 15.0 mg/ml, 5.0 mg/ml to 14.0 mg/ml, 5.0 mg/ml to 13.0 mg/ml, 5.0 mg/ml to 12.0 mg/ml, 5.0 mg/ml to 11.0 mg/ml, 5.0 mg/ml to 10.0 mg/ml, 6.0 mg/ml to 15.0 mg/ml, 7.0 mg/ml to 15.0 mg/ml, 8.0 mg/ml to 15.0 mg/ml, 9.0 mg/ml to 15.0 mg/ml, or 10.0 mg/ml to 15.0 mg/ml. In some embodiments, pharmaceutical composition comprises an anti-CD46 antibody or immunoconjugate described herein at a concentration of about 5.0 mg/ml, 6.0 mg/ml, 7.0 mg/ml, 8.0 mg/ml, 9.0 mg/ml, 10.0 mg/ml, 11.0 mg/ml, 12.0 mg/ml, 13.0 mg/ml, 14.0 mg/ml, or 15.0 mg/ml. In some embodiments, the pharmaceutical composition comprises an anti-CD46 antibody or immunoconjugate described herein at a concentration of about 5.0 mg/ml±1.0 mg/mL, 6.0 mg/ml±1.0 mg/mL, 7.0 mg/ml±1.0 mg/mL, 8.0 mg/ml±1.0 mg/mL, 9.0 mg/ml±1.0 mg/mL, 10.0 mg/ml±1.0 mg/mL, 11.0 mg/ml±1.0 mg/mL, 12.0 mg/ml±1.0 mg/mL, 13.0 mg/ml±1.0 mg/mL, 14.0 mg/ml t 1.0 mg/mL, or 15.0 mg/ml±1.0 mg/mL. In some embodiments, the pharmaceutical composition comprises an anti-CD46 antibody or immunoconjugate described herein at a concentration of about 10.0 mg/ml±1.0 mg/mL.

Exemplary Formulation

An exemplary formulation of an anti-CD46 antibody or immunoconjugate described herein comprises about an anti-CD46 antibody or immunoconjugate described herein at a concentration of about 10.0 mg/ml±1.0 mg/mL; about 20 mM histidine buffer, about 8.0% sucrose, about 0.01% polysorbate 80, pH 6.0.

Articles of Manufacture

In another aspect of the invention, an article of manufacture containing materials useful for the treatment of cancers described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating the condition and may have a sterile access port (for example the container may be an intravenous solution bag or a vial having a stopper that is pierceable by a hypodermic injection needle).

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

These examples are provided for illustrative purposes only and not to limit the scope of the claims provided herein.

Example 1: YS5FL Binding to the Surface of Cancer Cells

Figure 2:
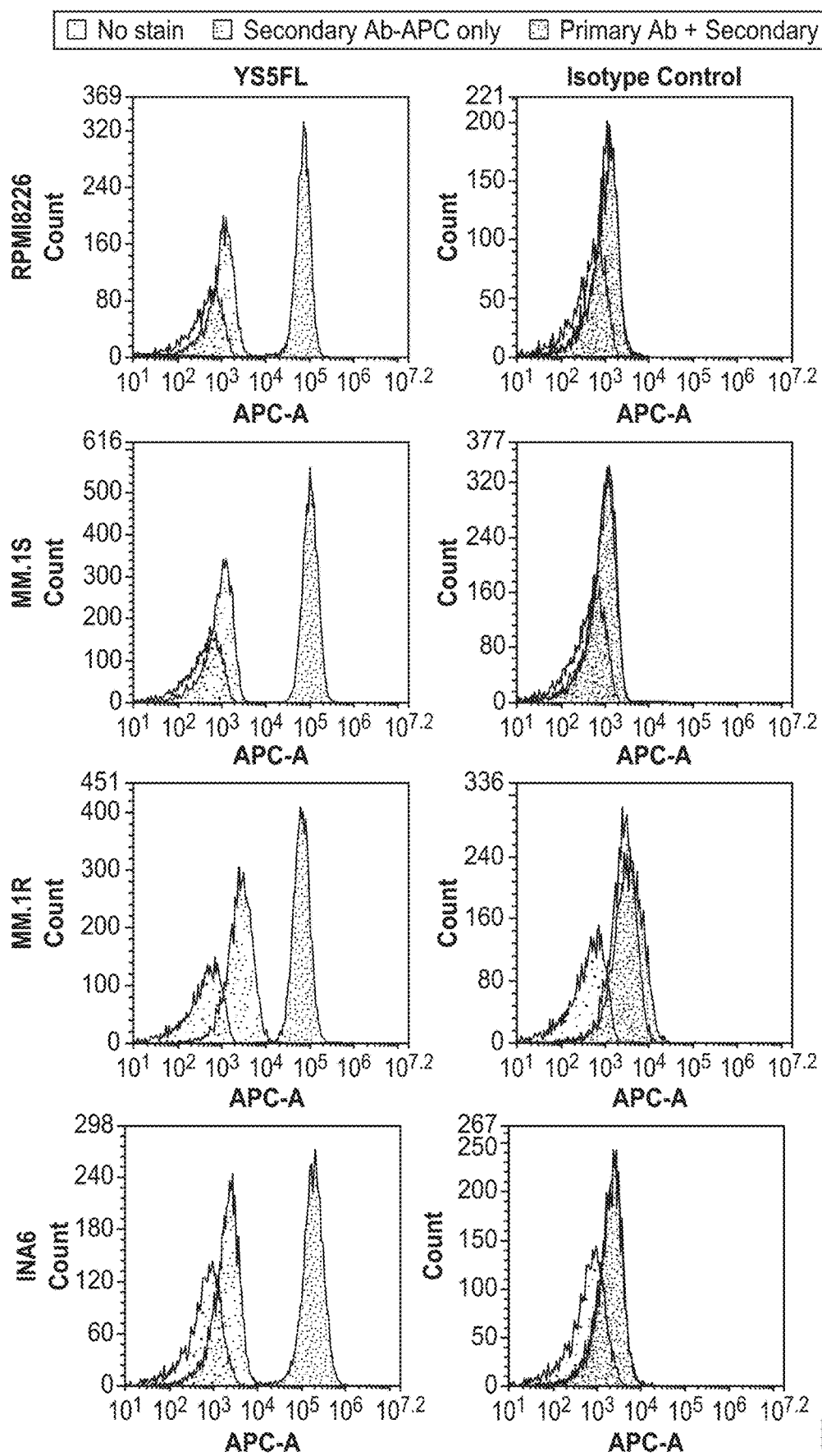
FIG. 2 depicts flow cytometry traces showing YS5FL binding to multiple myeloma cells.

Cell surface CD46 was detected by flow cytometry. Cells were harvested, centrifuged and resuspended in FACS buffer (PBS+2% FBS) at a concentration of 1×10⁶ cells/mL. 100 µL of cell suspension was dispensed into each well of a 96-well plate, 100 µL of YS5FL at 10 µg/mL was added to the wells and incubated for 1 hour at 4° C. The cells were washed three times with FACS buffer. After the third wash, the cells were resuspended in 100 µL 1:500 diluted AlexaFluor-488 mouse anti-Human IgG1 Fc secondary antibody and incubated for 1 hour at 4° C. in the dark. The cells were washed three times with 200 µL PBS by centrifuging at 2000 RPM for 5 minutes. After the last wash, the cells were resuspended in 300 µL cold PBS and analyzed on a FACSVersen™ (BD Biosciences) flow cytometer. YS5FL bound specifically to the surface of LnCap-C4-2B, LnCap-C4, DU145, PC3-luc, and Hs27 prostate cancer cells, but not to non-tumor BPH1 cells. FIG. 1. Likewise, YS5FL bound specifically to the surface of RPMI8226, MM.1S, MM.1R, and INA6 multiple myeloma cells. FIG. 2.

Example 2: Preparation of the FOR46 Immunoconjugate

Figure 3:
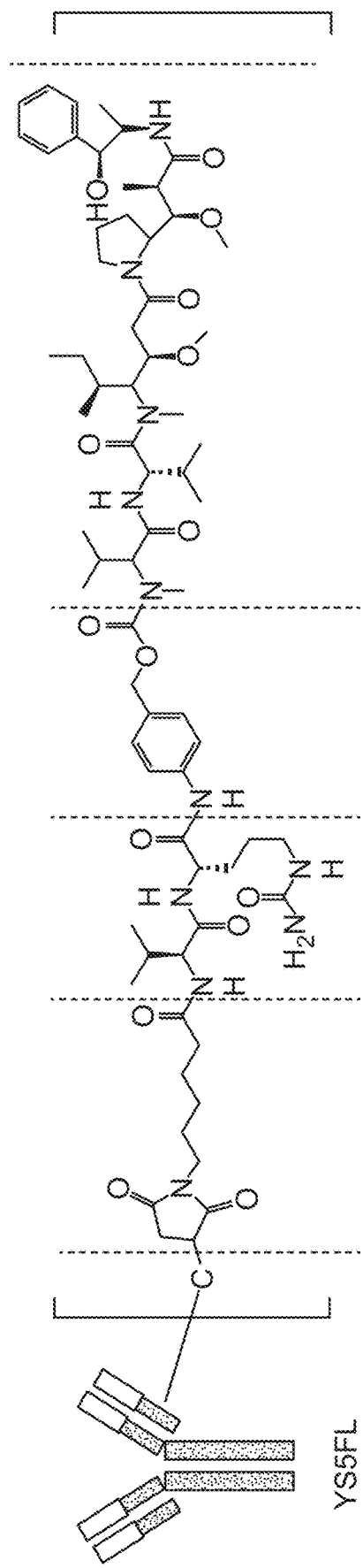
FIG. 3 is a diagram showing the structure of the FOR46 immunoconjugate described herein.
Figure 4:
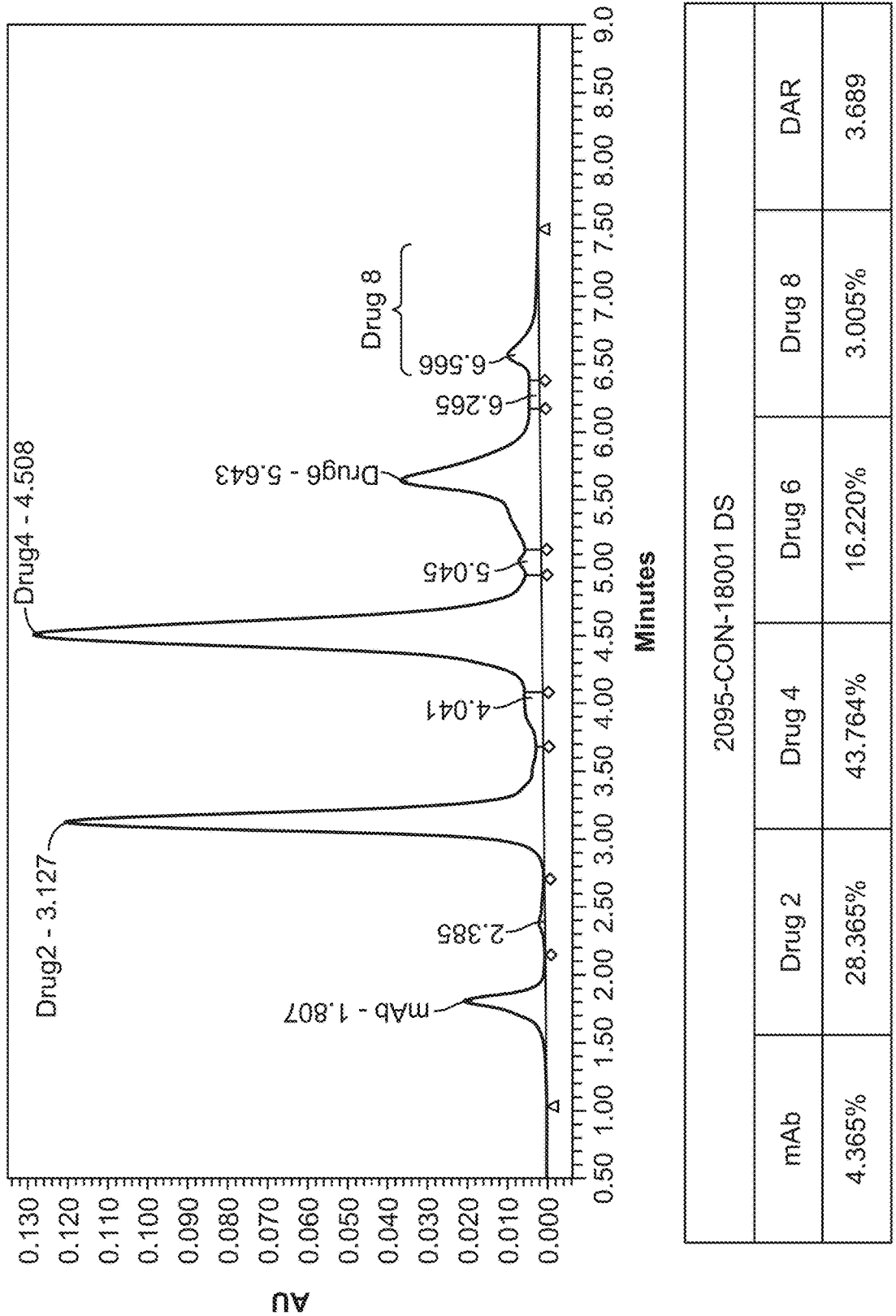
FIG. 4 is a hydrophobic interaction chromatography trace showing the stoichiometry of MMAE conjugation to YS5FL in FOR46.

The structure of YS5FL conjugated to an MMAE effector via a mc-vc-PAB linker is shown in FIG. 3. Purified YS5FL mAb (10 mg/ml) is adjusted to a pH of 6.8 with sodium phosphate buffer and then treated with TCEP (TCEP/mAb ratio of 2.1) for two hours at 22° C. Reduced mAb is reacted with mc-vc-PAB-MMAE (drug/mAb ratio of 6) in 9% dimethylacetamide for 15 min. The mAb is reduced a second time for one hour, conjugated a second time for 60 min, and the reaction is quenched by lowering the pH to 5.0 with 1M acetic acid, yielding a FOR46 immunoconjugate with a drug to antibody ratio of about 3.7, as determined by hydrophobic interaction chromatography. FIG. 4.

Example 3: FOR46 Drug Product

The FOR46 immunoconjugate was formulated into a drug product such that it could be administered to a human subject. The formulation contains 10.0±1.0 mg/mL FOR46 drug substance: 20 mM L-histidine buffer, 8.0% (w/v) sucrose, and 0.01% (w/v) polysorbate 80, pH 6.0. The formulation was determined to provide adequate stability (prevention of denaturation of the antibody and prevention of aggregation), buffering, and cryoprotection for storage at −20° C. After storage for 1 month at 5° C., the formulation retained >90% binding potency and cell based activity; was >90% monomeric; had residual MMAE of <15 µg/mL; and was essentially free of visible particles.

Example 4: Dose Escalation Study—Treatment of Metastatic Castration Resistant Prostate Cancer with FOR46

A dose escalation clinical trial is being carried out to determine the maximum tolerated dose (or maximum tested dose) of FOR46 in human subjects having metastatic castration resistant prostate cancer (mCRPC), including treatment associated small cell/neuroendocrine prostate cancer (tSCNC). Eligible patients had progressed on 1 or more androgen signaling inhibitor(s), exhibited maintained castrate testosterone levels (<50 ng/dL); and exhibited organ function defined by the following hemoglobin (Hgb)>8 g/dL, absolute neutrophil count (ANC)>1500/µL; platelets (Plts)>100 k; aspartate transaminase to alanine transaminase ratio (ALT/AST)<2.5×upper limit of normal (ULN); bilirubin (Bili)<1.5 mg/dL; and creatinine<1.5×ULN. No prior chemotherapy for mCRPC was allowed. Eligible patients received or are contemplated to receive FOR46 via IV infusion every 21 days. Thirty-three subjects were enrolled at 10 dose levels from 0.1 to 3.0 mg/kg. The median age was 66 (range 42-81); median baseline PSA was 41 (range 0.2-1627); and 7 subjects had visceral organ metastases. Patient demographics are presented in Table 7.

TABLE 7

Demographics of patients in the prostate cancer dose escalation trial.

| Characteristic (N = 33) | Current Data |
|---|---|
| Median age (range) | 67.5 (42-81) |
| Gender | 33 Males |
| Race - White/Asian/Other/Black/American Indian | 26/1/1/4/1 |
| Median number of prior regimens (range) | 3 (2-8) |
| Type of disease progression at study entry | |
| PSA | 13 |
| Nodal only (no bone disease) | 3 |
| Bone (± nodal disease) | 16 |
| Visceral (lung, liver, adrenal, CNS) disease ± other sites | 4 |
| Number of patients with visceral disease | 7 |

An accelerated titration followed by 3+3 dose escalation design was used. Following excess toxicity (neutropenia and fatigue) in subjects with high body mass index (BMI), dosing was changed from actual body weight to adjusted body weight. G-CSF secondary prophylaxis was specified for subjects experiencing grade≥3 neutropenia during a previous treatment cycle. In the absence of excess toxicity, treatment is continued if the investigator determines there is potential clinical benefit. A 50% decrease in serum prostate specific antigen (PSA) levels provides preliminary objective evidence of a response to treatment.

The 33 subjects were grouped into 10 cohorts receiving different doses. The cohorts and patient status are summarized in Table 8. Reductions in PSA and tumor burden are summarized in Table 9. At 1.2 mg/kg or higher (n=24), 9 subjects (38%) had a 50% reduction in PSA levels (PSA50 response), and 15 (63%) had any decline in PSA. Of 8 subjects with measurable disease, three objective partial responses (PR) were reported, and 6 had stable disease lasting from 9 to 39 weeks, as determined by RECIST criteria. Eisenhauer et al, New response evaluation criteria in solid tumours: Revised RECIST guideline (version 1.1), European Journal of Cancer 45 (2009) 228-249. The median number of treatment cycles is 6 (range 1-28) with 11 ongoing.

Figure 6:
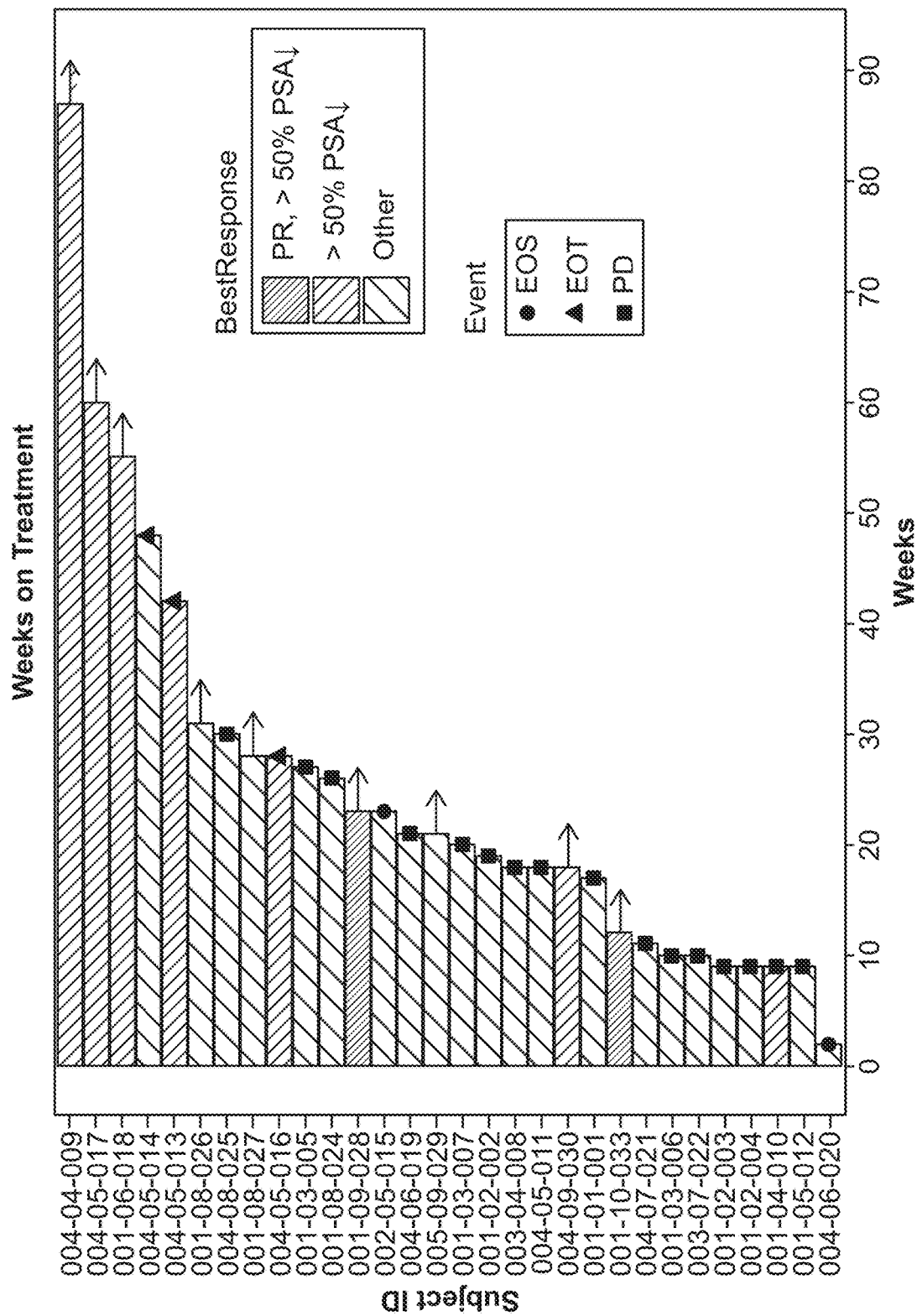
FIG. 6 is a swimmer plot showing the status of patients in the prostate cancer dose escalation trial. PR: partial response; EOS: end of study; EOT: end of treatment; PD: progressive disease.

PSA levels and RECIST results after each infusion cycle are presented for Cohorts 4-10 are presented in Tables 10-16, respectively. The results for all patients are summarized in FIG. 6.

Figure 5A:
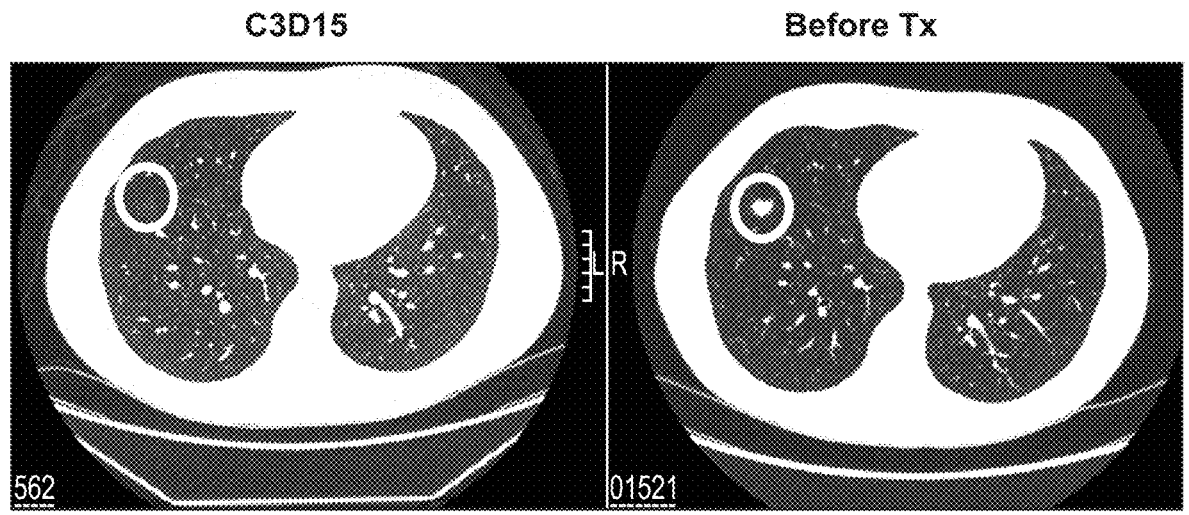
FIG. 5A is a CT scan showing metastatic lesions in castration resistant prostate cancer patient 001-09-28 (dosed at 2.7 mg/kg FOR46) at Cycle 3 Day 15 and before treatment.
Figure 5B:
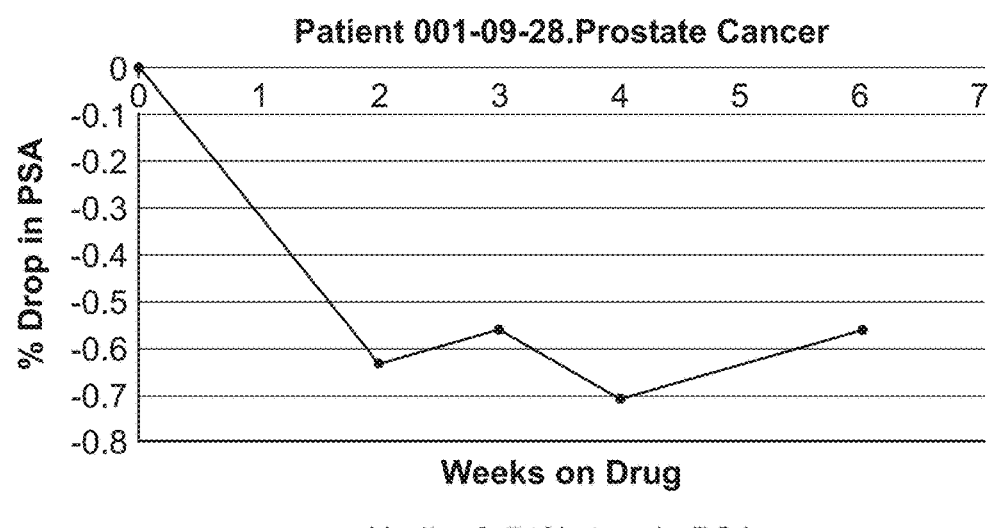
FIG. 5B is a graph illustrating a reduction in serum PSA in patient 001-09-28.

Patient 12 had the most substantial reduction in tumor burden. A CT scan after three cycles of treatment with 2.7 mg/kg revealed complete shrinkage of the largest tumor. FIG. 5A. The sum of the largest diameters of the target lesions (SLD, including lung nodules and a peri-rectal soft tissue mass) was reduced from 5.7 cm at baseline to 2.0 cm (a 65% reduction) after cycle 6. This was accompanied by a 71% reduction in serum PSA and a decrease in non-target lesions including RP nodes. FIG. 5B.

Neutropenia was analyzed by determining an absolute neutrophil count (ANC) as shown in Table 17. Grade 2 or higher neutropenia was observed in 12 of 16 patients treated with at least 1.8 mg/kg FOR46.

TABLE 8

Cohorts, Patient ID's and current status of subject in the prostate cancer dose escalation trial.

| | Patient ID | Status |
|---|---|---|
| Cohort 4 (1.2 mg/kg) | 003-04-008 | EOT due to disease progression (C9) after COVID-19 treatment pause |
| | 004-04-009* | Ongoing C26D1 |
| | 001-04-010 | EOT due to disease progression (C3) |
| Cohort 5 (1.8 mg/kg) | 004-05-011 | EOT due to disease progression (C13) |
| | 001-05-012 | EOT due to disease progression (C3) |
| | 004-05-013 | EOT due to increased neuropathy (C11) |
| | 004-05-014* | EOT due to disease progression (C15) |
| | 002-05-015 | EOT due to disease progression (C5) |
| | 004-05-016 | EOT due to disease progression (C9) |
| | 004-05-017 | EOT due to increased neuropathy (C10) |
| Cohort 6 (2.4 mg/kg) | 001-06-018 | Ongoing C17D1 |
| | 004-06-019 | EOT due to disease progression (C6) |
| | 004-06-020 | Pt deceased prior to C2D1 - Not evaluable for response |
| Cohort 7 (2.1 mg/kg) | 004-07-021 | EOT due to disease progression (C3) |
| | 003-07-022 | EOT due to disease progression (C3) |
| | 003-07-023 | EOT patient withdrawn (C1) - axillary adenopathy; RUE swelling |
| Cohort 8 (2.4 mg/kg w/AJBW) | 001-08-024 | EOT due to disease progression (C9) |
| | 004-08-025 | EOT due to disease progression (C10) |
| | 001-08-026 | Ongoing C10D1 - no dose reduction through C10 (165 mg) |
| | 001-08-027 | Ongoing C9D1 - no dose reduction through C9 (191 mg) |
| Cohort 9 (2.7 mg/kg) AJBW | 001-09-028 | Ongoing C7D1 - no dose reduction through C7 (183 mg) |
| | 005-09-029 | Ongoing C5D1 - dose reduced to 2.4 mg/kg at C2 and 1.8 mg/kg at C3 |
| | 004-09-030 | Ongoing C6D1 - no dose reduction through C6 (173.9 mg) |
| Cohort 10 (3.0 mg/kg) AJBW | 003-10-031 | C4D1 - C2 dose reduced to 2.4 mg/kg; C3 dose reduced to 2.1 mg/kg C4 delayed due to colitis and dose reduced to 1.8 mg/kg |
| | 004-10-032 | Death due to disease progression (C1) |
| | 001-10-033 | C3D1 - dose reduced to 2.7 mg/kg |
| Dose Expansion | 003-09-101 | C1D1 |

EOT: end of treatment; C: course; D: day; *dose increase to 2.1 mg/kg.

TABLE 9

Summary of responses to FOR46 in the prostate cancer dose escalation trial.

| Patient ID | Dose (mg/kg) | % PSA Change | PSA Change | RECIST | # Cycles |
|---|---|---|---|---|---|
| 003-04-008 | 1.2 | +37 | | | 9 |
| 004-04-009 | 1.2 | −94 | ≥50% | | 26+ |
| 001-04-010 | 1.2 | −51 | ≥50% | | 3 |
| 004-05-011 | 1.8 | +75 | | | 14 |
| 001-05-012 | 1.8 | +34 | | | 3 |
| 004-05-013 | 1.8 | −56 | ≥50% | | 13 |
| 004-05-014 | 1.8 | −31 | Red | | 14 |
| 002-05-015 | 1.8 | −14 | Red | | 2 |
| 004-05-016 | 1.8 | −50 | ≥50% | | 9 |
| 004-05-017 | 1.8 | −79 | ≥50% | | 9 |
| 001-06-018 | 2.4 | −51 | ≥50% | | 18+ |
| 004-06-019 | 2.4 | +76 | | | 6 |
| 004-07-021 | 2.1 | +55 | | | 3 |
| 003-07-022 | 2.1 | −34 | Red | | 5 |
| 001-08-024 | 2.4 AJBW | −12 | Red | | 9 |
| 004-08.025 | 2.4 AJBW | +27 | | | 10 |
| 001-08-026 | 2.4 AJBW | −3 | Red | | 4 |
| 001-08-027 | 2.4 AJBW | +20 | | | 9 |
| 001-09-028 | 2.7 AJBW | −71 | ≥50% | PR | 10+ |
| 004-09-030 | 2.7 AJBW | −79 | ≥50% | | 7+ |
| 003-10-031 | 3.0 AJBW | 34 | | PR | 4+ |
| 001-10-033 | 3.0 AJBW | −74 | ≥50% | PR | 4+ |

PR: partial response

TABLE 10

Serum PSA (mg/ml) levels and tumor dimensions (RECIST) in Cohort 4 metastatic castration resistant prostate cancer patients treated with 1.2 mg/kg FOR46.

| Patient ID | SCR | C1 | C2 | C3 | C4 | C7 | C10 | C14 | C18 | C22 | C26 |
|---|---|---|---|---|---|---|---|---|---|---|---|
| 003-04-008 | 399 | 352.9 | 419.3 | 414.2 | 484.0 | 507 | EOT | — | — | — | |
| RECIST | 98 mm | | | | SD | SD | PD | | | | |
| | | | | | −6.1% | −9.8% | | | | | |
| | | | | | 92 mm | 88 mm | | | | | |
| 004-04-009* | 78.7 | 9.4 | 2.4 | 0.58 | 0.66 | 1.17 | 4.13 | 10.4 | 14.2 | 17.37 | 19.33 |
| RECIST | NM | | | | N/N | NN | N/N | N/N | N/N | N/N | N/N |
| 001-04-010 | 1603 | 1626 | >149 | 794.6 | 1502 | — | — | — | — | | |
| RECIST | 18 mm | | | | PD | | | | | | |

SCR: screen;

C: course;

D: day;

N/N: Non-complete response, non-progressive disease;

SD: stable disease;

PD: progressive disease;

*dose increased to 2.1 mg/kg AJBW at C17.

TABLE 11

Serum PSA (mg/ml) levels and tumor dimensions (RECIST) in Cohort 5 metastatic castration resistant prostate cancer patients treated with 1.8 mg/kg FOR46.

| Patient ID | SCR | C1 | C2 | C3 | C4 | C5 | C6 | C7 | C8 | C9 | C10 |
|---|---|---|---|---|---|---|---|---|---|---|---|
| 004-05-011 | 45.6 | 55.0 | 78.8 | 95.0 | 96.1 | 98.9 | 126.7 | 146.4 | 163.5 | 171.5 | 221 |
| RECIST | 43 | | | | SD | | | SD | | | SD |
| | | | | | 47 | | | 51 | | | 52 |
| 001-05-012 | 382 | 545.5 | 623.6 | 731.8 | 1027 | — | — | — | — | — | — |
| RECIST | 134 | | | | PD | | | | | | |
| | | | | | 174 | | | | | | |
| 004-05-013 | 57.7 | 57.5 | 28.4 | 25.4 | 26.6 | 31.6 | 42.2 | 59.0 | 66.2 | 55.0 | 53.4 |
| RECIST | 63 | | | | SD | | | SD | | | SD |
| | | | | | −14.2% | | | −9.5% | | | −6.77% |
| | | | | | 54 | | | 57 | | | 59 |
| 004-05-014 | 129 | 152.7 | 198.4 | 141.1 | 150.1 | 109 | 106.2 | 111 | 113.9 | 104.9 | 127.7 |
| RECIST | 40 | | | | SD | | | SD | | | SD |
| | | | | | −7.5% | | | −17.5% | | | −14.2% |
| | | | | | 37 | | | 33 | | | 35 |
| 002-05-015 | 685 | 884 | 758 | 991 | 1179 | 1136 | 1147 | — | — | — | — |
| RECIST | NM | | | | N/N | | | | | | |
| 004-05-016 | 91.2 | 71.5 | 81.7 | 54.6 | 49.1 | 35.7 | 48 | 54.8 | 54.7 | 77.5 | 99.1 |
| RECIST | NM | | | | N/N | | | NN | | | PD new lesion |
| 004-05-017 | 1.49 | 1.44 | 0.8 | 0.66 | 1.0 | 0.4 | 0.3 | 0.3 | 0.4 | 0.73 | 1.8 |
| RECIST | NM | | | | N/N | | | NN | | | EOT |
| | | | | | | | | | | | N/N |

SCR: screen;
C: course;
D: day;
SD: stable disease;
PD: progressive disease;
*004-05-014 discontinued after cycle 15 due to peripheral neuropathy and fatigue/weakness;
AE: adverse event.

| Patient ID | C11 | C12 | C13 | C14 | C15 |
|---|---|---|---|---|---|
| 004-05-011 | 235 | 254 | 250.8 | 312.6 | — |
| RECIST | | | | 53 | |
| 001-05-012 | — | — | — | — | — |
| RECIST | | | | | |
| 004-05-013 | 60.6 | 48.27 | 53.79 | 64.27 | — |
| RECIST | | | | PD | |
| 004-05-014 | 135.5 | 173.3 | 212.5 | 256.9 | 297.3 |
| RECIST | | | | SD | Off due |
| | | | | −17.5% | to AE* |
| | | | | 33 | |

TABLE 11-continued

Serum PSA (mg/ml) levels and tumor dimensions (RECIST) in Cohort 5 metastatic castration resistant prostate cancer patients treated with 1.8 mg/kg FOR46.

002-05-015
RECIST
004-05-016
RECIST
004-05-017
RECIST

C: course;
D: day;
SD: stable disease;
PD: progressive disease;
*004-05-014 discontinued after cycle 15 due to peripheral neuropathy and fatigue/weakness;
AE: adverse event.

TABLE 12

Serum PSA (mg/ml) levels and tumor dimensions (RECIST) in Cohort 6 metastatic castration resistant prostate cancer patients treated with 2.4 mg/kg FOR46.

| Patient ID | SCR | C1 | C2 | C3 | C4 | C5 | C6 | C7 | C8 |
|---|---|---|---|---|---|---|---|---|---|
| 001-06-018* | 47.6 | 16.4 | 14.5 | 8.1 | 9.8 | 16.5 | 19.2 | 22.3 | 28.9 |
| RECIST | NM | | | | N/N | | | N/N | |
| 004-06-019* | 3.53 | 6.93 | 15.3 | 12.2 | 15.3 | 18.7 | 25.3 | 43.6 | — |
| RECIST | NM | | | | N/N | | | | |
| 004-06-020 | 7.5 | 5.6 | — | — | — | — | — | — | — |
| RECIST (mm) | 179 | NE | | | | | | | |

| Patient ID | C9 | C10 | C11 | C12 | C13 | C14 | C15 | C16 | C17 |
|---|---|---|---|---|---|---|---|---|---|
| 001-06-018* | 25.2 | 21.2 | 17.8 | 14.2 | 17.5 | 16.1 | 17.8 | 21.7 | 19.1 |
| RECIST | | N/N | | | | N/N | | | |
| 004-06-019* | — | — | — | — | — | — | — | | |
| RECIST | | | | | | | | | |
| 004-06-020 | — | — | — | — | — | — | — | | |
| RECIST (mm) | | | | | | | | | |

SCR: screen;
C: course;
D: day;
SD: stable disease;
N/N: Non-complete response, non-progressive disease;
NE: inevaluable.

TABLE 13

Serum PSA (mg/ml) levels and tumor dimensions (RECIST) in Cohort 7 metastatic castration resistant prostate cancer patients treated with 2.1 mg/kg FOR46.

| Patient ID | SCR | C1 | C2 | C3 | C4 | C5 |
|---|---|---|---|---|---|---|
| 004-07-021 | 3.88 | 4.2 | 5.5 | 6.5 | — | — |
| RECIST | 104 | | | | 113 | |
| 003-07-022 | 24.7 | 34.1 | 31.4 | 27.7 | 20.7 | 22.7 |
| RECIST (mm) | NM | | | | PD | |
| 003-07-023# | 119.5 | 138 | 487 | — | — | — |
| RECIST (mm) | | | NE | | | |

SCR: screen;
C: course;
PD: progressive disease;
NE: inevaluable;
* Dose reduced from C2 on to 1.8 mg/kg actual body weight;
Dosed according to AJBW.

TABLE 14

Serum PSA (mg/ml) levels and tumor dimensions (RECIST) in Cohort 8 metastatic castration resistant prostate cancer patients treated with 2.4 mg/kg (adjusted body weight) FOR46.

| Patient ID | SCR | C1 | C2 | C3 | C4 | C5 | C6 | C7 | C8 | C9 | C10 | C11 |
|---|---|---|---|---|---|---|---|---|---|---|---|---|
| 001-08-024 | 5.8 | 5.8 | 5.1 | 5.3 | 5.9 | 7.1 | 9.5 | 13.5 | 14.2 | 15.2 | 21.75 | |
| RECIST | 52 mm | | | | SD 50 mm | | | SD 55 mm | | | PD 67 mm | |

TABLE 14-continued

Serum PSA (mg/ml) levels and tumor dimensions (RECIST) in Cohort 8 metastatic castration resistant prostate cancer patients treated with 2.4 mg/kg (adjusted body weight) FOR46.

| Patient ID | SCR | C1 | C2 | C3 | C4 | C5 | C6 | C7 | C8 | C9 | C10 | C11 |
|---|---|---|---|---|---|---|---|---|---|---|---|---|
| 004-08-025 | 164 | 130 | 186 | 181 | 222 | 167 | 217 | 206 | 229.8 | 250.5 | 301 | 357 |
| RECIST | 61 mm | | | | SD 63 mm | | | SD | | | | EOT |
| 001-08-026 | 0.68 | 0.62 | 0.60 | 0.64 | 0.75 | 0.98 | 1.4 | 0.7 | 2.1 | 1.6 | 1.921 | |
| RECIST | NM | | | | N/N | | | N/N | | | N/N | |
| 001-08-027 | 82.6 | 79.5 | 97.8 | 95.4 | 117 | 135 | 160 | 153.8 | 170.7 | 190.8 | | |
| RECIST | NM | | | | N/N | | | N/N | | | | |

SCR: screen;
C: course;
NM: Not measurable;
SD: Stable disease;
N/N: Non-complete response, non-progressive disease.

TABLE 15

Serum PSA (mg/ml) levels and tumor dimensions (RECIST) in Cohort 9 metastatic castration resistant prostate cancer patients treated with 2.7 mg/kg (adjusted body weight) FOR46.

| Patient ID | SCR | C1 | C2 | C3 | C4 | C5 | C6 | C7 | C8 |
|---|---|---|---|---|---|---|---|---|---|
| 001-09-028 | 22.4 | 24.9 | 10.9 | 10.9 | 15.5 | 31.0 | 33.97 | 54.5 | |
| RECIST | 57 mm | | | | 25 mm PR | | | 20 mm PR | |
| 005-09-029 | 0.2 | 0.20 | 0.21 | 0.20 | 0.20 | | | | |
| RECIST | NM | | | | N/N | | | | |
| 004-09-030 | 134 | 162 | 96 | 52 | 34.2 | 34.7 | 30.81 | | |
| RECIST | NM | | | | N/N | | | | |

SCR: screen;
C: course;
PR: partial response;
NM: Not measurable;
N/N: Non-complete response, non-progressive disease.

TABLE 16

Serum PSA (mg/ml) levels and tumor dimensions (RECIST) in Cohort 10 metastatic castration resistant prostate cancer patients treated with 3.0 mg/kg (adjusted body weight) FOR46.

| Patient ID | SCR | C1 | C2 | C3 | C4 |
|---|---|---|---|---|---|
| 003-10-031* | 5.80 | 2.58 | 1.7 | 1.78 | 2.09 |
| RECIST | 24 mm | | | | 13 mm |
| 004-10-032 | 51.32 | 65.99 | D/C | | |
| RECIST | | | Hospice | | |
| 001-10-033# | 188.9 | 221.6 | 65.4 | 57.3 | 50.8 |
| RECIST | 16 cm | | | | 8.5 cm PR |

SCR: screen; C: course; PR: partial response; D/C: discontinued care;
*C2 dose reduced to 2.4 mg/kg (adjusted body weight);
C2 dose reduced to 2.7 mg/kg (adjusted body weight).

TABLE 17

Absolute neutrophil counts (×10$^9$/L) in metastatic castration resistant prostate cancer patients treated with FOR46.

| Patient ID | SCR | Wt | AJBW | Ht | BMI | Dose | C1D1 | C1D8 or 9 | C1D15 | C2D1 | C2D8 | C2D15 |
|---|---|---|---|---|---|---|---|---|---|---|---|---|
| 001-06-018 | 6.54 | 114.7 | | 185 | 33.5 | 275 | 2.83 | ˜˜˜˜0.19 | ˆ1.04 | 5.63 | 3.46 | ˜˜1.17 |
| 004-06-019 | 2.34 | 126.8 | | 182.9 | 37.9 | 304.3 | 2.47 | ˜˜˜˜0.1* | — | 2.37 | 4.6 | 4.1 |
| 004-06-020 | 7.00 | 123.6 | | 177.8 | 39.1 | 296.6 | 4.86 | ˜˜˜˜0.21* | — | — | — | — |
| 004-07-021 | 4.09 | 76.6 | | 179.1 | 23.9 | 160.9 | 3.52 | 2.72 | 2.98 | 4.8 | 1.63 | ˜˜1.47 |
| 003-07-022 | 6.2 | 68 | | 166 | 24.7 | 141.5 | 4.6 | 2.3 | ˜˜˜0.7 | 6.4 | 13.7 | 7.0 |
| 003-07-023 | 8.0 | 112.4 | | 180.3 | 34.6 | 189.2** | 7.8 | 3.1 | 2.2 | — | — | — |
| 001-08-024 | 2.96 | 112.6 | | 176.5 | 36.1 | 213*** | 2.60 | 2.47 | 3.31 | 1.98 | 2.61 | 1.93 |
| 004-08-025 | 4.43 | 71.7 | | 169 | 25.1 | 172.6** | 4.70 | ˆ1.42 | ˜˜˜0.31 | 4.37 | 8.18 | 7.40 |
| 001-08-026 | 4.12 | 73.9 | | 169.5 | 25.7 | 165** | 2.28 | ˆ1.11 | ˜˜1.31 | 3.81 | ˜˜1.16 | ˜˜˜˜0.76 |
| 001-08-027 | 4.67 | 94.5 | | 172.7 | 31.9 | 191** | 3.60 | 2.39 | 3.45 | 4.88 | 3.40 | 3.95 |
| 001-09-028 | 2.53 | 75 | 68 | 167 | 26.9 | 183 | 2.50 | ˜˜˜0.65 | ˜˜˜0.70 | 2.80 | 5.50 | 4.29 |

TABLE 17-continued

Absolute neutrophil counts (×10⁹/L) in metastatic castration resistant prostate cancer patients treated with FOR46.

| Patient ID | SCR | Wt | AJBW | Ht | BMI | Dose | C1D1 | C1D8 or 9 | C1D15 | C2D1 | C2D8 | C2D15 |
|---|---|---|---|---|---|---|---|---|---|---|---|---|
| 005-09-029 | 10.68 | 90.9 | 80 | 178 | 28.7 | 217.1 | 4.98 | ~~~~0.39 | 3.23 | 10.90 | 1.95 | ~~~0.8 |
| 004-09-030 | 4.02 | 64.1 | — | 172.7 | 21.5 | 173.9 | 5.10 | 1.89 | ~~1.38 | 2.90 | ~~1.33 | ~~~~0.09 |
| 003-10-031 | 2.4 | 80.8 | 73 | 172.7 | 27.1 | 220.2 | 2.2 | ~~~~0.1 | 0.4 | 1.8 | 5.4 | 6.6 |
| 004-10-032 | 4.8 | 95.6 | 87 | 186.5 | 27.5 | 261 | 4.14 | ~~~0.23 0.1 (Day 11) | D/C Hospice | | | |
| 001-10-033 | 2.16 | 85.2 | | 191.2 | 23.3 | 255 | 3.53 | 2.02 .895 (Day 6) | 1.45 | 1.30 | 2.70 | 3.15 |
| 003-09-101 | 2.6 | 83 | | 164.5 | 30.7 | 186.6 | 3.1 | | | | | |

Neutropenia (~grade 2; ~~~grade 3; ~~~~grade 4);
*G-CSF;
**adjusted body weight;
***adjusted body weight-did not receive full dose due to infusion reaction;
D/C: discontinued care.

Dose limiting toxicities were grade 4 neutropenia in 3 of 3 high body mass index (BMI) subjects at 2.4 mg/kg dosed by actual body weight and 2 of 3 subjects at 3.0 mg/kg dosed by adjusted body weight. The maximum tolerated dose (MTD) was 2.7 mg/kg by adjusted body weight (AJBW). The most common related adverse events were grade 4 neutropenia in 11 of 33 subjects (33%), grade 3 neutropenia in 6 (18%), and infusion related reactions (IRR) in 14 (42%), with 1 grade 3 IRR. Any grade neuropathy occurred in 7 subjects (21%), with grade 3 neuropathy in 1 (3%). The most frequent adverse events are shown in Table 18.

TABLE 18

Adverse event observed in at least two prostate cancer subjects treated with FOR46.

| | Number of Patients n (%) n = 35 Worst Grade by Patient | | |
|---|---|---|---|
| Adverse Event | Any Grade | 3 | 4 |
| Infusion related reaction | 14 (40) | 1 (3) | — |
| Neutropenia | 12 (34) | 3 (9) | 5 (14) |
| Neutrophil count decreased | 10 (29) | 3 (9) | 6 (17) |
| White blood cell count decreased | 8 (23) | 3 (9) | 1 (3) |
| Fatigue | 7 (20) | 1 (3) | — |
| Neuropathy peripheral | 7 (20) | 1 (3) | — |
| Diarrhea | 6 (17) | 1 (3) | — |
| Anemia | 5 (14) | 1 (3) | — |
| Lymphocyte count decreased | 5 (14) | 1 (3) | 1 (3) |
| Nausea | 5 (14) | — | — |
| Alopecia | 5 (14) | — | — |
| Hypokalemia | 4 (11) | — | — |
| ALT increased | 3 (9) | — | — |
| Constipation | 3 (9) | — | — |
| Decreased appetite | 3 (9) | — | — |
| Hypomagnesaemia | 3 (9) | — | — |
| Leukopenia | 2 (6) | — | 1 (3) |
| Lymphopenia | 2 (6) | — | — |
| AST increased | 2 (6) | — | — |
| Hepatic enzyme increased | 2 (6) | — | — |
| Chills | 2 (6) | — | — |
| Pyrexia | 2 (6) | — | — |
| Headache | 2 (6) | — | — |
| Hyponatremia | 2 (6) | 1 (3) | — |
| Hypophosphatemia | 2 (6) | — | — |
| Dyspnea | 2 (6) | — | — |

A dose expansion study has been initiated for subjects with prostate adenocarcinoma. CD46 expression is determined at enrollment by immunofluorescence microscopy. Three patients with moderate or strongly positive CD46 expression have been enrolled. A fourth subject negative for CD46 expression was not enrolled.

This example demonstrates that FOR46 has an acceptable toxicity profile using adjusted body weight dosing, and provides encouraging preliminary evidence of efficacy in androgen signaling inhibitor-resistant mCRPC subjects. FOR46 is currently being evaluated in two mCRPC expansion cohorts: adenocarcinoma and t-SCNC.

Example 5: Dose Escalation Study—Treatment of Relapsed or Refractory Multiple Myeloma with FOR46

A dose escalation clinical trial is in progress to treat human subjects having relapsed or refractory multiple myeloma with the FOR46 drug product described in Example 2. To be eligible a patient's prior therapy must have included a proteasome inhibitor, an immunomodulatory imide drug (ImiD) and a CD38-directed therapy. Eligible patients also have the following organ function indicators: Hemoglobin≥8 g/dL, ANC≥1500/µL; Platelets≥100 k; ALT/AST≤2.5×upper limit of normal (ULN); Bilirubin≤1.5 mg/dL; and Creatinine≤1.5×ULN. FOR46 was administered once every three weeks with infusion-related reaction prophylaxis by IV infusion over 30-60 minutes.

The initial protocol had 2.4 mg/kg actual weight as the highest dose. When the MTD was not defined using adjusted body weight dosing, escalation was held pending protocol amendment to allow a higher dose.

A dose expansion clinical trial with 10 patients dosed with FOR46 at 2.4 mg/kg adjusted body weight is also in progress. The eligibility criteria for the dose expansion trial were the same as for the dose escalation trial except ANC≥1000/µL and Platelets≥75 k.

For the dose escalation trial, fifteen subjects were enrolled at 6 pre-defined dose levels from 0.1 to 2.4 mg/kg with 1 patient each at the 0.1, 0.3 and 0.6 mg/kg dose levels, 3 at 1.2 and 1.8 mg/kg and 6 at 2.4 mg/kg. The median age was 68 (range 33-79) with 4 females. Gain 1 q was present in 9 pts, absent in 5 pts and unknown in 1. The median number of prior lines of therapy was 6 (range 3-17). Dosing for the dose escalation and dose expansion trials is shown in Table 19. Patient characteristics are shown in Tables 20 and 21.

TABLE 19

Dosing for the dose escalation and dose expansion trials of FOR46 for relapsing or refractory multiple myeloma

| Dose Level (mg/kg q 3 weeks) | N (25) |
|---|---|
| 0.1 | 1 |
| 0.3 | 1 |

TABLE 19-continued

Dosing for the dose escalation and dose expansion trials of FOR46 for relapsing or refractory multiple myeloma

| Dose Level (mg/kg q 3 weeks) | N (25) |
|---|---|
| 0.6 | 1 |
| 1.2 | 3 |
| 1.8 | 3 |
| 2.4 (Escalation - Actual/AJBW Dosing) | 6 (3/3) |
| 2.4 (Expansion - AJBW) | 10 |

TABLE 20

Demographics of subjects in dose escalation and dose expansion trials of FOR46 for relapsing or refractory multiple myeloma

| Characteristic | Escalation (n = 15) and Expansion (n = 10) |
|---|---|
| Median age (range) | 67 (33-79) |
| Gender F/M | 7/18 |
| Race - White/Black/Hispanic/Unknown | 19/2/1/2 |
| Myeloma Light Chain | |
| Kappa LC | 18 (2 light chain only) |
| Lambda LC | 6 |
| Immunoglobulin | |
| IgA | 6 |
| IgG | 15 |
| IgM | 1 |

TABLE 21

Prior therapies for subjects in dose escalation and dose expansion trials of FOR46 for relapsing or refractory multiple myeloma

| Prior Therapies, n (%) | Escalation (n = 15) and Expansion (n = 10) |
|---|---|
| Median (range) | 8 (3-19) |
| Received ≥ 5 lines of therapy | 21 (84) |
| Proteasome Inhibitor, received/refractory | 25 (100)/21 (84) |
| IMiD, received/refractory | 25 (100)/22 (88) |
| Pomalidomide, received/refractory | 20 (80)/18 (72) |
| Anti-CD38 therapy, received/refractory | 25 (100)/23 (92) |
| Carfilzomib, received/refractory | 23 (92)/23 (92) |

An accelerated titration followed by 3+3 dose escalation design is underway in the dose escalation trial. FOR46, at protocol specified doses, was infused intravenously over 30-60 minutes on Day 1 of 21-day cycles. Following excess toxicity (neutropenia and fatigue) in a subject with a high body mass index (BMT), dosing was changed from actual weight (AW) to adjusted body weight (AJBW). G-CSF secondary prophylaxis was administered to subjects experiencing grade≥3 neutropenia during a previous treatment cycle.

Safety was evaluated using Common Terminology Criteria for Adverse Events (CTCAE) v5.0. Dexamethasone was only allowed for infusion reaction prophylaxis. CD46 antigen density was determined on patient MM cells via flow cytometry. Treatment efficacy was monitored by measuring immunoglobulin levels (M-proteins) in serum or urine, including IgA, lambda light chain (h), kappa light chain (κ), and M-spike proteins.

The only dose-limiting toxicity was grade 4 neutropenia in 1 high BMI patient dosed by AW. This was the only dose-limiting toxicity among 6 pts at 2.4 mg/kg dosed by a mix of AW (n=3) and ABW (n=3). One of 3 at 2.4 mg/kg AJBW had non-dose limiting grade 4 neutropenia. The most common related adverse event was grade 4 neutropenia in 3 patients (20%). One patient (6.7%) had grade 4 thrombocytopenia and 1 each (6.7%) had grade 3 AST elevation, neutropenia, anemia, nausea, and peripheral neuropathy (PN). Adverse events are shown in Table 22.

TABLE 22

Adverse Events in for subjects in dose escalation and dose expansion trials of FOR46 for relapsing or refractory multiple myeloma

| | Number of Patients n (%) n = 25 | | |
|---|---|---|---|
| Adverse Reaction | Any Grade | Grade 3 | Grade 4 |
| Neutropenia | 6 (24) | 2 (8%) | 1 (4%) |
| Anemia | 5 (20) | 4 (16%) | — |
| AST increased | 4 (16) | 2 (8%) | — |
| Neutrophil count decreased | 4 (16) | 2 (8%) | 2 (8%) |
| Platelet count decreased | 3 (12) | 1 (4%) | 1 (4%) |
| Weight decreased | 3 (12) | — | — |
| Constipation | 3 (12) | — | — |
| Nausea | 3 (12) | 1 (4%) | — |
| Fatigue | 3 (12) | — | — |
| White blood cell count decreased | 2 (8) | 2 (8%) | — |
| Diarrhea | 2 (8) | — | — |
| Vomiting | 2 (8) | — | — |
| Pyrexia | 2 (8) | — | — |
| Arthralgia | 2 (8) | — | — |
| Headache | 2 (8) | — | — |
| Peripheral neuropathy | 2 (8) | — | — |
| Alopecia | 2 (8) | — | — |

In a preliminary evaluation, all patients administered FOR46 at a dose of less than 1.8 mg/kg (i.e. 0.1 mg/kg, 0.3 mg/kg, 0.6 mg/kg, and 1.2 mg/kg) had treatment ended due to disease progression. Treatment had been initiated for patients in the 1.8 mg/kg group. Patient 8 demonstrated a response to FOR46 treatment with a reduction in serum IgG, serum κ light chain, serum λ light chain, and urinary M-spike protein. This response provided preliminary evidence of anti-tumor activity at 1.8 mg/kg dose.

Four patients responded to FOR46 with a partial remission (PR) per IMWG criteria. BGM Durne et al. International uniform response criteria for multiple myeloma. Leukemia (2006) 1-7. See Table 23.

TABLE 23

Multiple myeloma patients responding to FOR46

| Patient ID Myeloma Type Dose Level | 1 q gain | C1D1/ # Cycles | Ig | Serum FLC (mg/dL) | Serum M-spike (g/dL) | Urine M-spike (g/24 hrs) | Best IMWG Response |
|---|---|---|---|---|---|---|---|
| 006-05-008 IgG Kappa 1.8 mg/kg | Neg | Feb, 5 2020 7 cycles | 4002 1193 | 573 12.4 | 2.84 0.44 | 20.35 IFE+; no M-spike | PR |

TABLE 23-continued

Multiple myeloma patients responding to FOR46

| Patient ID Myeloma Type Dose Level | 1 q gain | C1D1/ # Cycles | Ig | Serum FLC (mg/dL) | Serum M-spike (g/dL) | Urine M-spike (g/24 hrs) | Best IMWG Response |
|---|---|---|---|---|---|---|---|
| 001-06-012 IgA Kappa 2.4 mg/kg ABW | Pos | Jun. 29, 2020 12 | 1440 353 | 21.2 10.7 | 1.4 0.3 | — — | PR |
| 003-06-014 IgA Kappa | Pos | Oct. 21, 2020 9 | 187 (wnl) 168 | 68.1 34.8 | det det | 540 95 | PR |
| 001-06-102 IgG Lambda | Pos | Feb. 3, 2021 7 | 3520 2300 | 131.6 56.7 | 2.5 1.1 | — — | PR |

Of the 6 response-evaluable patients in the 1.8 and 2.4 mg/kg dose escalation cohorts, 3 had partial responses (PRs) lasting 21, 30, and 15 weeks, respectively. Of the PRs, one patient did not have gain of 1 q21. In dose expansion, 3 of 10 patients were not evaluable. Of the seven evaluable patients, one had a PR lasting 18 weeks and was discontinued while in partial response due to an adverse event of peripheral neuropathy. Two patients have ongoing stable disease through 3 and 6 cycles. Four patients had a best response of progressive disease.

Figure 7A:
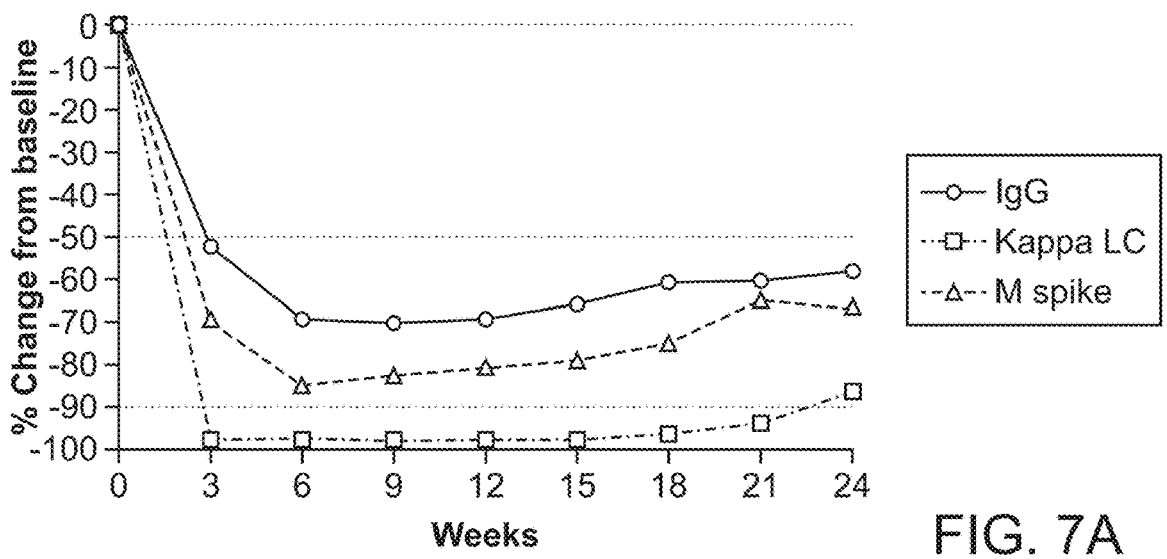
FIG. 7A is graph showing the response of multiple myeloma patient 006-05-008 to treatment with 1.8 mg/kg FOR46.

Patient 006-05-008 was treated with 1.8 mg/kg FOR46. This patient is a 62-year-old white male, diagnosed with IgG Kappa MM in July 2009. The patient is 1q gain negative and was previously treated with (1) daratumumab, pomalidomide, and dexamethasone; (2) pomalidomide and dexamethasone; (3) lenalidomide; (4) lenalidomide and bortezomib; and (5) Carfilzomib and pomalidomide. IgG, κ light chain, and Serum M-spike results are shown in FIG. 7A.

Figure 7B:
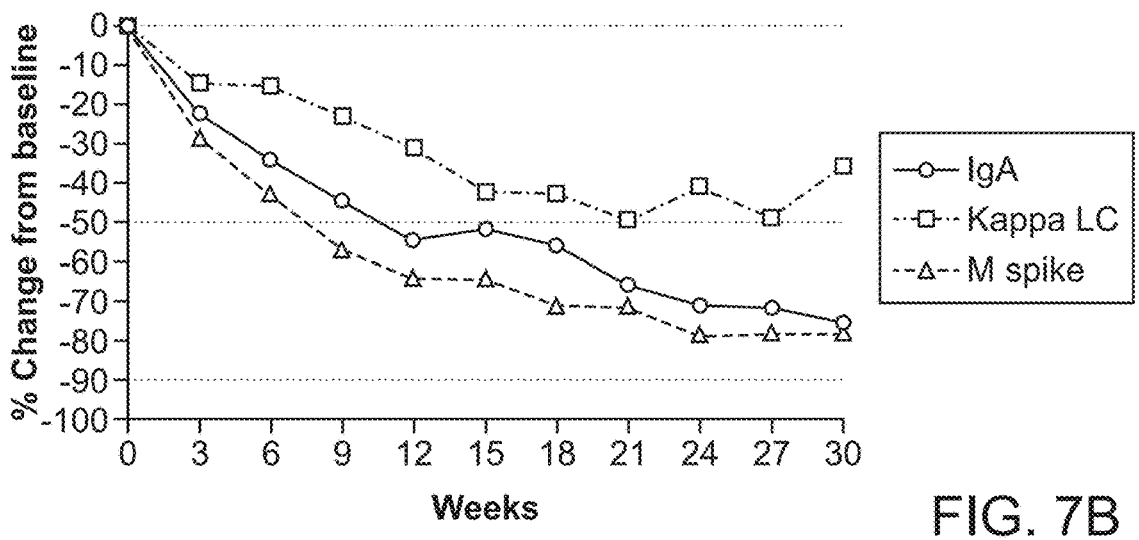
FIG. 7B is graph showing the response of multiple myeloma patient 001-06-012 to treatment with 2.4 mg/kg FOR46.

Patient 001-06-012 was treated with 2.4 mg/kg FOR46. This patient is a 70-year-old white male who diagnosed with IgA Kappa MM in January 2013; The patient is 1q gain positive and was previously treated with (1) cyclophosphamide, bortezomib, and dexamethasone; (2) lenalidomide, bortezomib, and dexamethasone; (3) carfilzomib, cyclophosphamide, and dexamethasone; and (4) daratumumab, pomalidomide, and dexamethasone. IgA, κ light chain, and Serum M-spike results are shown in FIG. 7B.

Figure 7C:
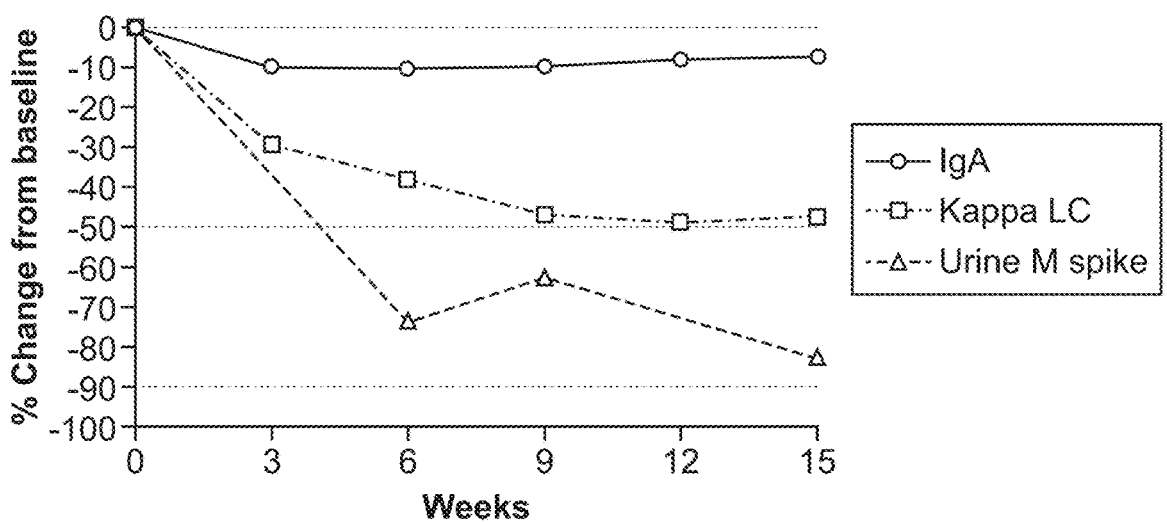
FIG. 7C is graph showing the response of multiple myeloma patient 003-06-014 to treatment with 2.4 mg/kg FOR46.

Patient 003-06-014 was treated with 2.4 mg/kg (AJBW) FOR46. This patient is a 56-year-old male who was diagnosed with IgA Kappa myeloma in December 2015. The patient is 1q21 gain positive and was previously treated with (1) cyclophosphamide, bortezomib, and dexamethasone; (2) carfilzomib, lenalidomide, dexamethasone, melphalan, and ASCT, with ixazomib maintenance; (3) carfilzomib, daratumumab, and dexamethasone; and (4) CAR-T clinical trial. IgA, κ light chain, and Urine M-spike results are shown in FIG. 7C.

Figure 8:
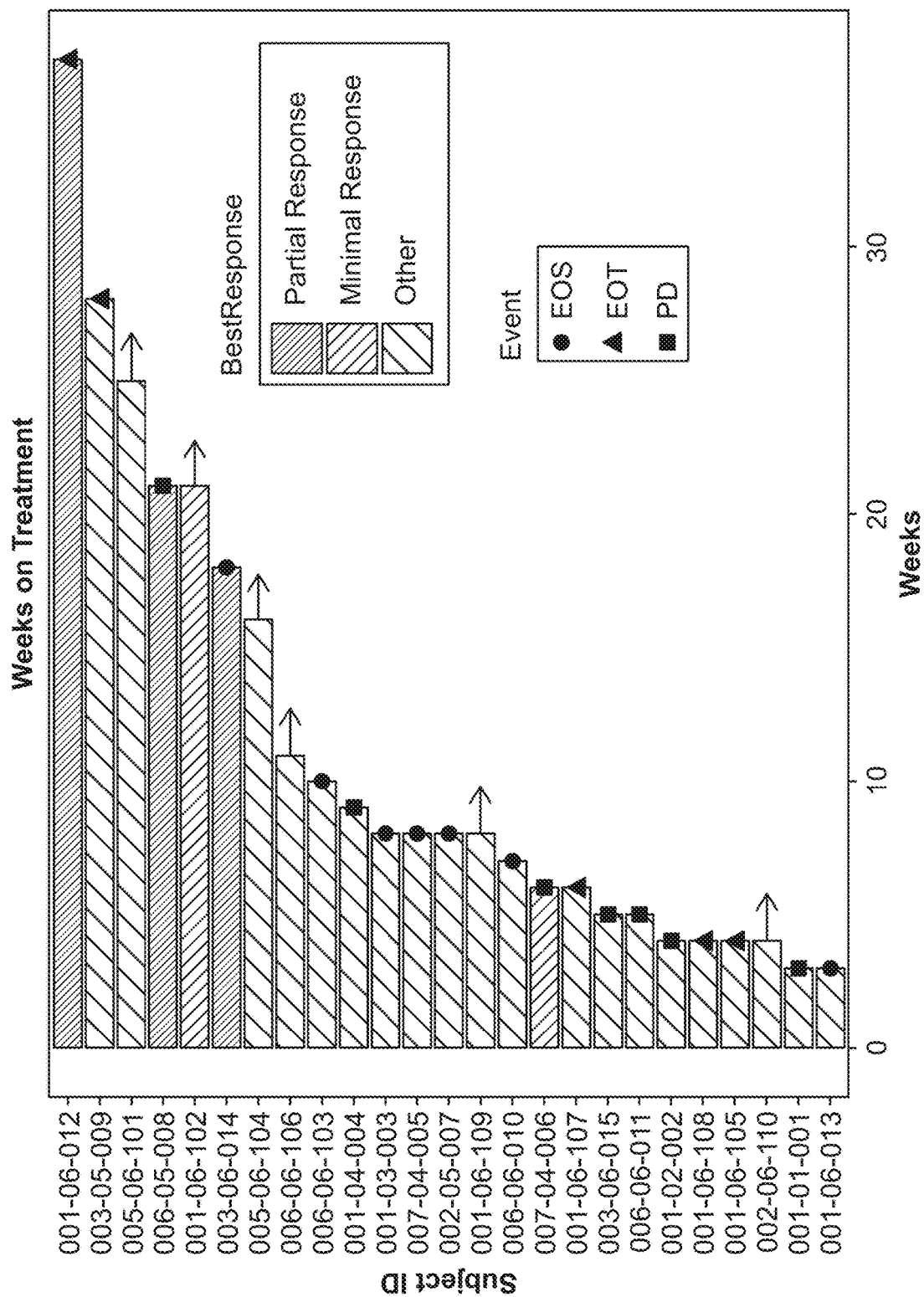
FIG. 8 is a swimmer plot showing the status of patients in the multiple myeloma dose escalation and extension trials. EOS: end of study; EOT: end of treatment; PD: progressive disease.

Results for all patients in the dose escalation trial are presented in Table 24. Results for all patients in the dose expansion trial are presented in Table 25. The results from both trials are summarized in FIG. 8.

In summary, FOR46 demonstrates an acceptable toxicity profile using adjustable body weight dosing. There is encouraging evidence of efficacy in triple refractory multiple myeloma. The dose escalation trial is being extended to 2.7 mg/kg by adjusted body weight.

TABLE 24

Biomarker results for refractory multiple myeloma patients treated with FOR46 in the dose escalation trial.

| Patient (Dose) | Analyte | Reference Range | Screen | C1 D1 | C2 D1 | C3 D1 | C4 D1 | C5 D1 | C6 D1 | C7 D1 | C8 D1 | C9 D1 | C10 | C11 | C12 | EOT or Status |
|---|---|---|---|---|---|---|---|---|---|---|---|---|---|---|---|---|
| 1 (0.1) | IgA | 672-1760 mg/dL | | 2230 | | | | | | | | | | | | EOT 3750 |
| | K | 5.7-26.3 mg/L | 1718.9 | 1772.4 | | | | | | | | | | | | EOT 3330.2 |
| | M-spike | Not detected | 1.5 | 2.1 | | | | | | | | | | | | 2.5 |
| 2 (0.3) | K | 3.3-19.4 mg/L | 179.9 | 201.4 | | | | | | | | | | | | EOT 648.7 |
| | M-spike | Not detected | 0 | | | | | | | | | | | | | |
| 3 (0.6) | IgG | 672-1760 mg/dL | 3570 | 3560 | 3710 | | | | | | | | | | | EOT 3560 |
| | K | 3.3-19.4 mg/L | 9.3 | 11.3 | 9.5 | | | | | | | | | | | EOT 12.6 |
| | M-spike | Not detected | 2.8 | | 2.7 | | | | | | | | | | | EOT 2.8 |
| 4 (1.2) | IgG | 672-1760 mg/dL | 1160 | 1230 | 1250 | 1380 | 1570 | 1690 | | | | | | | | EOT 1980 |
| | K | 3.3-19.4 mg/L | 107.9 | 137.3 | 185.8 | 203.8 | 293.5 | 318.3 | | | | | | | | EOT 452.4 |
| | M-Spike | 0 g/dL | 0.9 | 1.0 | 1.2 | 1.2 | 1.4 | 1.5 | | | | | | | | |

TABLE 24-continued

Biomarker results for refractory multiple myeloma patients treated with FOR46 in the dose escalation trial.

| Patient (Dose) | Analyte | Reference Range | Screen | C1 D1 | C2 D1 | C3 D1 | C4 D1 | C5 D1 | C6 D1 | C7 D1 | C8 D1 | C9 D1 | C10 | C11 | C12 | EOT or Status |
|---|---|---|---|---|---|---|---|---|---|---|---|---|---|---|---|---|
| 5 (1.2) | IgG | 700-1600 mg/dL | 1551 | 1539 | 1762 | — | — | — | | | | | | | | EOT 2012 |
| | λ | 5.7-26.3 mg/L | 281.8 | 331.7 | 415.1 | — | — | — | | | | | | | | 427.7 |
| | M-Spike | 0 g/dL | | 1.11 | 1.07 | 1.25 | — | — | — | | | | | | | EOT 1.43 |
| 6 (1.2) | K | 3.3-19.4 mg/L | 3780.3 | 7915.0 | 3874.6 C2D8 | 8919.2 | | | | | | | | | | EOT 14833.4 |
| | M-spike | 0 gm/dL | | 0.24 | 0.45 | 0.47 | 0.69 | | | | | | | | | EOT 0.86 |
| | M-spike (urine) | 0 gm/dL | | 268.1 | | | | | | | | | | | | |
| 7 (1.8) 1q21 pos | IgG | 635-1741 | | 2910 | 2990 | 3288 | 3596 | | | | | | | | | |
| | K | 0.33-19.4 mg/dL | | 258.00 | 290.0 | 398.0 | EOT 1183 | | | | | | | | | EOT 1183 |
| | M-Spike | Not detected g/dL | | 2.30 | 2.27 | 2.35 | | | | | | | | | | |
| 8 (1.8) 1q21 neg | IgG | 610-1616 mg/dL | | 3049 | 4002 | 1899 | 1233 | 1193 | 1231 | 1373 | 1573 | 1594 | 1681 | | | |
| | K | 0.33-19.4 mg/dL | | 296.2 | 573.0 | 14.1 | 16.3 | 12.4 | 12.9 | 14.2 | 21.1 | 36.6 | 79.2 | | | |
| | M-Spike | Not detected g/dL | | 1.86 | 2.84 | 0.87 | 0.44 | 0.50 | 0.56 | 0.60 | 0.72 | 1.01 | 0.96 | | | |
| | M-Spike (urine, 24 hour) | Not detected g/dL | | 1.1 | | IFE+; No M-spike | | | | | | | | | | |
| | IMWG Response | | | | | | | PR | | PR | | PD EOT | | | | |
| 9 (1.8) 1q21 neg | IgA | 66-433 mg/dL | | 945 | 1309 | 1328 | 1285 | 1450 | 1436 | 1566 | 1510 | 1556 | | | | |
| | K | 0.33-1.94 mg/L | | 3.33 | 3.93 | 4.66 | 5.11 | 5.17 | 5.62 | 6.50 | 7.67 | 8.65 | | | | |
| | M-spike | 0 g/dL | | Det | | Det | Det | Det | Det | Det | Det | Det | | | | |
| | M-Spike (urine, 24 hour) | | | | | | N/D | Det | Det | N/D | | | | | | |
| | IMWG Response | | | | | | | SD | | SD | | | | | | |
| 10 (2.4) 1q21 neg | K | | | 1037.5 | 1074 | 1485 | | | | | | | | | | |
| | M-spike | 0 g/dL | | | 0.06 | 0 | | | | | | | | | | |
| | IMWG Response | | | | | | | | | | | | | | | |
| 11 (2.4) 1q21 pos | IgG | 610-1616 mg/dL | | 1466 | 1585 | | | | | | | | | | | |
| | K | 0.33-19.4 mg/L | | 20.3 | 26.5 | | | | | | | | | | | |
| | M-Spike | 0 g/dL | | 0.63 | 0.68 | | | | | | | | | | | |
| | M-Spike (urine, 24 hour) | 0 g/dL | | 114.7 | | | | | | | | | | | | |
| | IMWG Response | | | | | | | | | | | | | | | |
| 12 (2.4) 1q21 pos | IgA | | | 1510 | 1440 | 1120 | 948 | 799 | 653 | 698 | 634 | 492 | 417 | 394 | 353 | 391 |
| | K | 3.3-19.4 mg/L | | 18.3 | 21.2 | 18.1 | 18.0 | 16.3 | 14.6 | 12.3 | 12.2 | 10.7 | 12.5 | 10.9 | 13.6 | 12.6 |
| | Serum M-spike | 0 g/dL | | | 1.4 | 1.0 | 0.8 | 0.6 | 0.5 | 0.5 | 0.4 | 0.4 | 0.3 | 0.3 | 0.3 | 0.3 |
| | IMWG Response | | | | | | | PR | | PR | | PR | | OFF | | |
| 13 (2.4) 1q21 pos | IgG | 672-1760 | | | 2010 | | | | | | | | | | | |
| | K | 3.3-19.4 mg/L | | 135.2 | 139.0 | | | | | | | | | | | |
| | Serum M-Spike | 0 g/dL | | | 2.5 | | | | | | | | | | | |
| | IMWG Response | | | | | | | | | | | | | | | |

TABLE 24-continued

Biomarker results for refractory multiple myeloma patients treated with FOR46 in the dose escalation trial.

| Patient (Dose) | Analyte | Reference Range | Screen | C1 D1 | C2 D1 | C3 D1 | C4 D1 | C5 D1 | C6 D1 | C7 D1 | C8 D1 | C9 D1 | C10 | C11 | C12 | EOT or Status |
|---|---|---|---|---|---|---|---|---|---|---|---|---|---|---|---|---|
| 14 (2.4) 1q21 pos | IgG | 635-1741 mg/dL | | 345 | 339 | | | | | | | | | | | |
| | K | .33-1.94 mg/L | 28.72 | 68.11 | 48.16 | 42.16 | 36.18 | 34.78 | 35.57 | | | | | | | |
| | M-Spike (urine, 24 hour) | 0 mg/day | 540 | | | 144 | 202 | | 95 | | | | | | | |
| | IMWG Response | | | | | PR | MR | | PR | | | | | | | |
| 15 (2.4) 1q21 neg | IgG | 635-1741 mg/dL | | 345 | 339 | | | | | | | | | | | |
| | K | .33-1.94 mg/L | 2.61 | 3.67 | 5.39 | | | | | | | | | | | |
| | Serum M-Spike | 0 g/dL | | det | Not done | | | | | | | | | | | |
| | IMWG Response | | | | NE | | | | | | | | | | | |

Dose in mg/kg;
C: course;
D: day;
EOT: end of treatment;
K: kappa light chain;
λ: lambda light chain.
M-spike levels were measured in serum unless otherwise indicated.

TABLE 25

Biomarker results for refractory multiple myeloma patients treated with FOR46 in the 2.4 mg/kg (adjusted body weight) dose expansion trial.

| Patient ID | Test Name | Reference Range | Screen | C1D1 | C1D15 | C2D1 | C3D1 | C4D1 | C5D1 | C6D1 |
|---|---|---|---|---|---|---|---|---|---|---|
| 005-06-101 1 q gain pos | IgG | 610-1616 mg/dL | 3079 | 3361 | | 3301 | 4029 | | | |
| | Serum Lambda light chain | 5.7-26.3 mg/dL | 129 | 142.7 | | 191.9 | 303.6 | | | |
| | Serum M-spike | 0 g/dL | 2.14 | 2.22 | | 2.6 | 3.21 | | | |
| | IMWG Response | | | | | | PD | | | |
| 001-06-102 1 q gain pos (87%) | IgG | 672-1760 mg/dL | 3440 | 3520 | | 2300 | 1770 | 1310 | 1220 | 1530 |
| | Serum Lambda light chain | 5.7-26.3 mg/dL | 131.6 | 156 | | 56.7 | 31.6 | 59.4 | 97.7 | 128 |
| | Serum M-spike | 0 g/dL | 2.4 | 2.5 | | 1.6 | 1.5 | 1.1 | 1.0 | pending |
| | IMWG Response | | | | | | | PR | | |
| 006-06-103 1 q gain pos | IgG | 610-1616 mg/dL | 8132 | 8441 | | 8949 | 8949 | D/C | | |
| | Serum Lambda light chain | 5.7-26.3 mg/L | 384.1 | 328.1 | | 477.4 | 442.2 | | | |
| | Serum M-spike | 0 g/dL | 6.35 | 6.53 | | 7.98 | 7.54 | PD | | |
| | IMWG Response | | | | | | | | | |
| 005-06-104 1 q gain? | IgG | 672-1760 mg/dL | 1872 | 1706 | | 1357 | | | | |
| | Serum Lambda light chain | 3.3-19.4 mg/dL | 1790 | 838 | | 1113 | | | | |
| | Serum M-spike | 0 g/dL | 1.33 | 1.37 | | 1.31 | | | | |
| | IMWG Response | | | | | | | | | |

TABLE 25-continued

Biomarker results for refractory multiple myeloma patients treated with FOR46 in the 2.4 mg/kg (adjusted body weight) dose expansion trial.

| Patient ID | Test Name | Reference Range | Screen | C1D1 | C1D15 | C2D1 | C3D1 | C4D1 | C5D1 | C6D1 |
|---|---|---|---|---|---|---|---|---|---|---|
| 001-06-105 1 q gain neg | IgG | 672-1760 mg/dL | 7350 | 7800 | | 7150 | | | | |
| | Serum Lambda light chain | 3.3-19.4 mg/dL | 141 | 106.7 | | 131.9 | | | | |
| | Serum M-spike | 0 g/dL | 4.7 | 5.0 | | 5.0 | | | | |
| | IMWG Response | | | | | | | | | |
| 006-06-106 1 q gain pos 88% of cells 3 copies | IgG | 35-242 mg/dL | 3548 | 2820 | | 2687 | 2992 | | | |
| | Serum Lambda light chain | 5.7-26.3 mg/dL | 49.4 | 46.5 | | 77.7 | 82.0 | | | |
| | Serum M-spike (M1 + M2) | 0 g/dL | 1.79 | 1.43 | | 1.42 | 1.44 | | | |
| | IMWG Response | | | | | | | | | |
| 001-06-107 1 q gain pos | IgG | 672-1760 mg/dL | 3870 | 3900 | | 3940 | 4990 EOT | | | |
| | Serum Lambda light chain | 3.3-19.4 mg/dL | 121.2 | 106.6 | | 174.1 | 272.7 | | | |
| | Serum M-spike | 0 g/dL | 3.2 | 3.5 | | 3.6 | | | | |
| | IMWG Response | | | | | | | | | |
| 001-06-108 1 q gain pos | IgG | 672-1760 mg/dL | 5250 | 5550 | 5430 | 5630 | 5280 EOT | | | |
| | Serum Lambda light chain | 3.3-19.4 mg/dL | 963.8 | 1022.5 | 643.1 | 1162 | 1247 | | | |
| | Serum M-spike | 0 g/dL | 3.9 | 3.9 | 3.7 | 3.6 | 3.4 | | | |
| | IMWG Response | | | | | | | | | |
| 001-06-109 1 q gain pos | IgG | 672-1760 mg/dL | 3430 | 5050 | | | | | | |
| | Serum Lambda light chain | 3.3-19.4 mg/dL | 15.9 | | | | | | | |
| | Serum M-spike | 0 g/dL | 2.9 | | | | | | | |
| | LDH | 125-243 U/L | 710 | | | | | | | |
| | IMWG Response | | | | | | | | | |
| 002-06-110 1 q gain pos | IgG | 35-242 mg/dL | 660 | 611 | | | | | | |
| | Serum Lambda light chain | 5.7-26.3 mg/dL | 2.09 | | | | | | | |
| | Serum M-spike (M1 + M2) | 0 g/dL | | | | | | | | |
| | IMWG Response | | | | | | | | | |

C: course;
D: day;
EOT: end of treatment;
K: kappa light chain;
λ: lambda light chain;
PR: partial response;
PD: progressive disease;
D/C: discontinued care.
M-spike levels were measured in serum unless otherwise indicated.

Example 6: Formulation of FOR46

The objective of this study was to develop an optimized formulation for FOR46. The thermal stability study, freeze-thaw stability study and agitation study were performed in the formulation development process. Stability of the drug product was evaluated by assays including the general appearance, protein concentration, pH as well as SEC- HPLC, cIEF, Caliper-SDS_R/NR and MFI analysis in order to select the optimal formulation.

Analytical Methods

Appearance

The appearance of all samples, including clarity, color and visible particles, was examined against black and white background using a YB-2 light box.

pH

Sample pH was measured using a Seven Multi S4.0 pH meter with an Inlab®Micro electrode. The pH meter was calibrated prior to use each time.

Protein Concentration

Protein concentration was determined by UV280 readings using a NanoDrop 2000 spectrophotometer. The extinction coefficient used in all evaluation studies was 1.571 AU*mL*mg-1*cm-1 All measurements were repeated twice with 2.5 µL sample each time and an average result was reported.

SEC-HPLC

Size exclusion chromatography was performed using an Agilent 1260 Infinity system with the TSKGel G3000SWXL size exclusion chromatography column (300×7.8 mm, 5 µm) at 25° C. The flow rate was set at 1.0 mL/min in isocratic gradient. The mobile phase consisted of 50 mM sodium phosphate buffer, 300 mM NaCl with pH 6.8±0.1 for each sample. A loading amount of 100µg sample was injected and detected at 280 nm with a UV detector. Data was analyzed using Waters Empower.

cIEF

The cIEF was performed on ProteinSimple iCE3 equipment with FC-coated cIEF cartridge. In the formulation development stage, 50 µg of each sample was mixed with 100 11 L of master mix which was consisted of pI marker 4.22/7.46, Servalyt 2-9, Servalyt 3-5, 1% methyl cellulose solution and 8M urea solution. After mixing, the sample was focused for 1 minute at 1500 V and for 8 minutes at 3000 V. Detection wavelength was set 280 nm to evaluate the charge variants distribution in different pI range. In the forced degradation study, the pI marker in the master mix was changed to 4.22/7.05.

Caliper-SDS_R&NR

Before sample was tested, pretreatments such as incubation with sample buffer, SDS and N-ethylmaleimide (for non-reduced or NR) or dithiothreitol (for reduced or R) at 70° C. for 10 min were necessary. Then the loading mix with a minimum volume of 42 µL (final protein concentration of 0.045 mg/mL) was test by LabChip GXII Touch at excitation/emission wavelength of 635 and 700 nm. The final results were analyzed by the commercial software: LabChip GX Reviewer.

CE-SDS_R/NR

Non-reduced CE-SDS was performed using a Beckman Coulter PA800 Enhanced or PA800 Plus instrument equipped with a photodiode array detector. Samples were diluted to 4 mg/mL by Dilution Solution (PB-CA), and then heated in the presence of 75 pI SDS sample buffer and 5µl 100 mM NEM at 60° C. for 10 min for non-reduced CE-SDS. Samples were injected using +5 kV for 15 s followed by separation at +11 kV for 30 min. Detection was performed at 220 nm.

DSC Analysis

The DSC analysis was performed by MicroCal™ VP-Capillary DSC System from GE Healthcare, model AS12-001C. The protein sample was first diluted to 1 mg/mL with formulation buffer before analysis. 300 µL of tested protein sample was added to 96-well plate and 300 µL of its corresponding buffer was added as reference. The samples were heated from 10° C. to 110° C. at a heating rate of 200° C./h in the capillary DSC system. The sample was tested twice and the DSC results (Tm Onset and Tm values) were analyzed by Origin 7.0 DSC Automated Analysis software.

3. Excipient screening 3.1 Study Objective

This study was to evaluate the influence of NaCl, Arg-HCl, sucrose and trehalose on stabilizing FOR46 in the selected buffer.

3.2 Study Parameters

FOR46 was formulated at a concentration of 10 mg/mL in 20 mM Histidine buffers pH 6.0. As given in Table 1, for each formulation, 140 mM NaCl, 150 mM Arg-HCl, 8% (w/v) sucrose or trehalose was added as stabilizer, respectively, and no adding was set as blank.

The sample in each formulation was subjected to up to five cycles of freeze/thaw stress and thermal stress (40° C. and 25° C.). The stability of the FOR46 in each formulation was evaluated with different assays as given in Table 26.

TABLE 26

Formulation options.

| F # | Buffer | pH | Excipients |
|---|---|---|---|
| F1 | 20 mM Histidine | 6.0 | 140 mM NaCl |
| F2 | 20 mM Histidine | 6.0 | 150 mM Arg-HCl |
| F3 | 20 mM Histidine | 6.0 | 8% Sucrose |
| F4 | 20 mM Histidine | 6.0 | 8% Trehalose |
| F5 | 20 mM Histidine | 6.0 | / |

TABLE 27

Stability study plan for excipient screening.

| F# | Stress | Condition | T0 | Sampling points and Assay | | |
|---|---|---|---|---|---|---|
| F1, F2, F3, F4 and F5 | Thermal | 25° C. | x | | 2 W | 4 W |
| | | | | | x | x |
| | | 40° C. | | 1 W | 2 W | 4 W |
| | | | | x | x | x |
| | Freeze and Thaw | -40° C. to RT | 3 C | 5 C | | |
| | | | x | x | | |

X = Appearance, pH, protein concentration, SEC-HPLC, cIEF, Caliper-SDS, DAR 3.4 Sample Preparation FOR46 was buffer exchanged to 20 mM Histidine at pH 6.0 via the ultrafiltration method. After adding appropriate amount of sucrose, trehalose, Arg-HCl or NaCl, the protein concentration was adjusted to 10 mg/mL then all samples were aseptically filtered with 0.22-µm PES membrane filter. For each formulation sample, eight (8) 2R glass vials were filled with 1 mL of filtered DS. One (1) vial was subjected to three and five cycles of freeze and thaw stress, respectively. In each cycle, the freezing time was at least 12 hours in a −40° C. freezer. The sample was thawed at room temperature. Three (3) vials were incubated at 40° C. Two vials were incubated at 25° C. One vial from each study condition was sampled for analysis at the designated time point. One (1) vial served as T0.

3.5 Results and Discussion 3.5.1 Appearance, Protein Concentration and pH Results Obvious precipitation was observed in F1 and F2 right after a short storage at 5° C., which could be attributed to the high ionic strength in formulations. Therefore, F1 and F2 were excluded from the study. All the rest of the samples were colorless, slightly opalescent and free of visible particles at the beginning of the study.

After incubation at 25° C. as well as 40 s for up to 4 weeks, F5 were free of visible particles and many particles were observed in both F3 and F4. It could be attributed to protein denaturation induced by higher surface tension of formulations with sugar, and the referring adverse effect could be eliminated by addition of surfactant in finalized formulation.

No substantial change in appearance was found in F3, F4 and F5 after up to 5 cycles of freeze and thaw stress.

No substantial change in pH and protein concentration was found at 40° C., 25° C. and after 5 cycles of freeze and thaw.

SEC Purity

The SEC purity data was summarized in Table 28. Based on SEC data at 25° C. and after up to 5 cycles of Freeze and Thaw, no substantial change was found in any samples. After incubation for 4 weeks at 40° C., the SEC purity of F5 was obviously lower than F3 and F4. So, it could be concluded that the stabilizing effect of sucrose and trehalose to ADC was unexpectedly substantial and comparable.

TABLE 28

SEC purity results of FOR46 excipient screening study.

| Sample information | | T0 | FT 3 C | FT 5 C | 25° C. 2 W | 25° C. 4 W | 40° C. 1 W | 40° C. 2 W | 40° C. 4 W |
|---|---|---|---|---|---|---|---|---|---|
| F3 | Main peak % | 97.9 | 98.6 | 98.5 | 97.5 | 98.1 | 96.0 | 93.2 | 94.9 |
|  | HMW % | 2.0 | 1.3 | 1.3 | 2.3 | 1.6 | 3.8 | 4.6 | 4.22 |
|  | LMW % | 0.1 | 0.2 | 0.2 | 0.1 | 0.3 | 0.2 | 2.1 | 0.92 |
| F4 | Main peak % | 97.9 | 98.6 | 98.5 | 97.5 | 98.1 | 95.9 | 93.2 | 94.6 |
|  | HMW % | 2.0 | 1.2 | 1.3 | 2.3 | 1.6 | 3.9 | 4.8 | 4.4 |
|  | LMW % | 0.1 | 0.2 | 0.2 | 0.2 | 0.3 | 0.3 | 2.0 | 0.9 |
| F5 | Main peak % | 97.5 | 98.4 | 98.4 | 96.8 | 97.8 | 94.7 | 90.8 | 92.6 |
|  | HMW % | 2.4 | 1.4 | 1.4 | 3.0 | 1.9 | 4.9 | 6.3 | 6.2 |
|  | LMW % | 0.1 | 0.2 | 0.2 | 0.2 | 0.4 | 0.4 | 2.9 | 1.2 |

Caliper-SDS_R/NR Purity

No substantial change in Caliper-SDS_R/NR purity was found in any samples after up to 5 cycles of Freeze and Thaw and incubation for 4 weeks at 25° C. as well as 40° C.

cIEF

Based on cIEF data, a substantial decrease in main peak purity was found in all samples after incubation for 4 weeks at 40° C. as well as 25° C., and the decrease speed was comparable among F3-F5. No substantial change was found after up to 5 cycles of Freeze and Thaw.

Drug to Antibody Ratio (DAR)

No substantial change in DAR was found in all samples after incubation for 4 weeks at 40° C. as well as 25° C. and up to 5 cycles of freeze and thaw.

Conclusion

Even though the worse appearance was observed in buffer with trehalose and sucrose, the adverse effect induced by higher surface tension would be reversible by addition of surfactant. Surprisingly, the SEC purity results indicated that sucrose and trehalose showed the outstanding and comparable performance in stabilizing FOR46 against thermal stress. Considering the commercial cost, the sucrose was selected as excipient in optimized formulation. The surfactant screening study will be performed in 20 mM Histidine buffer at pH 6.0 with 8% (w/v) sucrose (F3).

4. Surfactant Screening

This study was to evaluate the stabilizing effect of 2 different surfactants (PS-80 and PS-20) at 3 content levels in 20 mM Histidine buffer with 8% (w/v) sucrose. Based on DAR data (given in Table 34), no substantial change in DAR was found in all samples after incubation for 4 weeks at 40° C. as well as 25° C. and up to 5 cycles of freeze and thaw.

Study Parameters

FOR46 was formulated at 10 mg/mL in 20 mM Histidine buffer at pH 6.0 with 8% (w/v) sucrose in 7 formulations as given in Table 29. PS-80 or PS-20 with 3 content levels respectively was added to each formulation and the formulation without surfactant was included as blank. The sample in each formulation was subjected to up to five cycles of freeze and thaw, thermal stress (40° C.) and agitation stress (300 rpm, 2 days). The stability of the ADC at designated time point was evaluated with different assays.

TABLE 29

Formulation option of FOR46 excipient screening.

| Formulation No. | pH/buffer | Excipients | Surfactant Comments |
|---|---|---|---|
| 1 |  |  | NA |
| 2 |  |  | 0.01% PS-80 |
| 3 |  |  | 0.02% PS-80 |
| 4 | 20 mM His, pH 6.0 | 8% sucrose | 0.03% PS-80 |
| 5 |  |  | 0.015% PS-20 |
| 6 |  |  | 0.02% PS-20 |
| 7 |  |  | 0.03% PS-20 |

TABLE 30

Formulation option of FOR46 excipient screening.

| Attributes | Condition | T0 | Sampling Points and Assay | |
|---|---|---|---|---|
|  |  |  | 2W | 4W |
| Thermal | 40° C. | X, Y, Z | X | X, Z |
| Freeze/Thaw | −40° C. to RT |  | 5 Cycles X, Y, Z | |
| Agitation | 25° C., 300 rpm |  | 2D X, Y, Z | |

X = Appearance, pH, protein concentration SEC-HPLC, cIEF, SDS caliper R; Y = MFT; Z = binding antigen 4.3 Drug Materials FOR46 formulated in 20 mM histidine buffer at pH 6.0 with 8% (w/v) sucrose was stored at 2-8° C. before the surfactant screening study.

Sample Preparation

After adding the designed amount of PS-80 or PS-20, WBP2095 ADC DS was aseptically filtered with 0.22-μm PES membrane filter. For each formulation sample, eight (8) 2R glass vials were filled with 1 mL of filtered DS, respectively. Two (2) vials was subjected to five cycles of freeze and thaw stress. In each cycle, the freezing time was at least 12 hours in a −40'C freezer. The sample was thawed at room temperature. Two (2) vials were incubated at 40° C. Two (2) vials were subjected to agitation for 2 days at a speed of 300 rpm at ambient temperature. One vial from 40° C. and two vials from Freeze and Thaw stress as well as agitation stress was sampled for analysis at the designated time point. Two (2) vial served as T0.

4.5 Results and Discussion 4.5.1 Appearance, Protein Concentration and pH Results After 5 cycles of freeze and thaw, no substantial change in appearance was found among all samples. After agitation for 2 days at a speed of 300 rpm and incubation for 4 weeks at 40° C., particles and fibers were observed in F1 (without surfactant). It indicated that the presence of surfactant could be essential to protect ADC in thermal and agitation stress condition.

No substantial change was found in pH and protein concentration.

4.5.2 SEC Purity

After 5 cycles of freeze and thaw and agitation for 2 days, no substantial change in SEC purity was found. After incubation at 40° C. for 4 weeks, a decline of 6% in main peak purity was found in all 7 formulations. Based on SEC purity data, all formulations were comparable in all conditions.

4.5.3 CE-SDS_R Purity

No substantial change in CE-SDS R purity was found in thermal stress, freeze and thaw and agitation stress condition.

4.5.4 cIEF

After 5 cycles of freeze and thaw and agitation for 2 days, no substantial change in cIEF was found. In thermal stress, the main peak purity decreased substantially while the acid peak purity increased accordingly. However, the change among all formulations was comparable.

4.5.5 Potency

Based on previous data, 3 leading formulations (F2, F3 and F4) were selected to perform binding potency assay. In thermal stress, agitation stress and freeze and thaw stress, no substantial change in binding potency was found.

4.5.6 MFI

Surprisingly, based on MFI results, more than 10 times of particles in F1 was found compared to the rest formulations. It suggested more sub-visible particles in F1 than the other formulations.

TABLE 31

MFI results of FOR46 in surfactant screening study.

| Sample | | T0 | FT | Agitation |
|---|---|---|---|---|
| F1 | 2~5 um | 7085 | 2561 | 4874 |
| | 5~10 um | 1340 | 523 | 1337 |
| | 10~25 um | 194 | 79 | 478 |
| | ≥25 um | 15 | 4 | 69 |
| F2 | 2~5 um | 542 | 368 | 404 |
| | 5~10 um | 104 | 51 | 33 |
| | 10~25 um | 22 | 9 | 5 |
| | ≥25 um | 0 | 0 | 0 |
| F3 | 2~5 um | 1467 | 340 | 258 |
| | 5~10 um | 379 | 35 | 15 |
| | 10~25 um | 94 | 10 | 4 |
| | ≥25 um | 2 | 0 | 0 |
| F4 | 2~5 um | 545 | 969 | 332 |
| | 5~10 um | 53 | 109 | 56 |
| | 10~25 um | 7 | 12 | 10 |
| | ≥25 um | 4 | 0 | 2 |
| F5 | 2~5 um | 692 | 716 | 1050 |
| | 5~10 um | 84 | 60 | 99 |
| | 10~25 um | 10 | 9 | 4 |
| | ≥25 um | 0 | 0 | 0 |
| F6 | 2~5 um | 550 | 337 | 294 |
| | 5~10 um | 63 | 30 | 25 |
| | 10~25 um | 20 | 12 | 10 |
| | ≥25 um | 5 | 2 | 4 |
| F7 | 2~5 um | 813 | 965 | 689 |
| | 5~10 um | 114 | 171 | 130 |
| | 10~25 um | 30 | 33 | 78 |
| | ≥25 um | 30 | 33 | 78 |

4.6 Conclusion

Based on appearance and MFI results, surfactant played an unexpectedly important role in protecting ADC in thermal and agitation stress condition. However, no difference was found among 6 formulations with two different surfactants (PS-80 and PS-20) at three content levels. Considering the lower CMC (critical micelle concentration) of PS-80 compared to PS-20, which suggested the lower effective concentration of surfactant, and the probable adverse effect introduced by degradation of PS-80 at high content level, 0.01% (w/v) PS-80 was selected in the final formulation.

FOR46 (10 mg/mL) in 20 mM histidine buffer at pH 6.0 with 8% (w/v) sucrose and 0.01% (w/v) PS-80 was selected as the final formulation.

What is claimed is:

1. A pharmaceutical composition comprising an immunoconjugate, a pharmaceutically acceptable buffer, and a pharmaceutically acceptable stabilizing agent, wherein the immunoconjugate comprises:
   a recombinant antibody comprising:
      a first heavy chain comprising the SEQ ID NO: 9,
      a first light chain comprising the SEQ ID NO: 10,
      a second heavy chain comprising the SEQ ID NO: 9, and
      a second light chain comprising the SEQ ID NO: 10; and
   one, two, three or four pairs of adducts;
   wherein each adduct of the one, two, three or four pairs of adducts comprises a monomethylauristatin E (MMAE) that is conjugated to the recombinant antibody via a maleimidocaproyl-valine-citrulline-para-amino benzyloxycarbonyl (mc-vc-PAB) linker;
   wherein each of the one, two, three or four pairs of adducts is conjugated to a pair of cysteine residues of the recombinant antibody,
   wherein the pairs of cysteine residues are selected from:
      C219 of the first heavy chain and C214 of the first light chain;
      C219 of the second heavy chain and C214 of the second light chain;
      C225 of the first heavy chain and C225 of the second heavy chain; and
      C228 of the first heavy chain and C228 of the second heavy chain;

wherein the buffer is about 20 mM histidine and has a pH of about 6.0, wherein the stabilizing agent is about 0.01% polysorbate-80, and wherein the pharmaceutical composition further comprises about 8.0% sucrose.

2. The pharmaceutical composition of claim 1, wherein the immunoconjugate comprises about two pairs of the adducts.

3. A method of treating metastatic castration-resistant prostate cancer in a subject in need thereof comprising administering the pharmaceutical composition of claim 1 to the subject at a dose of about 1.8 mg to about 3.0 mg of the immunoconjugate per kg of adjusted body weight every 21 days over at least three cycles via intravenous infusion.

4. A method of treating relapsed or refractory multiple myeloma in a subject in need thereof comprising administering the pharmaceutical composition of claim 1 to the subject at a dose of about 1.2 mg to about 3.0 mg of the immunoconjugate per kg of adjusted body weight every 21 days over at least three cycles via intravenous infusion.

* * * * *

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic antibody VH CDR1 domain

<400> SEQUENCE: 1

Gly Leu Thr Val Asn Asn Tyr Ala
1               5

<210> SEQ ID NO 2
<211> LENGTH: 8
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<223> OTHER INFORMATION: Synthetic antibody VH CDR2 domain

<400> SEQUENCE: 2

Ile Ser Tyr Asp Gly Asn Asn Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic antibody VH CDR3 domain

<400> SEQUENCE: 3

Ala Lys Gly Gly Gly Tyr Phe Asp Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic antibody VL CDR1 domain

<400> SEQUENCE: 4

Ser Ser Asn Ile Gly Ala Gly Tyr Asp
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic antibody VL CDR2 domain

<400> SEQUENCE: 5

Gly Asn Asn
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic antibody VL CDR3 domain

<400> SEQUENCE: 6

Ser Ser Tyr Thr Ser Gly Thr Trp Leu
1               5

<210> SEQ ID NO 7
<211> LENGTH: 116
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Synthetic antibody VH domain

<400> SEQUENCE: 7

Gln Val Gln Leu Val Gln Ser Gly Gly Gly Val Val Gln Pro Gly Arg
1               5                   10                  15

Ser Leu Arg Leu Ala Cys Ala Ala Ser Gly Leu Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser
        115

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic antibody VL domain

<400> SEQUENCE: 8

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu
            100                 105

<210> SEQ ID NO 9
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic antibody H domain

<400> SEQUENCE: 9
```

-continued

```
Gln Val Gln Leu Val Gln Ser Gly Gly Gly Val Gln Pro Gly Arg
1               5                   10                  15

Ser Leu Arg Leu Ala Cys Ala Ala Ser Gly Leu Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
```

```
                420             425             430
Asn His Tyr Thr Gln Lys Ser Leu Ser Leu Ser Pro Gly Lys
        435             440             445

<210> SEQ ID NO 10
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic antibody L domain

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```